United States Patent
LaPierre et al.

(10) Patent No.: US 10,368,881 B2
(45) Date of Patent: Aug. 6, 2019

(54) METHOD AND APPARATUS FOR MINIMALLY INVASIVE POSTEROLATERAL SPINAL FUSION

(71) Applicant: Quandary Medical, LLC, Denver, CO (US)

(72) Inventors: Leighton Joseph LaPierre, Thornton, CO (US); Scott Noble, Denver, CO (US); Ryan Alexander Arce, Denver, CO (US); Jeffrey R Schell, Denver, CO (US); Yuta Okkotsu, Aurora, CO (US); David C. Eyvazzadeh, Denver, CO (US); Brandon B. Arthurs, Wilmington, NC (US); Gerald R. Schell, Bay City, MI (US)

(73) Assignee: Quandary Medical, LLC, Denver, CO (US)

( * ) Notice: Subject to any disclaimer, the term of this patent is extended or adjusted under 35 U.S.C. 154(b) by 229 days.

(21) Appl. No.: 15/612,781

(22) Filed: Jun. 2, 2017

(65) Prior Publication Data
US 2017/0348034 A1    Dec. 7, 2017

Related U.S. Application Data

(60) Provisional application No. 62/345,667, filed on Jun. 3, 2016.

(51) Int. Cl.
*A61B 17/88* (2006.01)
*A61B 17/16* (2006.01)
(Continued)

(52) U.S. Cl.
CPC ...... *A61B 17/1635* (2013.01); *A61B 17/1671* (2013.01); *A61B 17/1757* (2013.01);
(Continued)

(58) Field of Classification Search
CPC ............ A61B 17/1635; A61B 17/1671; A61B 17/1757
See application file for complete search history.

(56) References Cited

U.S. PATENT DOCUMENTS

| 2,526,662 | A | * | 10/1950 | Hipps | ................ | A61B 17/1635 |
| | | | | | | 408/67 |
| 4,541,423 | A | | 9/1985 | Barber | | |

(Continued)

FOREIGN PATENT DOCUMENTS

| JP | 2010012281 | 1/2010 |
| JP | 5657225 | 1/2015 |

(Continued)

OTHER PUBLICATIONS

Macnab et al. 1971. "The Blood Supply of the Lumbar Spine and Its Application to the Technique of Intertransverse Lumbar Fusion" J. Bone and Joint Surg. 53B(4): 628-638.
(Continued)

*Primary Examiner* — Christian A Sevilla
(74) *Attorney, Agent, or Firm* — Rocky Mountain Patent, LLC

(57) ABSTRACT

Certain embodiments of the invention relate to a surgical procedure resulting in the fusion of transverse processes. The disclosure herein presents novel approaches for accessing transverse processes of the spine, novel methods for the delivery of fusion material for the fusion of said transverse processes, and novel tools to facilitate the procedure. Certain embodiments of the invention include a graft delivery assembly, which has a delivery shaft, delivery sheath, and at least one curved rod. Bony material is position with a graft delivery assembly, in which retraction of the delivery shaft or sheath places the bone fusion material to the fusion site.
(Continued)

The graft delivery assembly further includes features to decorticate and prepare the bone surface for fusion.

20 Claims, 34 Drawing Sheets

(51) Int. Cl.
  *A61B 17/17* (2006.01)
  *A61B 17/34* (2006.01)
  *A61B 17/70* (2006.01)
  *A61B 17/32* (2006.01)
(52) U.S. Cl.
  CPC ...... *A61B 17/3421* (2013.01); *A61B 17/7061* (2013.01); *A61B 17/7089* (2013.01); *A61B 2017/32006* (2013.01); *A61B 2017/320052* (2013.01)

(56) References Cited

U.S. PATENT DOCUMENTS

| | | | |
|---|---|---|---|
| 5,334,194 | A | 8/1994 | Mikhail |
| 5,374,269 | A | 12/1994 | Rosenberg |
| 5,380,331 | A | 1/1995 | Mikhail |
| 5,624,446 | A | 4/1997 | Harryman, II |
| 5,741,261 | A | 4/1998 | Moskovitz |
| 5,857,995 | A | 1/1999 | Thomas |
| 5,885,291 | A | 3/1999 | Moskovitz |
| 5,968,062 | A | 10/1999 | Thomas |
| 5,976,146 | A | 11/1999 | Ogawa |
| 6,346,101 | B1 | 8/2002 | Hamada |
| 6,482,152 | B2 | 11/2002 | Kim |
| 6,666,891 | B2 | 12/2003 | Boehm, Jr. |
| 6,689,140 | B2 | 2/2004 | Cohen |
| 7,357,773 | B2 | 4/2008 | Watschke |
| 7,481,766 | B2 | 1/2009 | Lee |
| 7,553,307 | B2 | 6/2009 | Bleich |
| 7,822,485 | B2 | 10/2010 | Collins |
| 7,955,355 | B2 | 6/2011 | Chin |
| 8,002,798 | B2 | 8/2011 | Chin |
| 8,133,231 | B2 | 3/2012 | Martinek |
| 8,152,714 | B2 | 4/2012 | Garcia-Bengochea |
| 8,328,610 | B2 | 12/2012 | Patel |
| 8,425,602 | B2 | 4/2013 | Guyer |
| 8,486,077 | B1 | 7/2013 | Kornel |
| 8,597,299 | B2 | 12/2013 | Farr |
| 8,647,346 | B2 | 2/2014 | Bleich |
| 8,685,063 | B2 | 4/2014 | Chin |
| 8,721,691 | B2 | 5/2014 | Hua |
| 8,753,345 | B2 | 6/2014 | McCormack |
| 8,795,306 | B2 | 8/2014 | Smith |
| 8,834,472 | B2 | 9/2014 | McCormack |
| 8,852,191 | B2 | 10/2014 | Bertram, III |
| 8,894,655 | B2 | 11/2014 | Fallin |
| 8,915,927 | B2 | 12/2014 | Chu |
| RE45,336 | E | 1/2015 | Chin |
| 8,945,137 | B1 | 2/2015 | Greenhalgh |
| 8,974,461 | B2 | 3/2015 | Abdou |
| 8,979,851 | B2 | 3/2015 | Fallin |
| 9,005,288 | B2 | 4/2015 | McCormack |
| 9,060,878 | B2 | 6/2015 | Oktavec |
| 9,084,591 | B2 | 7/2015 | Reglos |
| 9,119,684 | B2 | 9/2015 | Fallin |
| 2002/0016583 | A1* | 2/2002 | Cragg ................ A61B 17/1671 604/500 |
| 2002/0045904 | A1* | 4/2002 | Fuss ........................ A61B 17/02 606/99 |
| 2003/0060826 | A1* | 3/2003 | Foley ............... A61B 17/00234 623/17.16 |
| 2004/0111102 | A1 | 6/2004 | Saller |
| 2004/0133217 | A1 | 7/2004 | Watschke |
| 2004/0220577 | A1 | 11/2004 | Cragg |
| 2005/0038514 | A1 | 2/2005 | Helm |
| 2005/0065517 | A1 | 3/2005 | Chin |
| 2005/0070913 | A1 | 3/2005 | Mibocker |
| 2005/0080320 | A1 | 4/2005 | Lee |
| 2005/0187556 | A1 | 8/2005 | Stack |
| 2005/0203529 | A1 | 9/2005 | Boehm, Jr. |
| 2006/0004396 | A1 | 1/2006 | Binder, Jr. |
| 2006/0258951 | A1 | 11/2006 | Bleich |
| 2008/0221586 | A1 | 9/2008 | Garcia-Bengochea |
| 2008/0228208 | A1 | 9/2008 | Wulfman |
| 2008/0255563 | A1 | 10/2008 | Farr |
| 2009/0177205 | A1 | 7/2009 | McCormack |
| 2010/0076502 | A1 | 3/2010 | Guyer |
| 2011/0230965 | A1 | 9/2011 | Schell |
| 2011/0282390 | A1 | 11/2011 | Hua |
| 2011/0301647 | A1 | 12/2011 | Hua |
| 2012/0016422 | A1 | 1/2012 | Hua |
| 2012/0221063 | A1 | 8/2012 | Abdou |
| 2012/0239041 | A1 | 9/2012 | Bleich |
| 2012/0253316 | A1 | 10/2012 | Oktavec |
| 2012/0323245 | A1 | 12/2012 | Bertram, III |
| 2013/0096587 | A1 | 4/2013 | Smith |
| 2013/0253591 | A1 | 9/2013 | Kornel |
| 2014/0058423 | A1 | 2/2014 | Smith |
| 2014/0172029 | A1 | 6/2014 | Guyer |
| 2014/0180291 | A1 | 6/2014 | Smith |
| 2015/0018887 | A1 | 1/2015 | Zappacosta |
| 2015/0182268 | A1 | 7/2015 | Donner |
| 2015/0190148 | A1 | 7/2015 | Greenhalgh |
| 2015/0209156 | A1 | 7/2015 | Greenhalgh |

FOREIGN PATENT DOCUMENTS

| | | | |
|---|---|---|---|
| JP | 2015503997 | A | 2/2015 |
| WO | 0176680 | A1 | 10/2001 |
| WO | 02091909 | A2 | 11/2002 |
| WO | 2006044727 | A2 | 4/2006 |
| WO | 2008058070 | A2 | 5/2008 |

OTHER PUBLICATIONS

Bobyn, et al. 2013. "Posterolateral inter-transverse lumbar fusion in a mouse model." Journal of Orthopaedic Surgery and Research. 8:2.
Inamadar et al. 2006. "Posterior lumbar interbody fusion versus intertransverse fusion in the treatment of lumbar spondylolisthesis." Journal of Orthopaedic Surgery. 14(1):21-6.

* cited by examiner

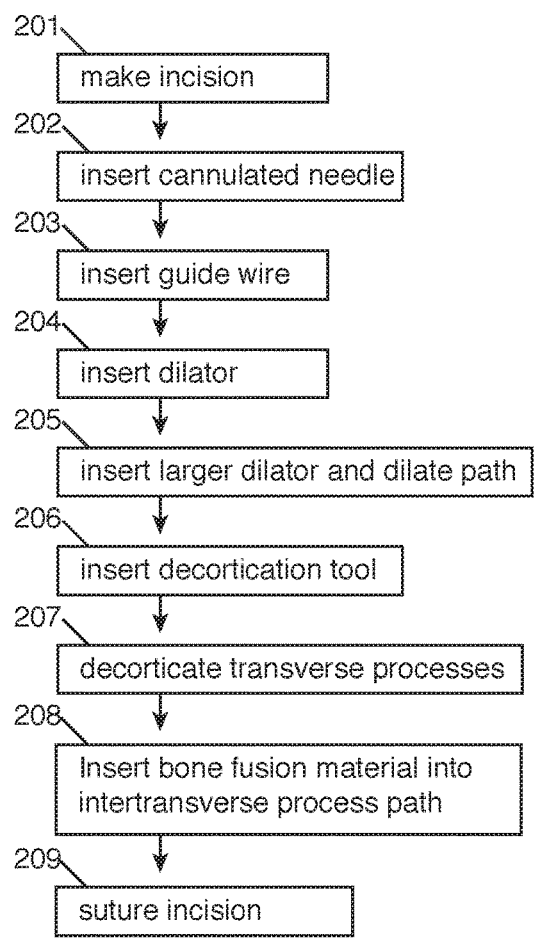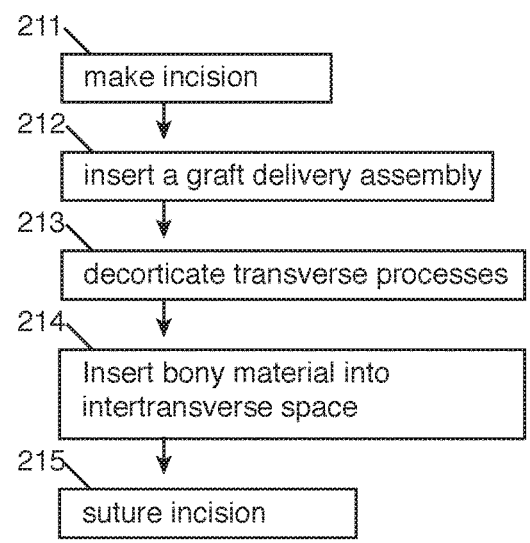
FIG. 2A
FIG. 2B

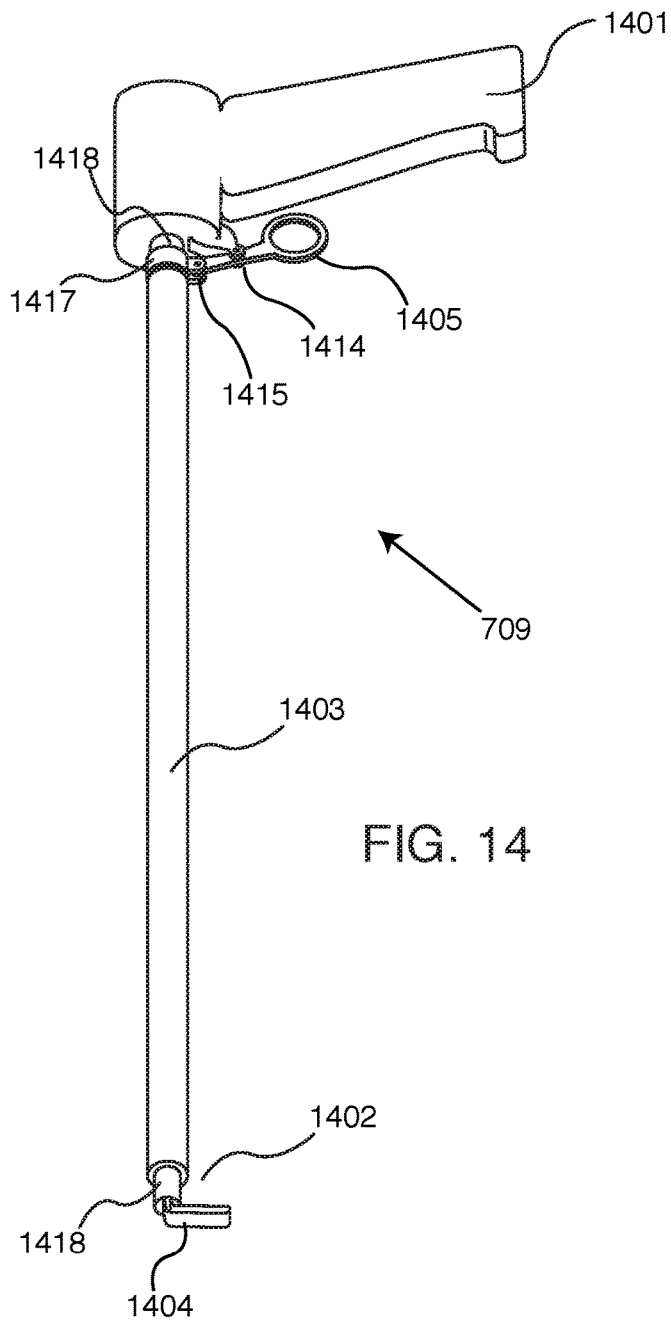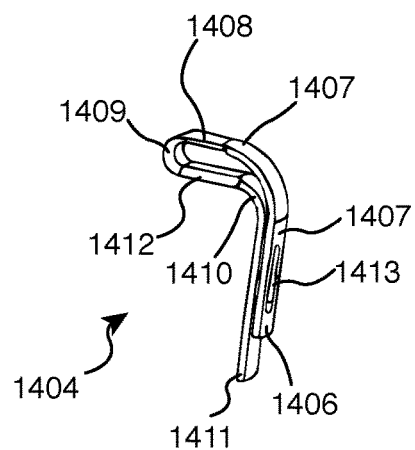
FIG. 14
FIG. 15

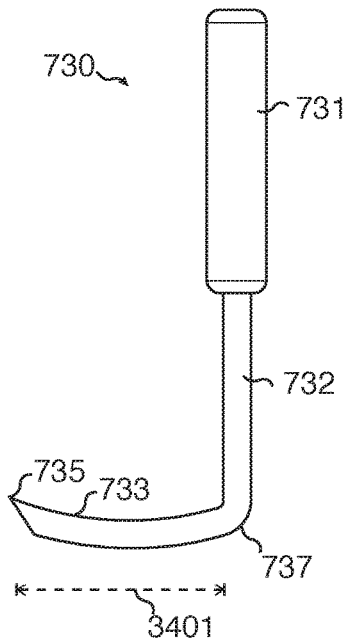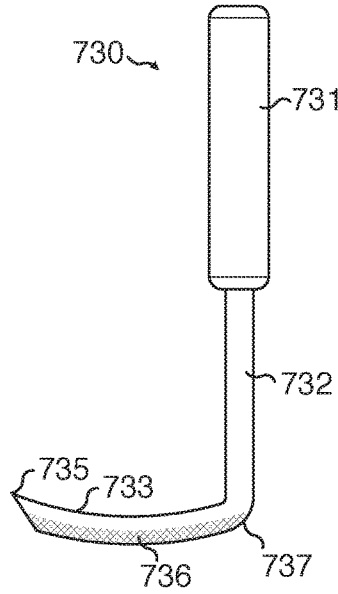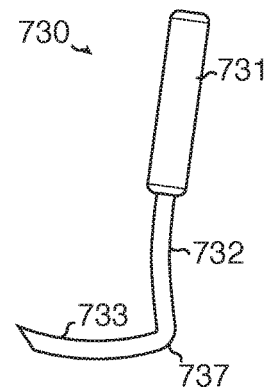
FIG. 34A  FIG. 34B  FIG. 34C
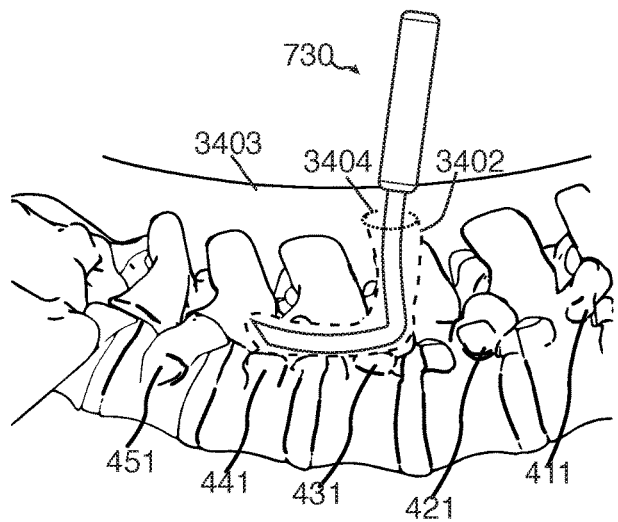
FIG. 34D
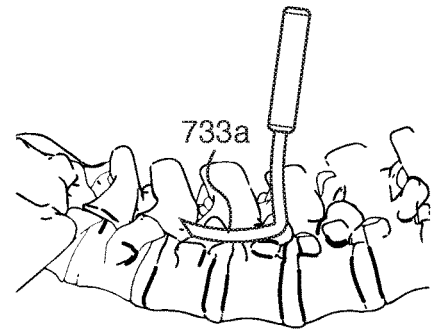
FIG. 34E
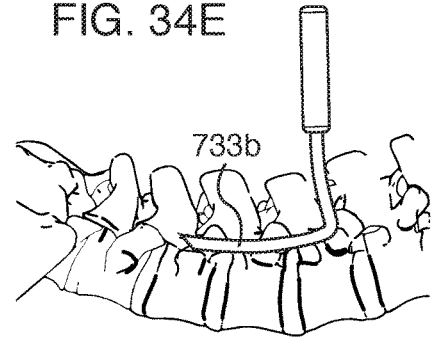
FIG. 34F

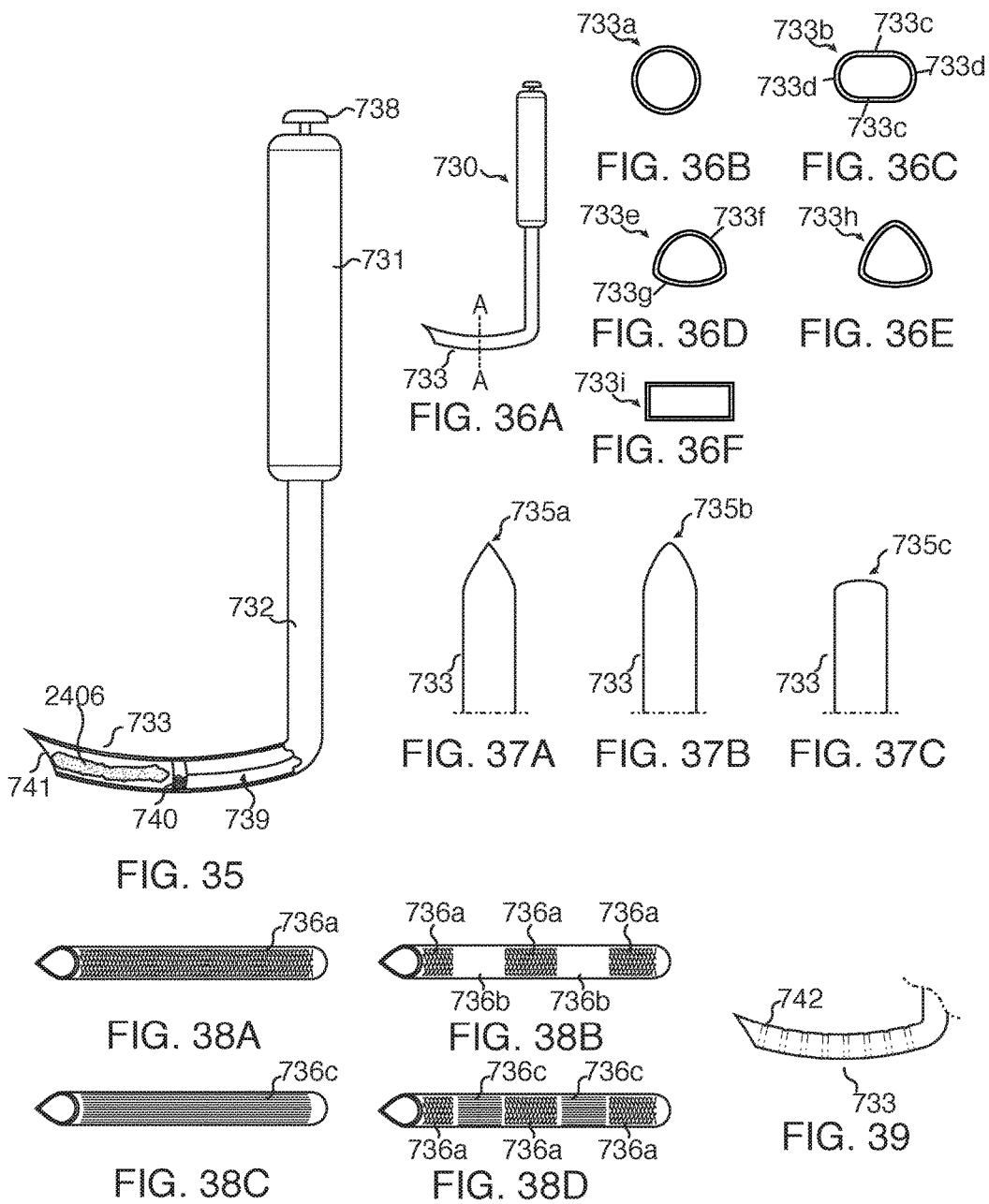

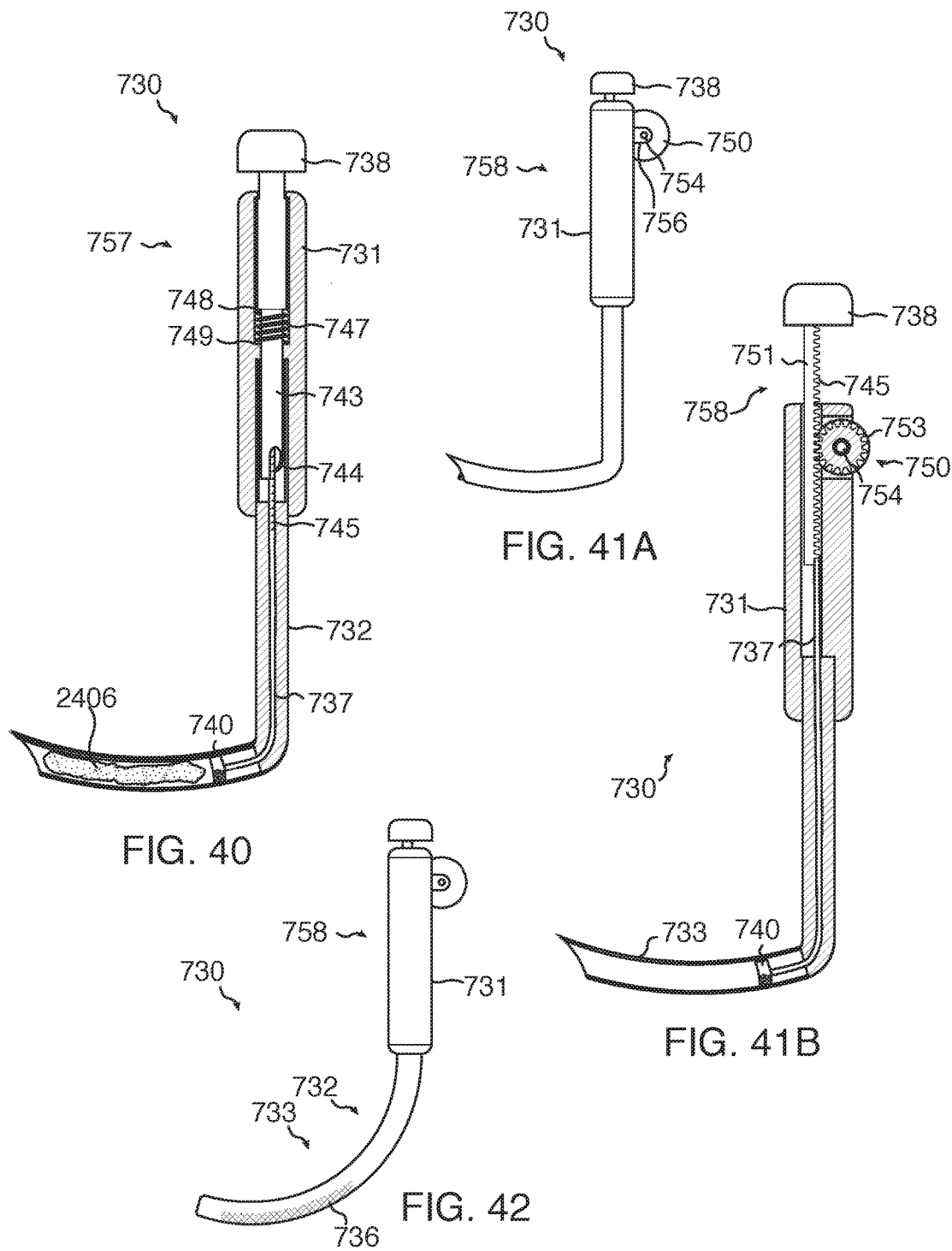

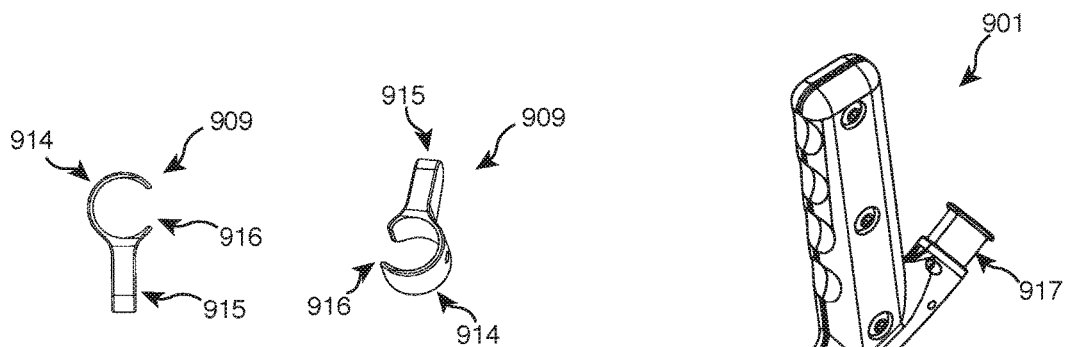
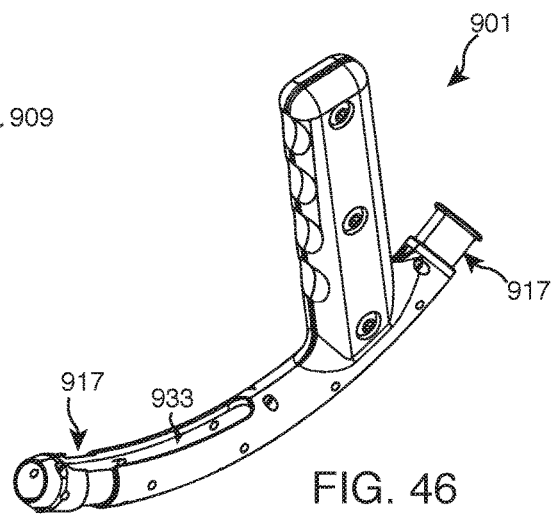
FIG. 45A    FIG. 45B    FIG. 46
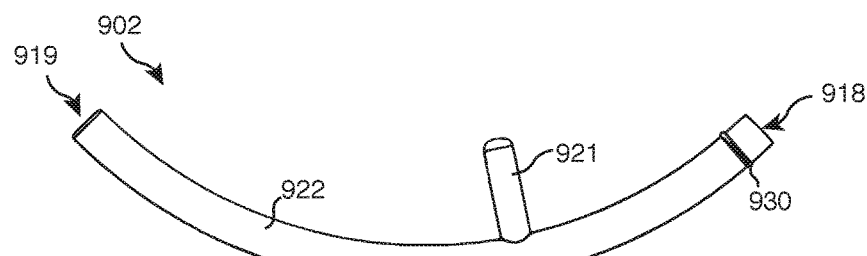
FIG. 47A
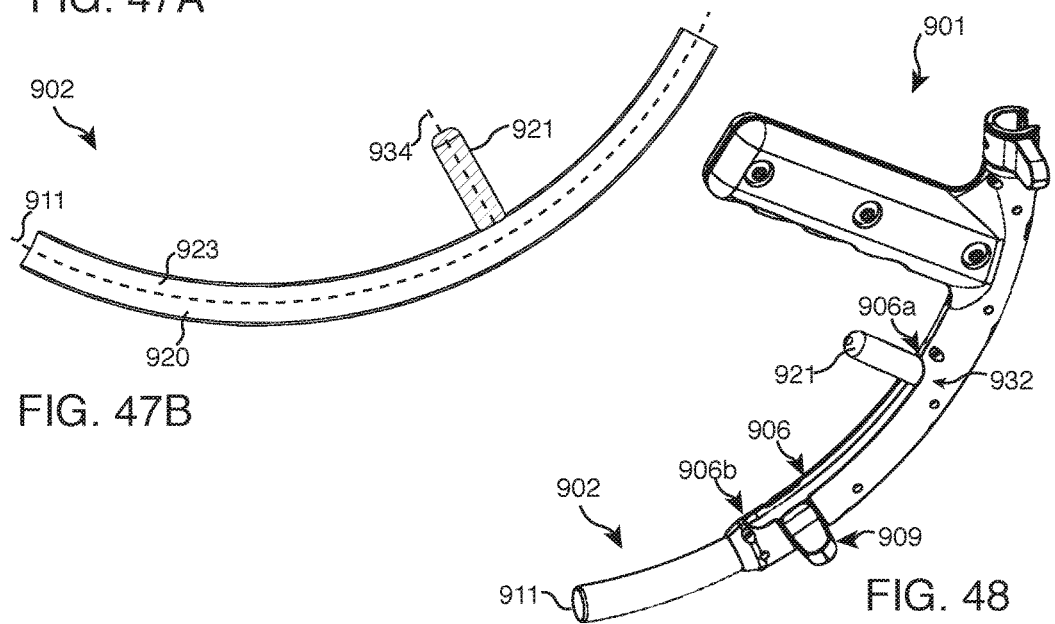
FIG. 47B    FIG. 48

◄ Continued from Fig. 50B

Continued to ► Fig. 50E

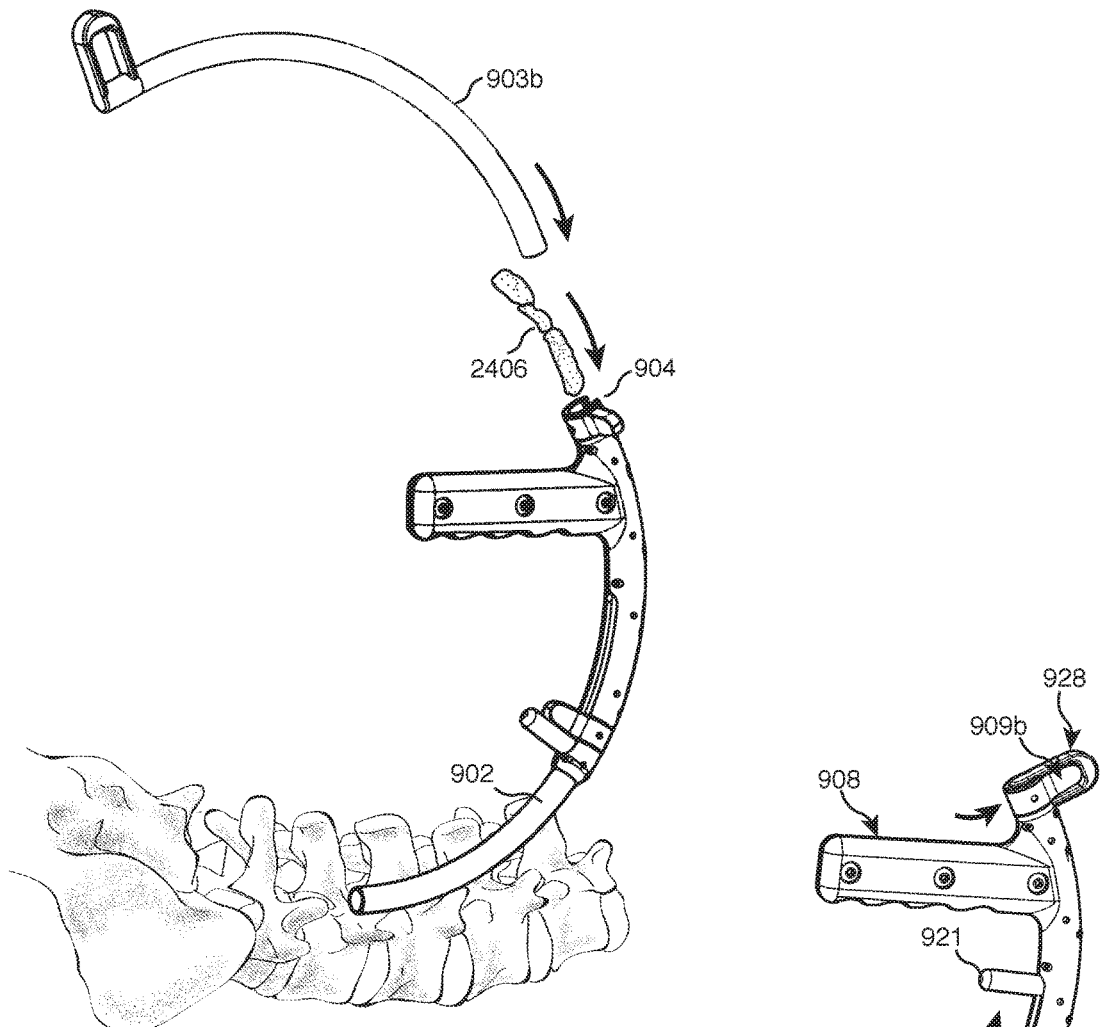
FIG. 50E
FIG. 50F
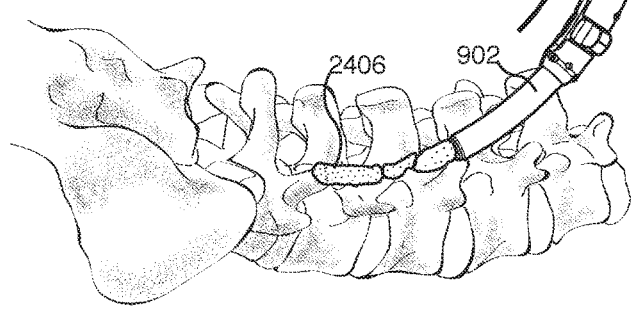
Continued from Fig. 50D

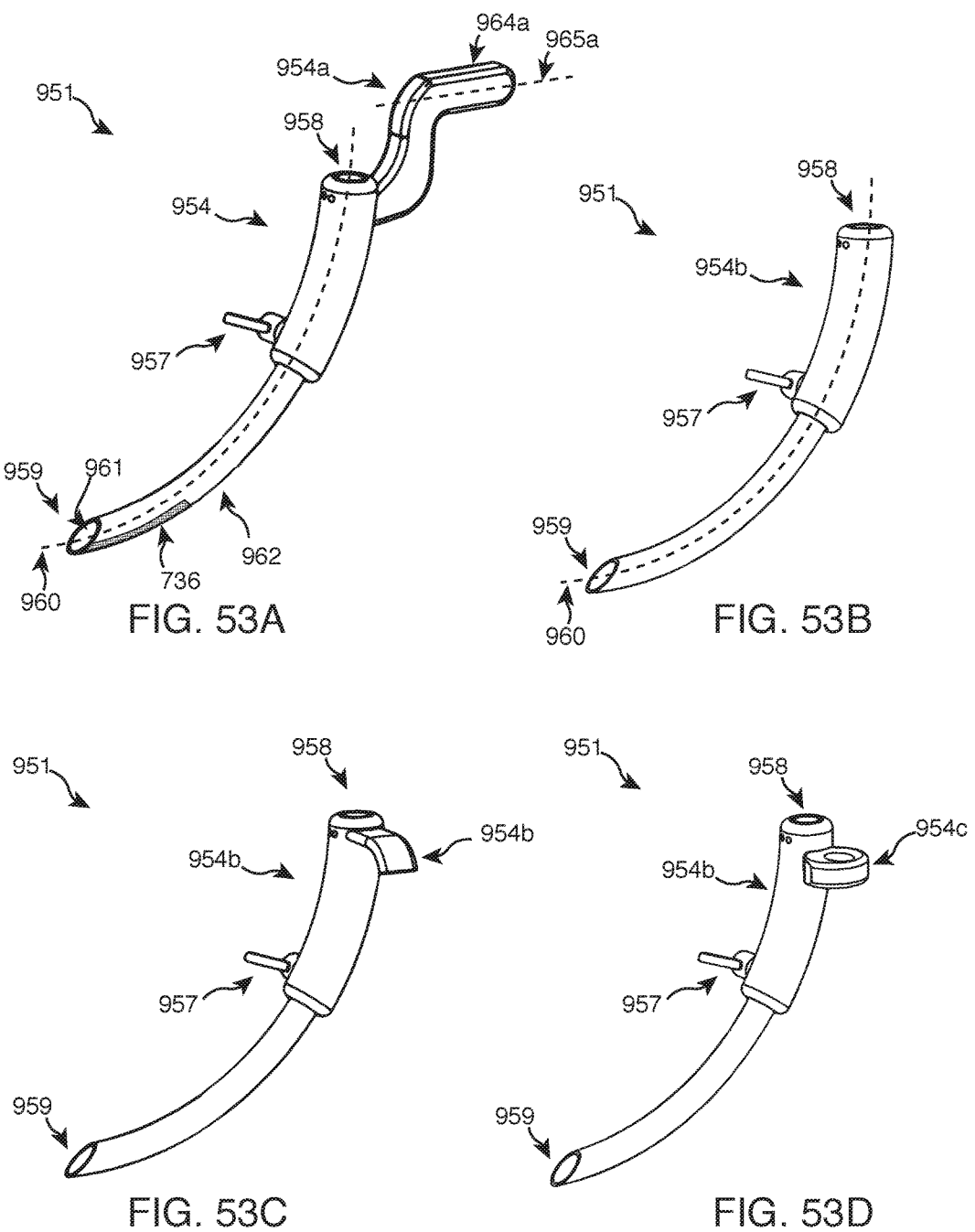

METHOD AND APPARATUS FOR MINIMALLY INVASIVE POSTEROLATERAL SPINAL FUSION

CROSS-REFERENCE TO RELATED APPLICATIONS

This application claims the benefit of U.S. Provisional Patent Application 62/345,667, filed on Jun. 3, 2016, which is hereby incorporated by reference.

BACKGROUND OF THE INVENTION

For the thoracic vertebrae and lumbar vertebrae, a portion of the transverse processes, lamina, pedicles, and vertebral body form a structure called the spinal canal, which protects the spinal nerve. Instability in the spine, such as in the case of spondylolisthesis, can cause nerve irritation and lead to back pain, leg pain, and motor defects. Pain associated with instability in the spine is commonly treated with fusion of adjacent vertebrae. Since the early descriptions of spinal fusions in the early 20$^{th}$ century, advances in spine surgery techniques and devices have allowed more targeted, and less invasive approaches (Albee. 1911. Transplantation of a portion of the tibia into the spine for Pott's disease. A preliminary report. *JAMA.* 57:885; and Hibbs. 1912. A further consideration of an operation for Pott's disease of the spine: with report of cases from the service of the New York orthopaedic hospital. *Ann. Surg.* 55:682.).

Each vertebra has two laterally located structures called transverse processes. A transverse process serves as an attachment point for a number of ligaments and muscle fibers, including, for example, the longissimus muscles, multifidus muscles, rotatores muscles, and levatores costarum muscles. Transverse processes found at the thoracic vertebrae further contain articular facets that are connected to, and serve as attachment points to tubercles of ribs. Using adjacently located transverse processes to place bony material has been described previously.

Traditional lateral intertransverse process fusion, or more commonly referred to as posterolateral fusion procedures or gutter fusion, commonly involves placing bony material along two or more transverse processes of adjacently located vertebrae. There are potential benefits of fusing adjacently located transverse processes to stabilize the spine. Typically, after a period of 6 to 12 months post-surgery, patients undergoing intertransverse process fusion have higher rates of fusion than patients whose spine are secured with screws and rods alone. Such fusion process has been described to consistently have higher fusion rates compared to some other interbody fusion approaches, such as posterior lumbar interbody fusion (PLIF) (Inamdar, et al. 2006. Posterior lumbar interbody fusion versus intertransverse fusion in the treatment of lumbar spondylolisthesis. *J. Ortho. Surg.* 14:21). A typical problem associated with gutter fusions known in the prior art is that such techniques require new or existing (as combined with other surgical procedures) large incisions to perform, incisions which surgeons trained in newer, minimally invasive techniques typically seek to avoid. An unmet need therefore exists to develop instrumentation and tools to allow for a less invasive posterolateral gutter fusion procedure.

Traditional posterolateral fusion procedures, while generally efficacious, have several disadvantages. For instance, in traditional posterolateral fusion procedures, it is common to make a relatively large incision in the posterior region of a patient's back to access and place bony material on and/or between adjacently located transverse processes. Such typical posterolateral fusion procedures can cause great trauma to surrounding tissue and muscle, as such a procedure as known in the prior art involves creating a relatively wide incision to allow access to the transverse process for the placement of bony material. Often, access to transverse processes involves creating a relatively large incision that is approximately 6 inches (15 cm) to 12 inches (30 cm) or more. During creation of such opening to access adjacently located transverse processes, muscle fibers in the vicinity are pulled, split, and tucked. In some cases, muscle fibers are unintentionally, or unavoidably cut. There is also a possibility that blood vessels are cut during such typical posterolateral fusion procedures, leading to the undesirable consequences of interrupted blood supply, possibly slower healing, and a high level of blood loss. The vascularity of the operative area makes traditional posterolateral fusion procedures a procedure associated with a potentially high level of complications (Truchly and Thompson. 1962. Posterolateral Fusion of the Lumbosacral Spine. *J Bone and Joint Surg.* 44-A:505). In some cases, there is a risk of injury to nerves with such large incisions, resulting in nerve damage, decreased sensation during and after surgery, and high levels of post-surgical pain.

In typical posterolateral fusion procedures, once bony material is laid between transverse processes, there is difficulty in keeping bony material in the correct place. Due to the large incision to access the transverse processes, during healing, such bony material may shift or move to other unintended areas. Further, bony material may be placed further anterior, beyond the transverse processes due to, for example, surgeon error and suboptimal surgical technique and instrumentation.

BRIEF SUMMARY OF CERTAIN EMBODIMENTS OF THE INVENTION

Certain embodiments of the invention relate to a minimally invasive surgical procedure to facilitate the fusion of transverse processes. The disclosure herein presents novel approaches for accessing transverse processes of the spine, novel methods for the delivery of fusion material to aid the fusion of said transverse processes, and novel tools to facilitate the procedure in a minimally invasive manner. Certain embodiments of the invention incorporate improved methods for access and treatment, providing a generally less invasive and more efficient procedure than existing surgical methods for fusion of two or more spinal vertebrae at or near the transverse processes. It will be appreciated to those skilled in the art that surgical procedures providing methods that are intended to minimize collateral trauma to tissue and systems of the patient, are generally referred to as "minimally invasive" procedures.

It will be appreciated that embodiments of the invention are performed through a relatively small incision. Access to the transverse process through a small incision allows the surgeon to cause less trauma during the approach. Such access is less invasive and reduces potential damage to muscles or nerves in the vicinity of the spine. Certain embodiments of the invention relate to methods for adding bony material along two or more transverse processes of adjacent vertebrae. In certain embodiments, the methods and apparatuses related to the placement of such bony material in a minimally invasive fashion are novel improvements upon previously known posterolateral fusion procedures.

Certain embodiments are designed for use in conjunction with other spinal fusion procedures. The present inventors have recognized that placement of bony material on the posterior side of the transverse processes often results in better fusion of the vertebrae when combined, for example, with screw and rod systems and/or interbody implants. Certain embodiments include a system, method, or apparatus that facilitate the placement of bony material for fusion of transverse processes. Due to the minimally invasive nature of embodiments of the system and instruments described herein, the procedures can be performed through the same incision or incisions similar to those used for other minimally invasive procedures, such as for example the incision used for the placement of a posterior fixation system, such as a minimally invasive pedicle screw and rod construct. It will be appreciated by those skilled in the art that the fusion of two or more adjacent transverse processes is referred to as an intertransverse process spinal fusion.

Certain embodiments of the invention include access to one or more transverse processes through a posterior-lateral approach, decortication of the one or more transverse processes, further expansion of the path between the one or more transverse processes, and closure of the incision. Certain embodiments include access to the transverse process using an instrument comprising a curved end to access a portion of one or more transverse processes. Certain embodiments include features for decorticating the transverse processes. Additionally, certain embodiments include features for delivery of the bony material.

In certain embodiment of the invention, a graft delivery assembly or tool includes a decorticating surface to decorticate one or more transverse processes in a minimally invasive manner. In certain embodiments, graft delivery assembly is used for decorticating a surface that is perpendicular or near perpendicular to the path of entry. Certain embodiments include a curved element having an abrading surface deployed against a transverse process, where a back-forth motion or rotation of the assembly along its central axis allows bone decortication.

In certain embodiments, a decortication feature accesses and decorticates a surface of a transverse process at an approach angle that is substantially perpendicular. In certain embodiments, an angled tool assembly is used to decorticate a transverse process through an approach path that is not perpendicular (i.e. 90° or less).

Certain embodiments include using a distending feature to place bony material in the space between the transverse processes. In certain embodiments, one end of a distending device associated with the invention is filled with bony material. In such a device, the distending device subsequently deposits bony material between at least a first transverse process and a second transverse process during the associated surgical procedure.

In certain embodiments, the surgical approach to accomplish placement of bony material across and between adjacent transverse processes is accomplished through a generally curved pathway. In certain embodiments, the space between transverse processes is first accessed with a curved needle. In other embodiments of the invention, the apparatuses allow for the procedure to take place without first placing a needle to define the path. In certain embodiments dilators matching the diameter of such curved needle expand a pathway to the transverse processes.

Certain embodiments incorporate steps to define an access portal by way of associated instrumentation. A user may generally insert instruments, devices, tools, bony material, and the like through an access portal or a dilator. In certain embodiments, decortication tools, including, but not limited to a cutter assembly, rasps, files, and drills are used to decorticate the surface of the transverse processes through an access portal or a dilator. Furthermore, in certain embodiments, bony material is deposited between transverse processes through a generally curved pathway.

In certain embodiments, bony material is delivered to at least a first transverse process, an intertransverse space, and a second transverse process using a graft delivery assembly or tool. In certain embodiments, a graft delivery assembly or tool itself is used to create a path to the transverse process through an incision. In certain embodiments, a graft delivery assembly or tool is used to deliver bony material on at least one transverse process surface. In certain embodiments, a graft delivery assembly or tool incorporates a rasp-like feature on the side intended to directly contact the transverse process to decorticate the bone surface of one or more transverse processes. Certain embodiments use a graft delivery tool to open a path and deliver bony material to a surgical site. Certain embodiments of a graft delivery tool include a handle, a first segment, and a second segment. In certain embodiments, a graft delivery tool having a solid profile may be used by a practitioner to create a pathway from the exterior of the body to the transverse processes through an incision of the skin. In certain use cases, a graft delivery tool having a solid profile may be inserted to create a pathway to the intertransverse space after performing a pedicle screw/rod fixation procedure, optionally through the same incision used for the pedicle screw/rod fixation procedure. Certain embodiments allow placement of bony material across two or more transverse processes. In certain embodiments, a graft delivery tool has an abrading surface that allows decortication of a bone surface.

In certain embodiments, a graft delivery assembly or tool may have pre-loaded bony material. Pre-loaded bony material may be placed within the graft delivery assembly or tool prior to the step utilizing the graft delivery tool during the surgical procedure. The graft delivery assembly or tool containing pre-loaded bony material may be subsequently inserted through a minimally invasive incision and then along a path that allows for placement of the pre-loaded bony material in proximity or in contact with two or more adjacent transverses processes. In an embodiment of the graft delivery assembly tool, a shaft or sheath may be retracted back through the pathway while the plunger of the embodiment forces the bony material outward, depositing the bony material across and between the at least two transverse processes as the graft delivery assembly or tool retracts. In embodiments of the graft delivery assembly or a plunger stays in a generally stationary position while the user of the embodiment retracts the shaft or sheath using a trigger-like handle over the plunger to deposit the bony material. In certain embodiments, a graft delivery assembly or tool with a hollow profile has a ratcheting device. In certain embodiments, a graft delivery tool with hollow profile comprises a thumb-wheel device further comprising a thumb-wheel. A user may rotate the thumb-wheel in a first direction to extend a plunger head in a distal direction to dispense loaded bony material in a second direction to retract the plunger head in a proximal direction. In certain embodiments, a graft delivery tool with a hollow profile incorporates an outer sleeve that is connected to a sleeve handle, which a surgeon may utilize to pull back the outer sleeve and thereby deposit bony material after retraction. The retraction of the plunger head may be desired to allow a practitioner to load bony material into the graft delivery tool for successive bony material depositions.

Certain embodiments of the invention include a graft delivery assembly, which further includes a graft delivery shaft and a curved element. A curved element may come in the form of a sheath or a rod. Certain embodiments of the invention include a graft delivery assembly, which further includes a delivery shaft, delivery sheath, and at least one curved rod. Certain embodiments of a delivery shaft have a tool insertion end and a graft delivery end. A delivery shaft generally follows a central axis, and further has a shaft pathway that follows the central axis, and is communicably connects the tool insertion end and a graft delivery end. In certain embodiments, a central axis includes a curvature, where generally, the curvature closely aligns with the lordotic curvature of certain regions of the spine. The shaft pathway generally allows passage of other instruments, such as curved elements including a delivery sheath and a curved rod, bony material, or other objects described herein or elsewhere relevant to surgical procedures.

Certain embodiments of a graft delivery shaft include a small longitudinal opening that communicates with the shaft pathway. Such small longitudinal opening slideably guides a protrusion or a jut (such jut being able to work as a handle) of a delivery sheath or a curved rod. Certain embodiments of a delivery shaft also include a handle for easier handling. Certain embodiments of a delivery shaft also include ventilation holes allowing sterilization of the assembly. In certain embodiments, a delivery shaft is a unibody assembly, or two-mating pieces assembled and optionally fastened with fasteners to allow easier assembly.

In certain embodiments, a delivery shaft includes a retention lock that restricts movement of either a delivery sheath or a curved rod relative to the delivery shaft. In certain embodiments, a retention lock has a mechanism to restrict movement of an instrument (including delivery sheath, curved rod, or other instruments) from sliding through a shaft pathway. In certain embodiments, a retention lock is radially actuated and rotates 90°.

In certain embodiments, a graft delivery assembly includes a curved element, such as a sheath. An embodiment of a sheath has a first end and second end, with a sheath pathway generally following the central axis and being in communication with the first end and second end. The sheath pathway generally allows passage of other instruments, curved elements, and the like, such as curved rod, bony material, or other objects described herein or elsewhere relevant to surgical procedures. In certain embodiments, the sheath pathway further defines an exterior surface and an interior surface. The delivery sheath exterior surface has a protrusion or jut in certain embodiments. When installed in a delivery shaft, the delivery sheath slides through the shaft pathway.

Embodiments of a graft delivery assembly also include a curved element such as a curved rod. In certain embodiments, a curved rod is further defined as a decorticating rod and/or as a plunging rod. A curved rod is generally aligned with a central axis, and is further defined by a first end and a second end. Certain embodiments of a decorticating rod have an abrading surface allowing decortication of bone surfaces. Certain embodiments of a curved rod have beveled end, allowing separation of tissue in an atraumatic fashion as the assembly is inserted into the body. In certain embodiments, a plunging rod has a surface that allows pushing bone graft to the surgical site. In one example, a curved rod has a blunt end. Together, by controlling the timing of the locking and unlocking of the retention lock or a plurality of retention locks, the graft delivery assembly in certain embodiments allows for targeted delivery of graft material to the transverse processes.

BRIEF DESCRIPTION OF THE DRAWINGS

FIG. 2A. A flow diagram of specific exemplary steps to fuse adjacently located vertebrae in certain embodiments of the invention.

FIG. 2B. A flow diagram of specific exemplary steps to fuse adjacently located vertebrae in certain embodiments of the invention.

FIG. 14. A cutter assembly in certain embodiments of the invention.

FIG. 15. A cutter blade in certain embodiments of the invention.

FIG. 34A. Side view of an embodiment of a graft delivery tool.

FIG. 34B. Side view of embodiments of a graft delivery tool comprising a surface to facilitate decortication.

FIG. 34C. Side view of an embodiment of a graft delivery tool.

FIG. 34D. A lateral view of an exemplary spine showing an approach path for fusion of a right transverse process of L3 and right transverse process of L4, in certain embodiments of the invention.

FIG. 34E. A lateral view of an exemplary spine showing a graft delivery tool spanning two adjacent transverse processes.

FIG. 34F. A lateral view of an exemplary spine showing a graft delivery tool spanning three adjacent transverse processes.

FIG. 35. Side view of an embodiment of a graft delivery tool comprising a plunger.

FIG. 36A. An embodiment of a cross-section found on a graft delivery tool.

FIG. 36B. An embodiment of a cross-section found on a graft delivery tool.

FIG. 36C. An embodiment of a cross-section found on a graft delivery tool.

FIG. 36D. An embodiment of a cross-section found on a graft delivery tool.

FIG. 36E. An embodiment of a cross-section found on a graft delivery tool.

FIG. 36F. An embodiment of a cross-section found on a graft delivery tool.

FIG. 37A. A pointed tip found on a graft delivery tool, in certain embodiments.

FIG. 37B. A round tip found on a graft delivery tool, in certain embodiments.

FIG. 37C. A blunt tip found on a graft delivery tool, in certain embodiments.

FIG. 38A. An embodiment of a graft delivery tool comprising a surface with knurling.

FIG. 38B. An embodiment of a graft delivery tool comprising surfaces with knurling FIG. 38C. An embodiment of a graft delivery tool comprising surfaces with splines.

FIG. 38D. An embodiment of a graft delivery tool comprising knurling and splines.

FIG. 39. An embodiment of notches, in certain embodiments of the invention.

FIG. 40. An embodiment of a graft delivery tool.

FIG. 41A. An embodiment of a graft delivery tool.

FIG. 41B. A sectional view of a graft delivery tool embodiment.

FIG. 42. A graft delivery tool comprising a curved dilator in certain embodiments.

FIG. 45A. Side view of a retention lock embodiment.

FIG. 45B. Perspective view of a retention lock embodiment.

FIG. 46. Perspective view of a delivery shaft with a retention lock hidden in certain embodiments.

FIG. 47A. Side view of a delivery sheath in certain embodiments.

FIG. 47B. Cross-sectional view of a delivery shaft in certain embodiments.

FIG. 48. Perspective view of a delivery sheath inside a delivery shaft in certain embodiments.

FIG. 50E. Representative view of a graft delivery assembly in use.

FIG. 50F. Representative view of a graft delivery assembly in use.

FIG. 53A. A graft delivery sheath in certain embodiments.

FIG. 53B. A graft delivery sheath in certain embodiments.

FIG. 53C. A graft delivery sheath in certain embodiments.

FIG. 53D. A graft delivery sheath in certain embodiments.

DETAILED DESCRIPTION OF CERTAIN EMBODIMENTS

Figure 1:
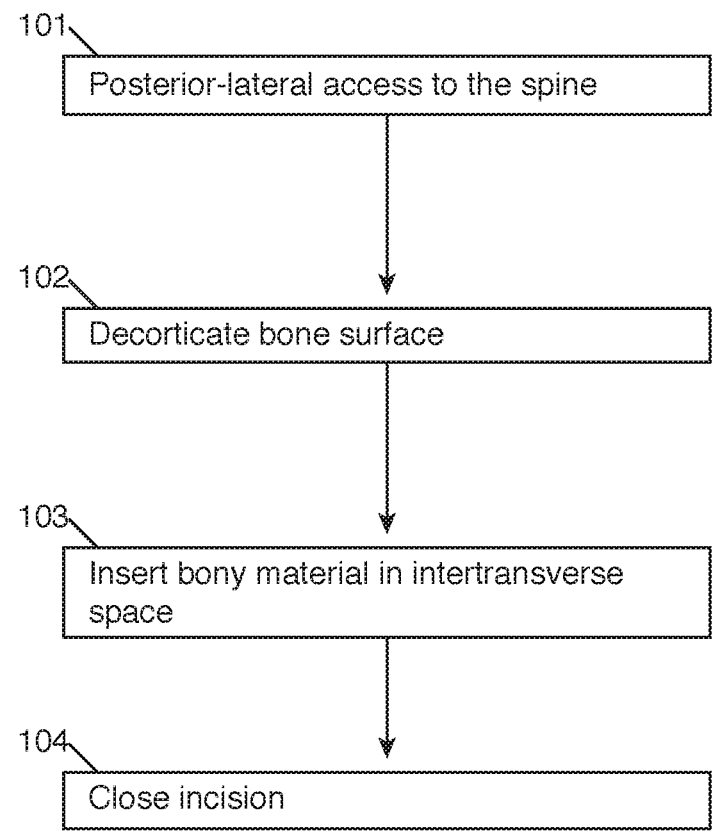
FIG. 1. A flow diagram of steps to fuse adjacently located vertebrae in certain embodiments of the invention.

Disclosed herein are embodiments of a surgical method and apparatuses associated with a minimally invasive approach for the percutaneous placement of bone graft material over and between the transverse processes in association with surgical procedures involving the spine. There are a number of advantages associated with the minimally invasive approach to fusing transverse processes, as described below and defined herein. Included in such certain embodiments are tools, tool assemblies, and components to facilitate such surgical approach. Other systems, methods, features, and advantages of the invention will be or will become apparent to one with skill in the art upon examination of the figures incorporated herein, and detailed description. It is intended that all such additional systems, methods, features, and advantages included within this description be within the scope of the invention and be protected by the accompanying claims. It will be appreciated that certain steps are designed to place bony material in contact with at least two or more transverse processes and the intertransverse process space in a less invasive or minimally invasive way. Less invasive or minimally invasive, as referred to herein, typically describes performing surgery that may be accomplished percutaneously and/or through small incisions and that results in decreased complications, blood loss, scarring, and the like.

In general, certain embodiments of the invention are performed by a medical practitioner, where such medical practitioner may include any of a number of entities related to a surgical procedure, including but not limited to surgeons, physician's assistants, nurses, technicians, neurodiagnostic technicians, surgical robots and/or anesthesiologists. Certain embodiments of the invention are performed in conjunction with a number of instruments, including, but not limited to imaging or scanning devices such as, for example, biplanar fluoroscopes (also referred to as C-Arm fluoroscopes). Such imaging or scanning devices captures images of a patient through various views, including but not limited to a lateral view, an oblique view, a posterior and anterior-posterior (AP) view, superior view, and distal views of the patient. Such imaging or scanning devices are used in portions of, or throughout the entirety of, surgical procedures described in certain embodiments of the invention. The present inventors contemplate that such imaging and scanning devices may assist medical practitioners in the proper placement and intended use of the embodiments of the apparatuses and methods described herein.

In general, the surgical approaches associated with certain embodiments of the invention occur after a patient undergoes local or general anesthesia, disinfection, and other standard procedures and practices related to surgery and/or spinal surgeries known to persons having ordinary skill in the art. In certain embodiments of the invention, a patient is optionally placed under general anesthesia, remains conscious, and/or otherwise is placed under a general or local analgesic for the duration of the methods and procedures described. In certain embodiments, the surgical approach is performed on a patient placed in a prone position. The inventors have recognized that an advantage associated with embodiments of the methods and apparatuses associated with the invention is that in certain circumstances, local anesthesia may be used which generally presents less risk to the patient than general anesthesia.

Certain embodiments of the invention relate to methods for adding bony material along two or more transverse processes of adjacent vertebrae. The methods and apparatuses associated with the embodiments described herein related to the placement of bony material in proximity to and directly upon one or more transverse processes are novel improvements upon common posterolateral fusion procedures that solve previously unsolved problems.

As used herein, the term "bony material" may refer to morselized autograft, allograft bone, and/or bone matter such as demineralized bone matrix (DMB). The term "bony material" may also refer to substitutes such as bone glues, materials organic, inorganic, synthetic, and natural, as well as bone morphogenetic proteins, stem cells, amniotic membrane, collagen and collagen derivative preparations, and other compounds and materials promoting bone growth such as bone morphogenic protein (BMP) in certain embodiments. In certain embodiments, the term "bony material" may refer to allograft bone material that is preformed to facilitate its insertion into the body. In certain embodiments, the term "bony material" may refer to other materials that may be implanted in association with generally known spinal fusion procedures including those other than procedures described herein, which may include metals, including, but not limited to, biocompatible metals and alloys, such as titanium, tantalum, stainless steels, gold, silver, cobalt, chromium, platinum, ruthenium, rhodium, rhenium, and other alloys thereof, combinations thereof, and/or other equivalent material intended to bridge two or more transverse processes through utilization of the method steps and apparatuses disclosed herein. In certain embodiments, the term "bony material" may refer to polymers, including, but not limited to polymethyl methacrylate (PMMA), polyetheretherketone (PEEK), polymethymethacrylate (PMMA), polyglycolic acid and/or polylactic acid compounds, polystyrene (PS), polyesters (PET, polycaprolacton, polyglycolied, poylactide, poly-p-dixanone, poly-hydroxybutylate), polyvinylchloride (PVC), polyethylene (PE, HDPE, UHMWPE, etc.), polyamides (Nylons, aromatic polyamides), polypropylene (PP), fluorocarbon polymers (PTFE, PTFCE, PVF, FEP) and/or other biocompatible materials.

Referring to a flow chart on FIG. 1 describing steps found in certain embodiments, the surgical procedures that are performed using instruments, implants, devices, and bony material include but are not limited to one or more of: (1) posterior-lateral access to the spine, step 101; (2) decorticate bone surface, step 102; (3) insert bony material in intertransverse space, step 103; and (4) close incision, step 104.

In certain embodiments, fusion of the intertransverse process further includes specific steps as shown in FIG. 2A-B. Referring to FIG. 2A, such surgical procedures that are performed during certain embodiments include: (1) make an incision, step 201; (2) insert cannulated needle, step 202; (3) insert guide wire, step 203; (4) insert dilator, step 204; (5) insert larger dilators and dilate path, step 205; (6) insert decortication tool, step 206; (7) decorticate transverse processes step 207; (8) insert bony material into intertransverse process path, step 208; and (9) suture incision, step 209. In the preferred embodiment of the invention, the steps associated with inserting dilators and guide wires are further streamlined by the design of a graft delivery assembly, as shown for example in FIGS. 43-53. Such streamlined steps may include: (1) make an incision, step 211; (2) insert a graft delivery assembly, step 212; (3) decorticate transverse process, step 213; (4) insert bony material into intertransverse space, step 214; and (5) suture incision, step 215. In certain embodiments, a graft delivery assembly provides an all-in-one solution to perform steps 212, 213, 214.

Figure 3:
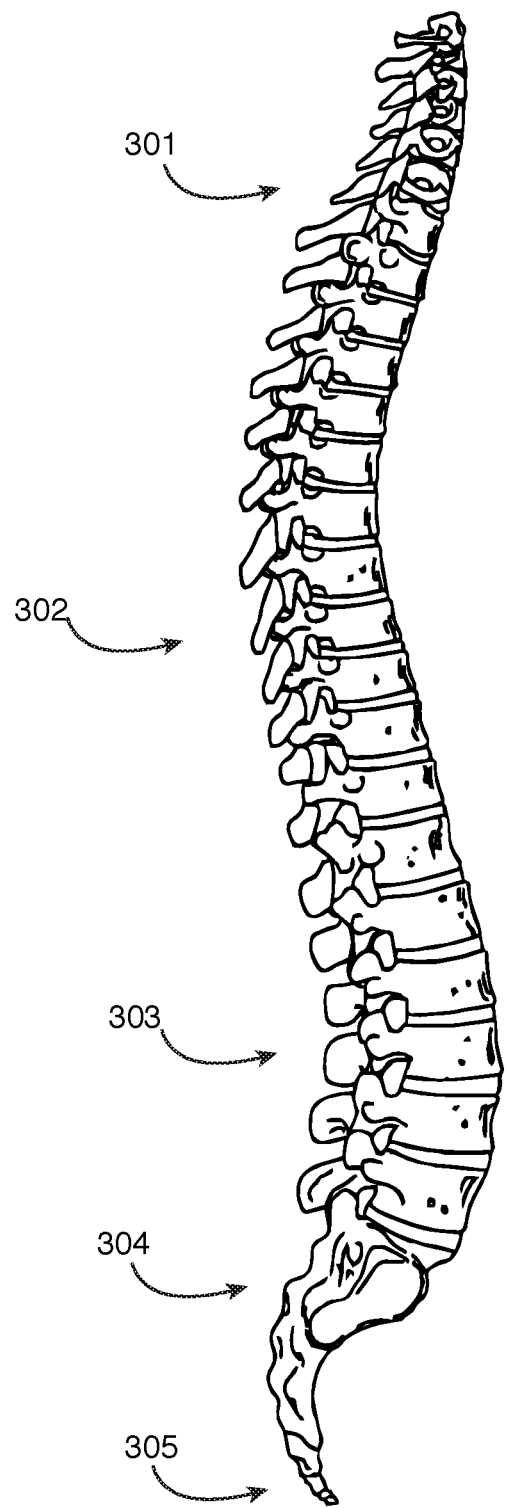
FIG. 3. A lateral view of an exemplary spine.
Figure 4:
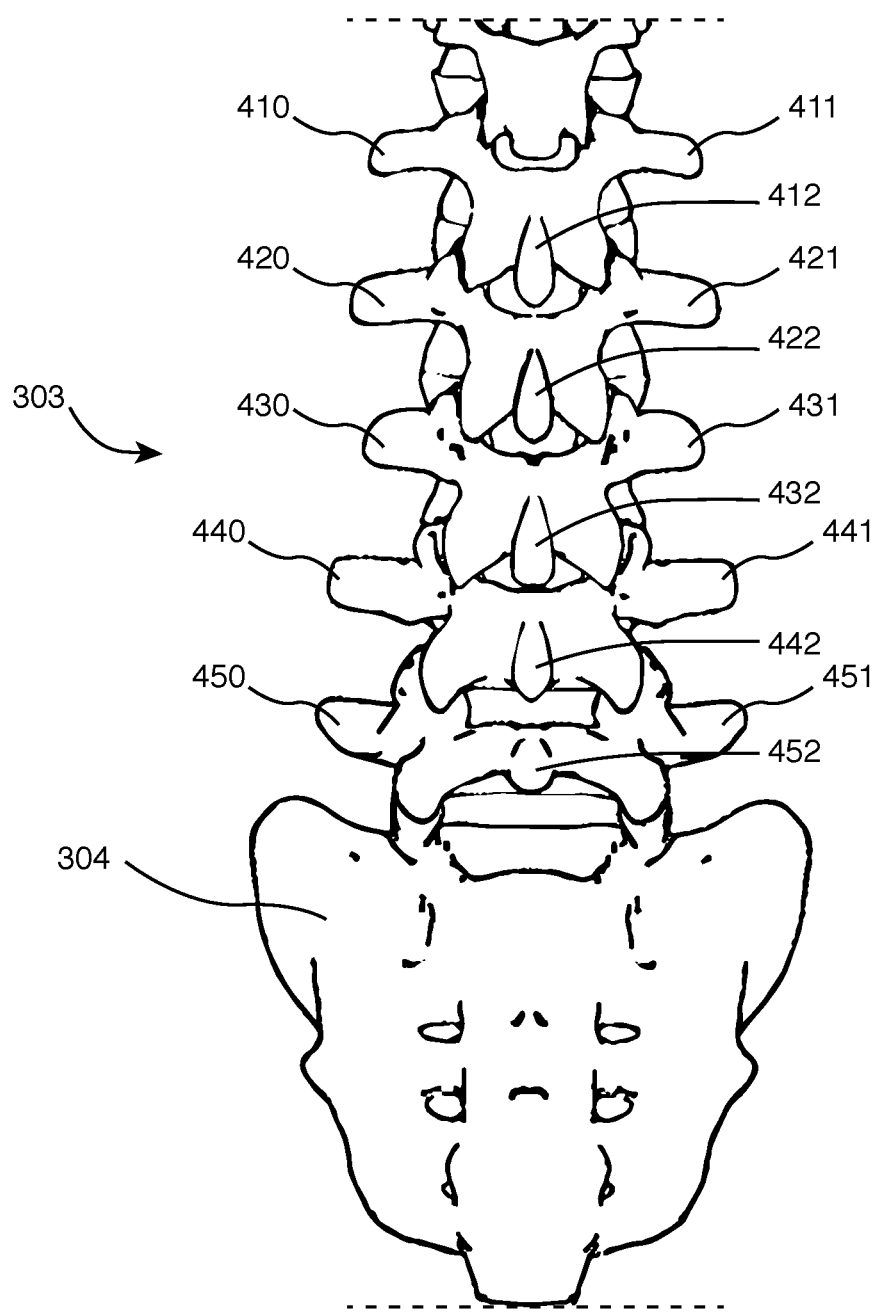
FIG. 4. A posterior view of an exemplary spine, including the lumbar vertebrae and sacrum.
Figure 5:
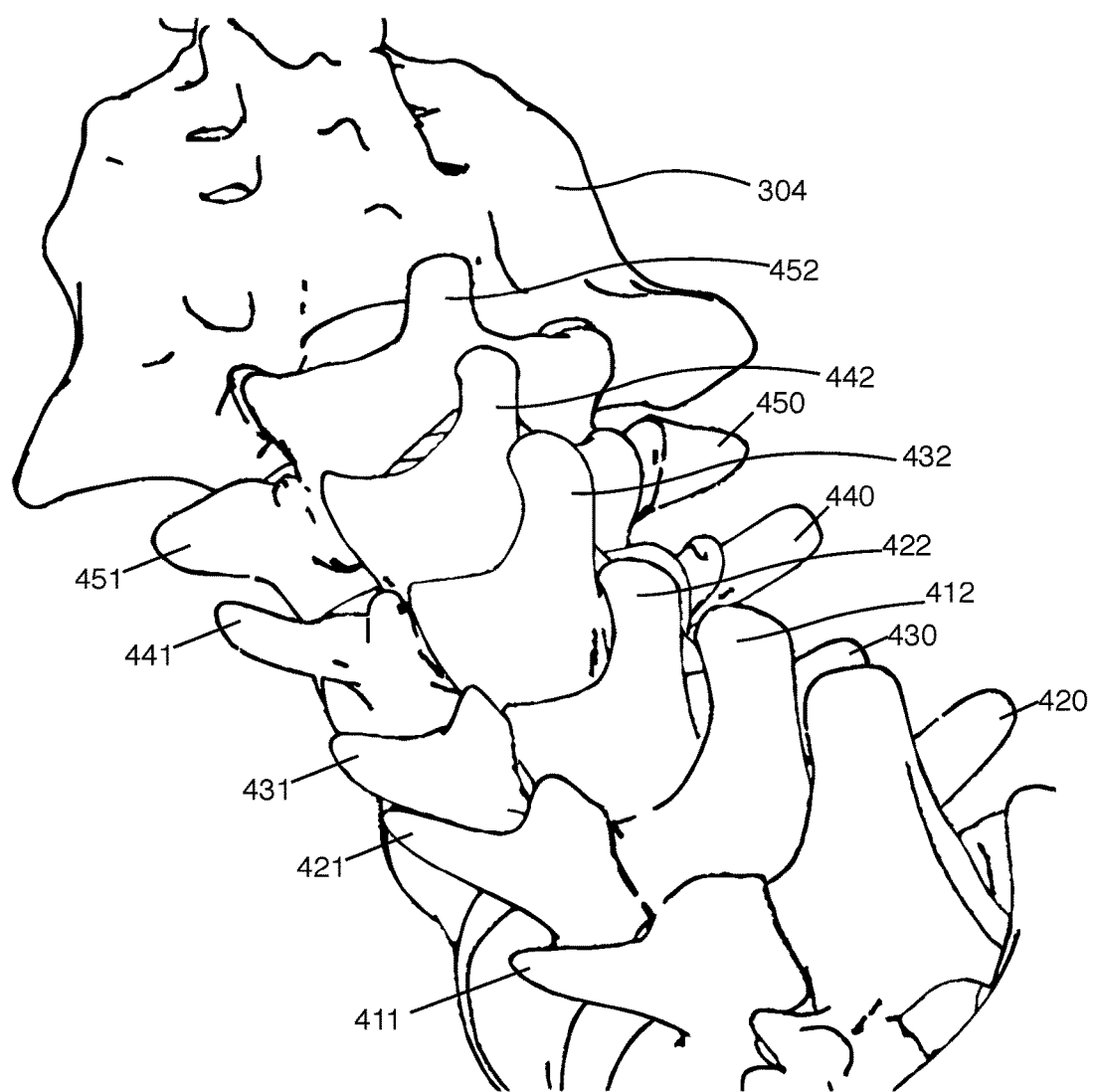
FIG. 5. Superior-Posterolateral view of an exemplary spine, including the lumbar vertebrae and sacrum.

The general anatomical structures that are considered during the surgical procedures of certain embodiments include, but are not limited to, the transverse processes. In certain embodiments, a fusion of transverse processes can be accomplished between transverse processes in the lumbar vertebrae. It can be appreciated by those skilled in the art that fusion of such transverse processes is not limited to the lumbar vertebrae, as vertebrae in other regions of the spine, for instance, the thoracic vertebrae 302, or cervical vertebrae 301, as shown in FIG. 3, may be fused with certain embodiments of the invention. The present inventors contemplate that size variations of the apparatuses described herein, including related to the radius of the curvature of the bone graft inserter and/or the diameter of the associated sheath, may be necessary to specifically accommodate the various dimensions of the different regions of the spine. Referring to FIG. 3, and further shown for example in FIG. 4, FIG. 5, FIG. 6A, FIG. 6B, FIG. 7A, FIG. 7B, and FIG. 8, the lumbar vertebrae 303, the sacrum 304 and coccyx 305 are shown as reference to better understand certain embodiments. In order to better understand certain embodiments of the invention, certain figures including but not limited to FIG. 4, FIG. 5, FIG. 6A, FIG. 6B, FIG. 7A, FIG. 7B, FIG. 8, FIG. 11, FIG. 12, FIG. 13A, FIG. 13B, FIG. 19, FIG. 21, FIG. 27, and FIG. 29, may show the following structures: left 410 and right 411 transverse processes of the L1 vertebra; left 420 and right 421 transverse processes of the L2 vertebra; left 430 and right 431 transverse processes of the L3 vertebra; left 440 and right 441 transverse processes of the L4 vertebra; left 450 and right 451 transverse processes of the L5 vertebra; the L1 spinous process 412; L2 spinous process 422; L3 spinous process 432; L4 spinous process 442; L5 spinous process 452; and sacrum 304.

Figure 6A:
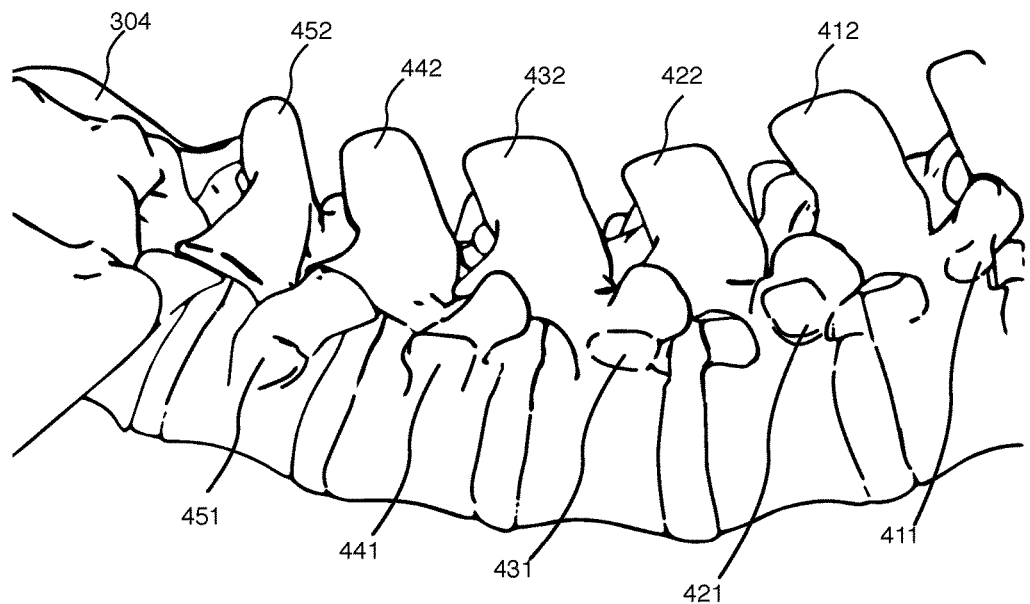
FIG. 6A. A lateral view of an exemplary spine.
Figure 6B:
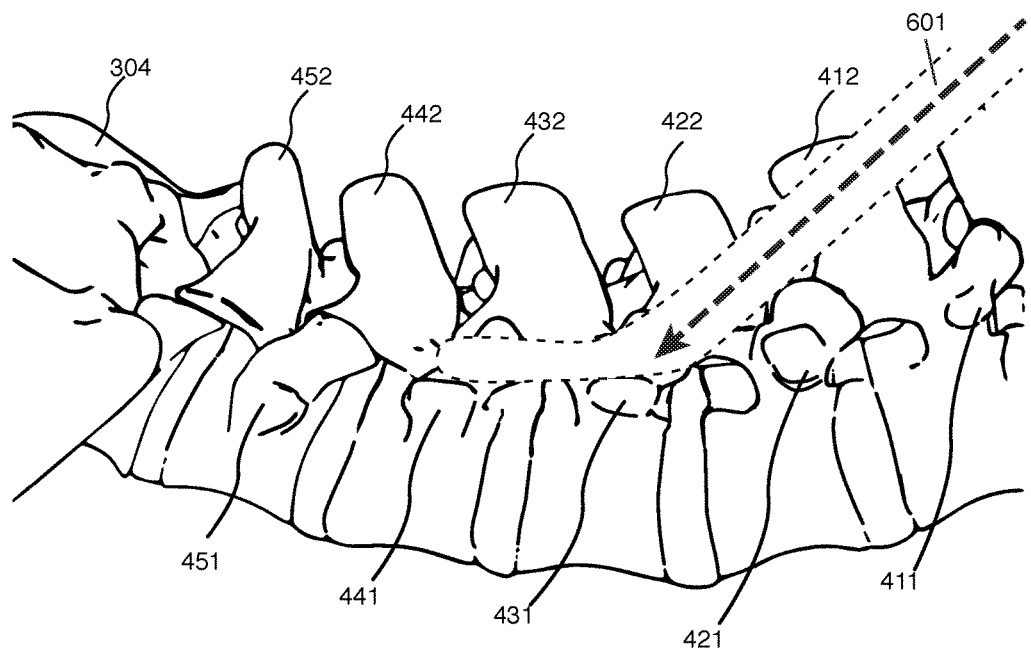
FIG. 6B. A lateral view of an exemplary spine showing an approach path for fusion of a right transverse process of L3 and right transverse process of L4 in certain embodiments of the invention.
Figure 7A:
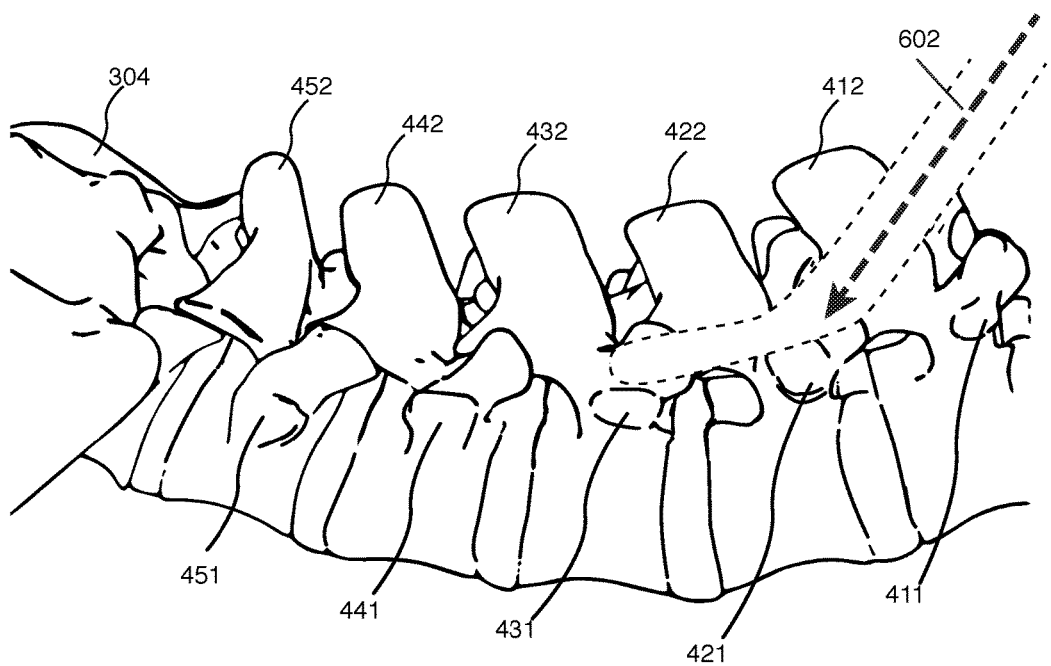
FIG. 7A. A lateral view of an exemplary spine showing an approach path for fusion of a right transverse process of L2 and right transverse process of L3 in certain embodiments of the invention.
Figure 7B:
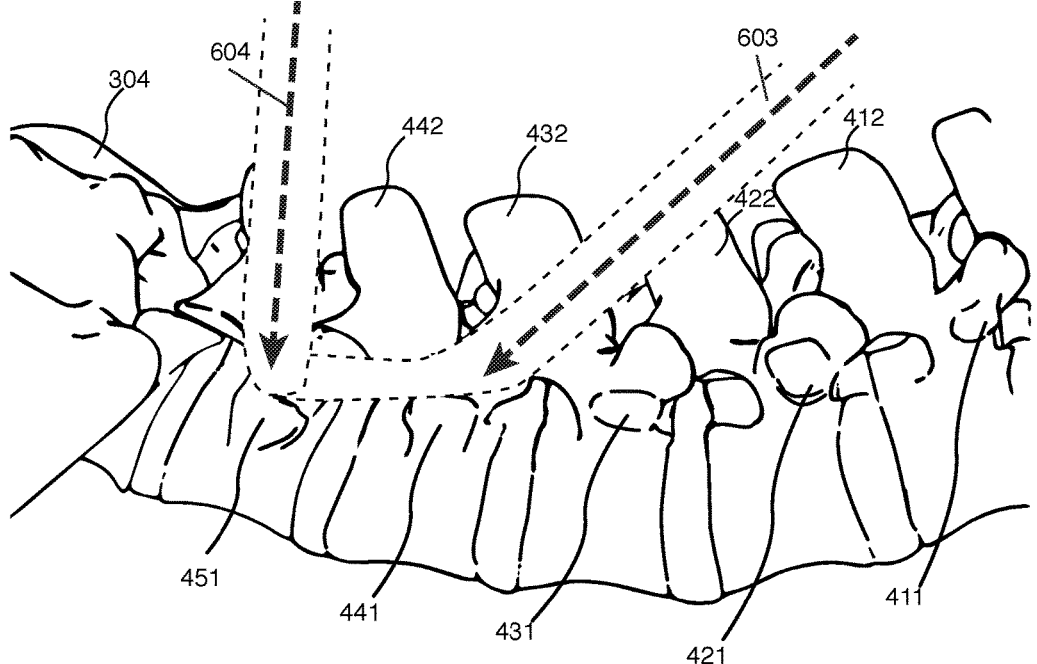
FIG. 7B. A lateral view of an exemplary spine showing an approach path for fusion of a right transverse process of L4 and right transverse process of L5 in certain embodiments of the invention.

Referring to FIG. 6B, in certain embodiments, access to the transverse processes is accomplished with an approach path 601 that is generally from a superior and posterior position, in a direction that is generally caudal and anterior. Still referring to FIG. 6B, such approach path 601 allows access to the L3 right transverse processes 431, and the L4 right transverse process 441 in certain embodiments. In certain embodiment, other approach paths that are further superior or inferior may be used to target other transverse processes. For example, as shown in FIG. 7A, an approach path 602 allows access to the L2 right transverse processes 421 and the L3 right transverse process 431. In another example, referring to FIG. 7B, in certain embodiments, two approach paths are used for fusing two adjacent transverse processes, where an superior-posterior approach path 603 allows access to the L4 right transverse processes 441 and the L5 right transverse process 451, and posterior approach path 604 accesses the right L5 transverse process 451. In certain embodiments, fusion of two or more adjacent transverse processes involves one approach path 602, as shown in an embodiment in FIG. 7A. In certain embodiments, fusion of two or more adjacent transverse processes involves two unique approach paths 603, 604, as shown in an embodiment in FIG. 7B. It will be appreciated that approach paths can be established at different vertebral designated levels along the posterior of the patient to access transverse processes. In certain embodiments, approach paths can be created on both sides of the spine to allow for placement of bony material over and between adjacent transverse processes located on both hemispheres of the spine. It will also be appreciated that in varying embodiments of the invention, the placement of bony material over and between adjacent transverse processes fusion of transverse processes is not limited to fusion of transverse processes of only two vertebrae and may be applied in alternate situations where the fusion of adjacent bone structures is desired. In certain embodiments more than two transverse processes may be fused.

Figure 8:
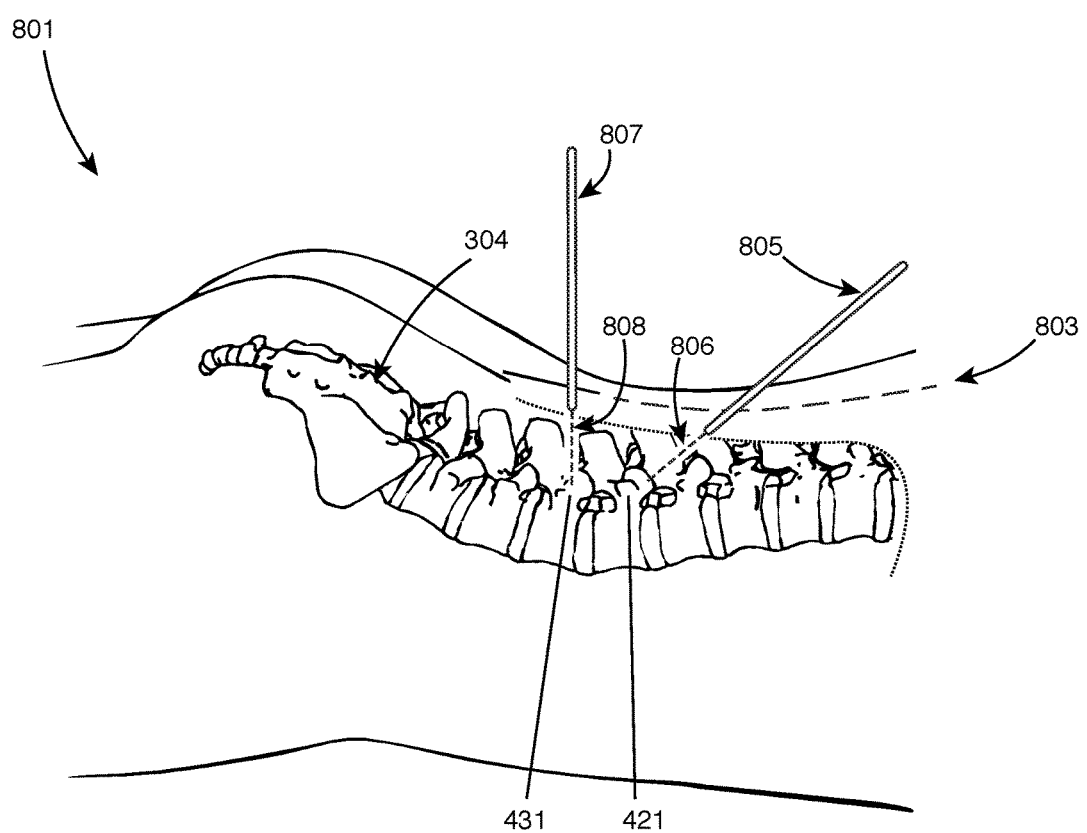
FIG. 8. A lateral, perspective view of a patient with a portion of a spine shown to demonstrate a radio-dense object placed on an exterior surface of a patient's spine, and predicting a straight line from such radio-dense object to a transverse process, in steps in certain embodiments of the invention.

Once a medical practitioner diagnoses and determines the vertebrae requiring fusion, a patient 801 (for example, shown in FIG. 8) and the devices are readied for the surgical procedure. In certain embodiments, the make an incision step 201, 211 shown in FIG. 2A-B includes the preparation for marking, and creating an incision in the patient providing access to the spine. Prior to making an incision, a medical practitioner may place a long radio-dense object 805, such as a wire, on an exterior surface of the skin. A medical practitioner may reference images from a bone-imaging device such as a C-Arm Fluoroscope to provide views such as a lateral view of a patient laying in a prone position, as shown in FIG. 8. The images generated by the bone-imaging device allow a medical practitioner to envision a predicted trajectory 806 to certain regions of the spine. If a predicted trajectory does not allow access to the desired transverse processes requiring fusion, the angle or the location of a radio-dense object may be adjusted and reassessed with a bone-imaging device, until an appropriate angle or path prediction is achieved prior to marking the point of incision on the patient's skin. In certain embodiments, a predicted trajectory 806 of a radio-dense object 805 predicts a transverse process 421 of L2 as shown in FIG. 8. Still referring to FIG. 8, in certain embodiments, another angle or path is established. A medical practitioner may place a second oblong radio-dense object 807 on an exterior surface of the skin. A predicted trajectory 808 of such radio-dense object 807 predicts a path reaching an adjacent transverse process 431 of L3. In this example, the approach paths allow fusion of transverse process of L2 421 and L3 431. It will be appreciated that depending on the transverse processes that require fusion, a medical practitioner may adjust the mark on the skin of the patient 801 more rostral or more caudal in reference to the spine, or either to the left or to the right of a midline 803 of a patient's spine.

Figure 9:
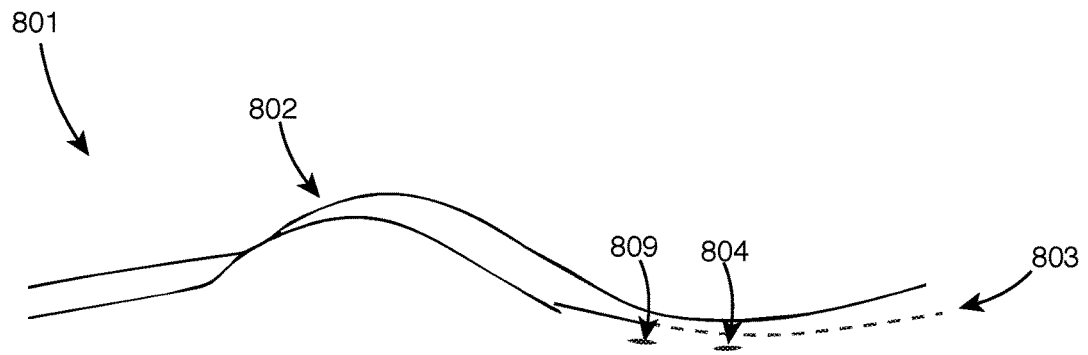
FIG. 9. A perspective view of a patient with incisions corresponding to steps in certain embodiments of the invention.
Figure 10:
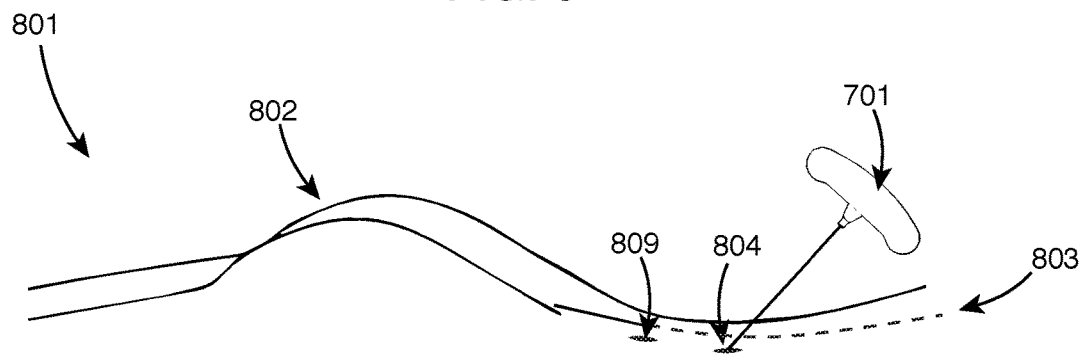
FIG. 10. A lateral, perspective view of a needle insertion, corresponding to certain steps in embodiments of the invention.

Referring again to FIG. 8, once an appropriate angle or path is determined, a medical practitioner may refer to the tip of a radio-dense object 805, 807 that is in contact with the skin surface of the patient 801 to mark a region on a patient's back. Such a mark, made with a pen, marker, or other marking tool, gives a medical practitioner a reference region to create an initial incision on a patient's back. It will be appreciated that embodiments of the invention are performed through a relatively small incision, as to perform a minimally invasive surgery. In certain embodiments, as shown in FIG. 9, FIG. 10, FIG. 11, FIG. 12, FIG. 13A, and FIG. 13B, an incision 804, 809 to the right of a midline 803 (and/or to the left of a midline in an embodiment of fusion where appropriate) is created with an incision tool such as a scalpel. As shown in FIG. 9, and FIG. 10, a patient's buttocks 802 are shown as a reference point. An incision allows access by instruments, and/or devices that are related to certain embodiments into the soft tissue and muscle of the patient 801 providing access to the spinal structure. It will be appreciated that a number of the following steps described herein may be performed through both incisions 804 and 809 during certain embodiments of the surgical procedure. In certain embodiments, it is advantageous to access a pair of transverse processes from separate approach paths. Through these separate approach paths, the steps of (1) posterior access to the spine, step 101; (2) decorticate bone surface, step 102; and (3) insert bony material in intertransverse space, step 103; shown in FIG. 1 are performed.

Decortication of such surfaces is not limited to the instruments as shown in the examples provided, as other instruments may be used in embodiments of the surgical procedure described. The decorticate bone surface, step 102, as shown in FIG. 1, may include further preparation of the bone surfaces for bone fusion, such as shaping such surfaces with a bone rasp. Removal of biological material from surfaces may be accomplished through the use of instruments including, curettes, dissectors, rasps, probes, burrs, rongeurs, or forceps through a dilator. In the preferred embodiment of the invention, the surface of the graft delivery tool most proximal to the transverse processes incorporates an abrading surface, as depicted in FIG. 43B.

Figure 11:
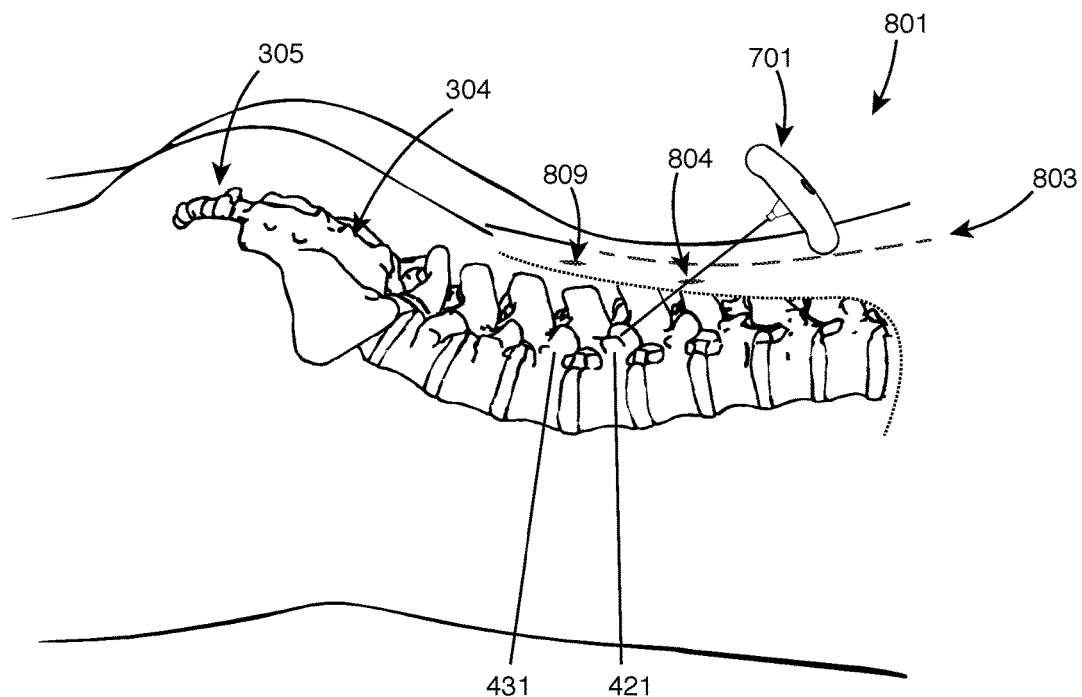
FIG. 11. A lateral, perspective view of a patient with a portion of a spine shown, to demonstrate a needle advanced towards a transverse process, in steps in certain embodiments of the invention.

In certain embodiments, a target transverse process is accessed using minimally invasive techniques. For example, the step of inserting a cannulated needle 202, shown in FIG. 2 includes guiding a needle to the target transverse process. Referring to FIG. 10 and FIG. 11, a needle 701, such as a cannulated needle, is inserted into a patient 801 to a portion of spine, targeting the transverse process to be fused. In certain embodiments, a needle 701 is linear, sharp at its tip, and preferably has a radio-dense property. A needle 701 may be in the form of a needle or cannula of various gauges made of metal, for example Jamshidi® needles or cannulated needles. A needle 701 may further include a small diameter, for example, less than 5 mm, such that penetration of the needle into the skin or other cellular features of the patient causes less damage to said skin or other cellular features as compared to larger diameter needles. The use of a small diameter needle, as compared to a larger diameter needle, allows the medical practitioner to more easily adjust the path of the needle 701 if it is determined that the path is inaccurate with less damage to soft tissue. The radio-dense property of a needle 701 allows a medical practitioner to view the approach angle of such needle from the surface to the correct endpoint using images from a bone-imaging device to help maintain an accurate path to the targeted transverse process.

Figure 12:
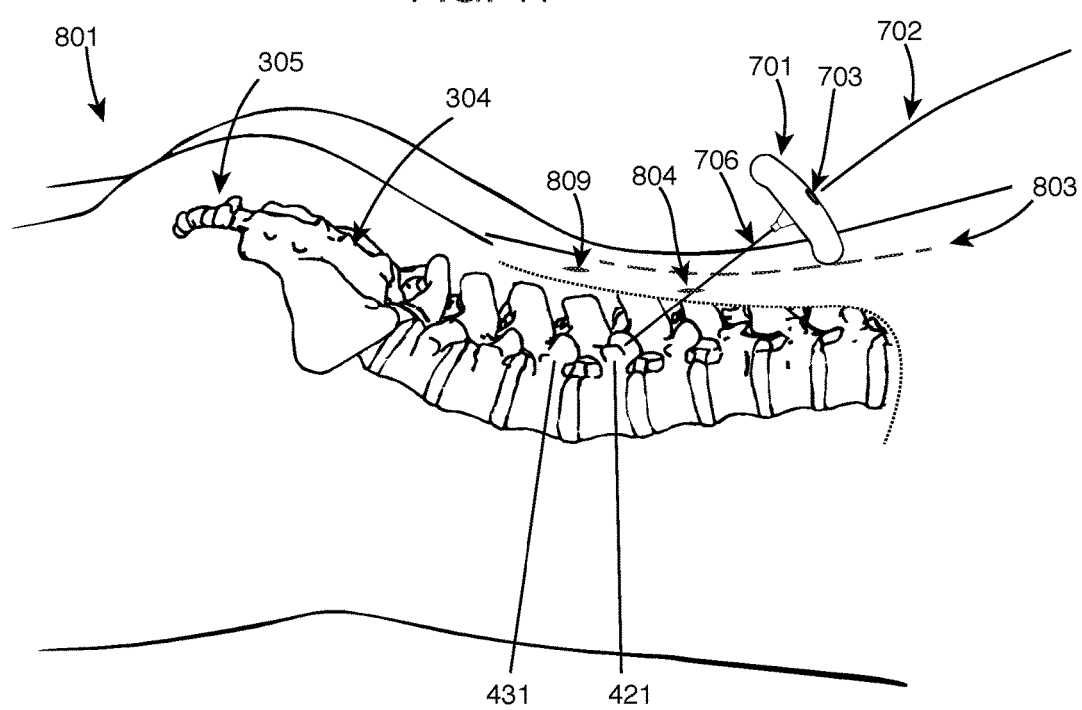
FIG. 12. A lateral, perspective view of a patient with a portion of a spine shown, to demonstrate a guide wire advanced through a needle, in steps in certain embodiments of the invention.

In certain embodiments, the optional insert guide wire step 203 shown in FIG. 2, involves placing a guide wire through an incision made in a previous step. In certain embodiments of the invention, a guide wire 702 is inserted after the insert cannulated needle step 202. In certain embodiments, as shown in FIG. 12, a guide wire 702 is placed through the cannula 703 of a needle 701, and further inserted through the shaft 706 of such needle 701 until it reaches a surgical site. Subsequently, a needle 701 is removed, leaving a guide wire 702 in its place. It will be appreciated by those skilled in the art that access to a surgical can be achieved using a non-cannulated needle, and further placing a series of dilators over the non-cannulated needle.

Figure 13A:
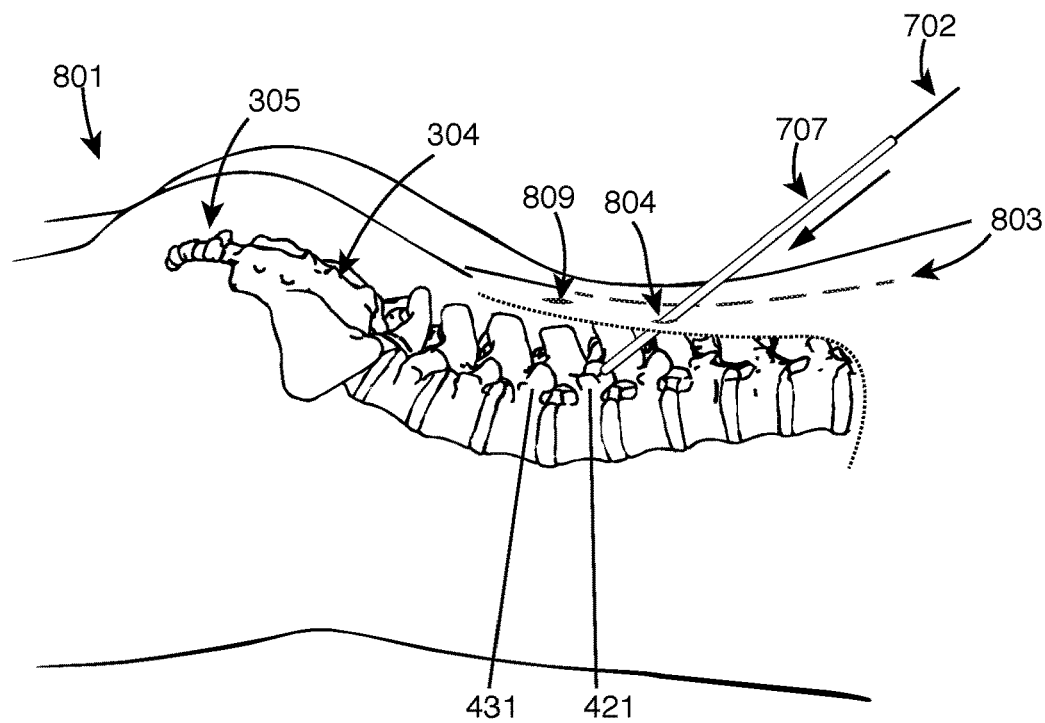
FIG. 13A. A lateral, perspective view of a patient with a portion of a spine shown, to demonstrate a dilator following a guide wire, in steps in certain embodiments of the invention.
Figure 13B:
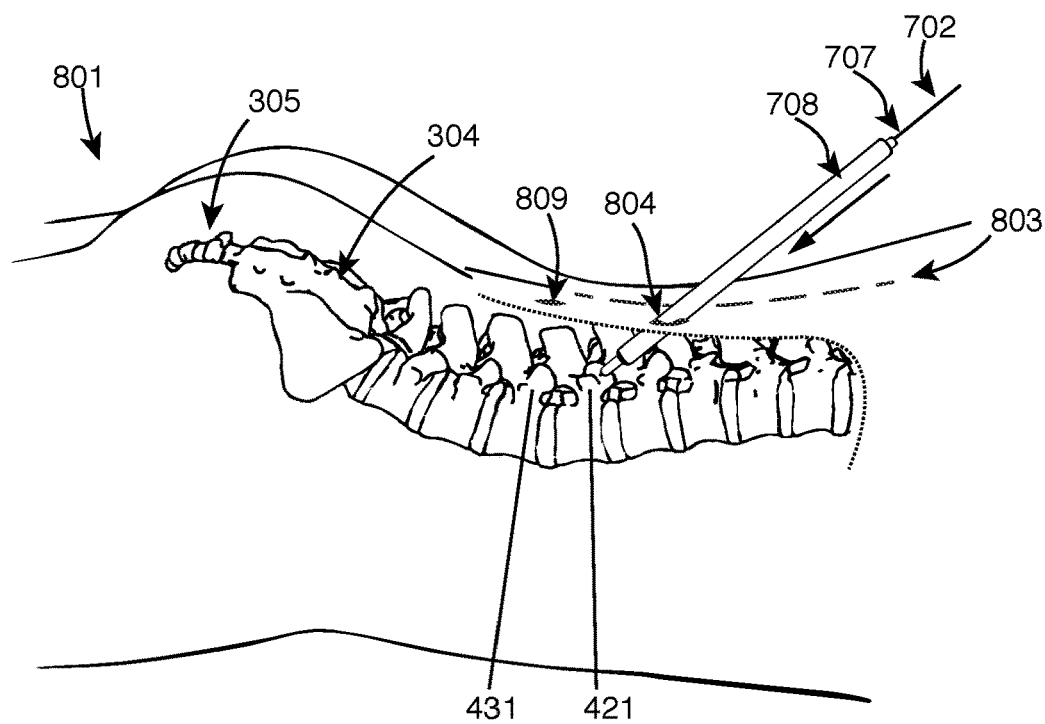
FIG. 13B. A lateral, perspective view of a patient with a portion of a spine shown, to demonstrate a dilator advanced, in steps in certain embodiments of the invention.
Figure 50A:
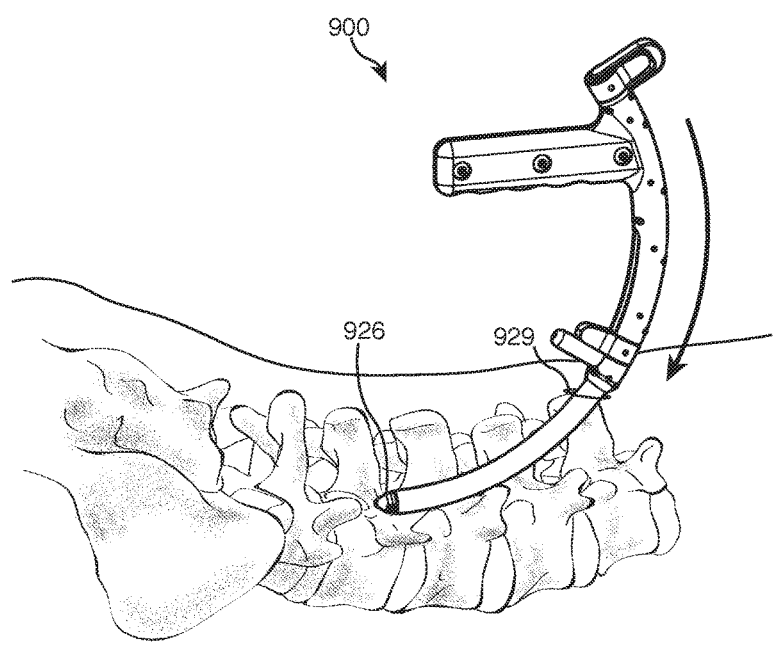
FIG. 50A. Representative view of a graft delivery assembly in use.
Figure 50B:
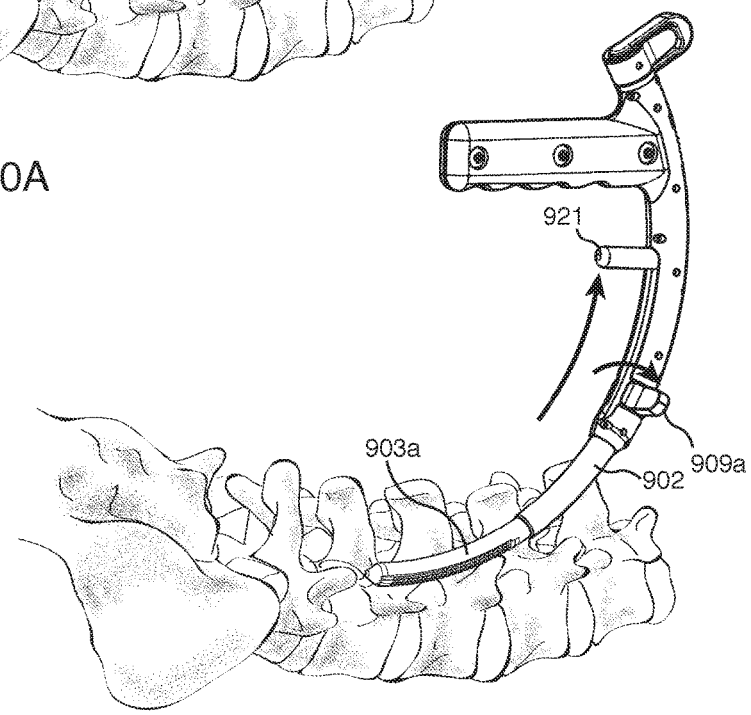
FIG. 50B. Representative view of a graft delivery assembly in use.
Figure 50C:
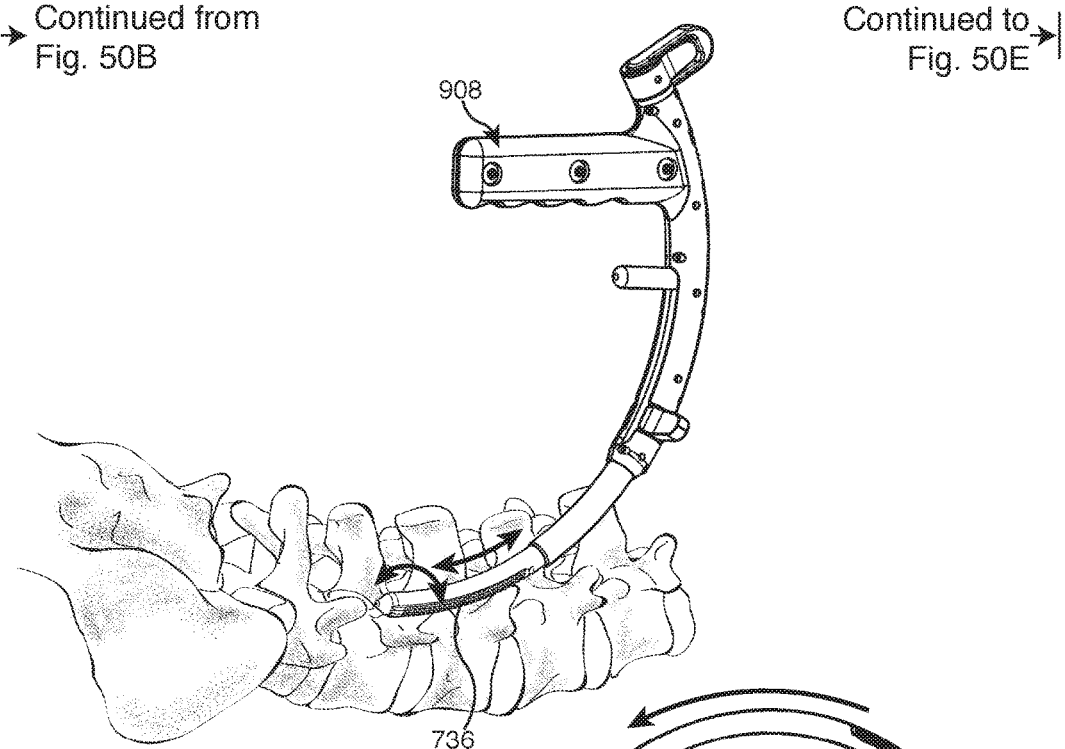
FIG. 50C. Representative view of a graft delivery assembly in use.
Figure 50D:
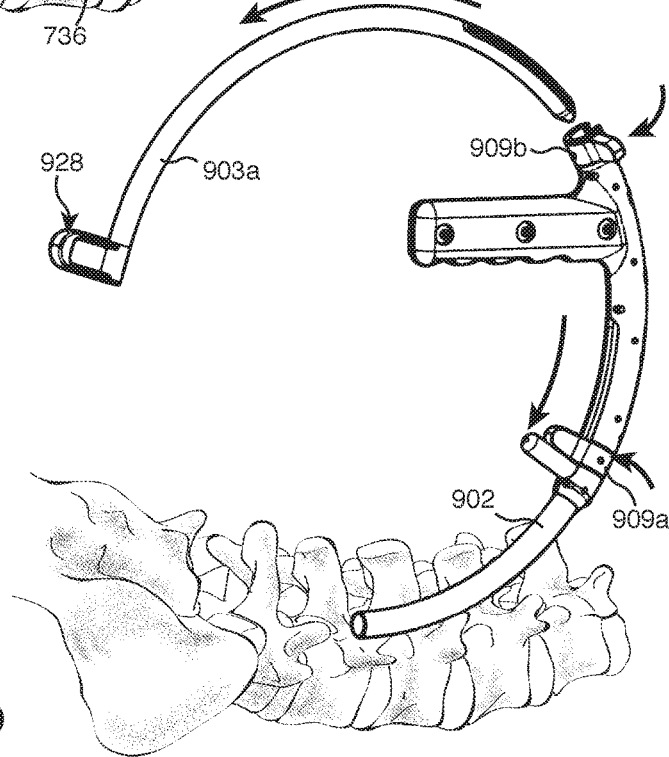
FIG. 50D. Representative view of a graft delivery assembly in use.

In certain embodiments, insert dilator step 204, and insert larger dilators and dilate path step 205 (FIG. 2) optionally includes the method of placing a series of dilators over a guide wire in sequence. In one example, a first dilator 707 includes an opening to slide over a guide wire 702, as shown in FIG. 13A, or in another example, a second dilator 708 includes an opening to slide over a first dilator 707, as shown in FIG. 13B. A series of sequentially larger diameter dilators can be used to widen the path to a transverse process. A path established through a dilator or through a cannulated instrument used in certain embodiments of the invention allows insertion of instruments to the desired location within the patient 801. Furthermore, a dilator functions as a pathway for a user to guide instruments, devices, and bony material such as those described here to the surgical site. In certain embodiments of the invention, the graft delivery tool incorporates beveled end 926 as depicted in FIG. 50A, such that the optional insert guide wire step is rendered unnecessary.

It will be appreciated by those skilled in the art that the steps of inserting a cannulated needle 202 followed by the step of inserting a guide wire 203, may be accomplished by inserting a first guide wire, then inserting a cannulated device over the guide wire, removing the first guide wire leaving the cannulated device in place, and using a dilating devices over the cannulated device prior to the removal of the cannulated device to establish a pathway.

Certain embodiments of the invention further include the steps of insert decortication tool, step 206; and decorticate transverse processes step 207; as shown in FIG. 2A. It can be appreciated that an all-in-one assembly, such as a graft delivery assembly shown in FIGS. 43-53 can be performed in step 212, followed by a decorticate transverse processes step 213 (shown in FIG. 2B). In certain embodiments, the insert decortication tool step 206 includes placing a decortication tool through a dilator or a cannulated instrument. In other embodiments, the decortication tool incorporates a beveled end placed percutaneously over the transverse processes, and allows an insert decortication tool step 206 to be completed simultaneously with steps 202-204. Scraping of a bone surface, particularly the cortical bone, causes bleeding, which advantageously promotes bone healing and/or osteogenesis. Certain embodiments of decortication tools, allow a medical practitioner to prepare bone surfaces for advantageous bone growth when bony material is placed on such decorticated bone surface or surfaces. In the certain embodiments of the invention, the graft delivery tool or assembly incorporates an abrading surface 736 as depicted in FIG. 43B, such that the graft delivery tool or assembly performs the same intended function as a standalone decortication tool. In certain embodiments, therefore, the insert decortication tool step is accomplished by utilizing the graft delivery assembly or tool itself as the decortication tool.

In certain embodiments, a decortication tool or the graft delivery tool incorporating a decorticating surface is used to decorticate one or more transverse processes. In certain embodiments, a configuration of a decortication tool, such as the cutter assembly 709 shown in FIG. 14 includes a cutter sheath 1403, handle 1401, trigger 1405, a distal end 1402, and a cutter blade 1404. A cutter assembly 709 is used for decorticating a surface that is perpendicular or near perpendicular to the path of entry, for example, through an approach path 604 shown in FIG. 7B.

Referring to FIG. 14, a cutter assembly has a trigger 1405 attached to a collar 1417 with a first pivot 1415. A collar 1417 is attached to a cutter sheath 1403. A trigger 1405 is also attached to a second pivot 1414. A second end 1411 of a cutter blade 1404 is attached to a cutter shaft 1418. The cutter shaft 1418 is secured to a handle 1401, such cutter shaft 1418 extending internally of a cutter sheath 1403. Pulling or pushing of a trigger 1405 allows deployment and retraction of a cutter blade 1404 relative to a cutter sheath 1403. In certain embodiments, a cutter assembly 709 is passed through a dilator 712, shown for example in FIG. 19. When a cutter blade 1404 is deployed against a transverse process, it will be appreciated that rotation of such cutter assembly 709 about its longitudinal axis allows the cutter to decorticate bone.

An embodiment of a deployed cutter blade 1404 is shown in FIG. 15. A cutter blade 1404 begins from a first end 1406, extends distally and then laterally outward to form a distal segment 1407. The cutter blade then doubles back at a juncture 1409, extends laterally inward, further extending proximally and ending at a second end 1411 to form a proximal segment 1410. The location of a junction 1409 defines the cutting radius, when a cutter blade 1404 is rotated. Still referring to FIG. 15, such cutter blade has a cutter edge 1408 on a distal segment 1407 and a proximal segment 1410 has a blunt edge 1412 that, when rotated against a bone surface (such as that of a transverse process), decorticates the bone. A distal segment 1407 has an opening 1413 that accommodates a peg located in a cutter shaft 1418, allowing the distal segment 1407 to be guided as it slides up and down when the cutter is deployed or retracted.

Figure 21:
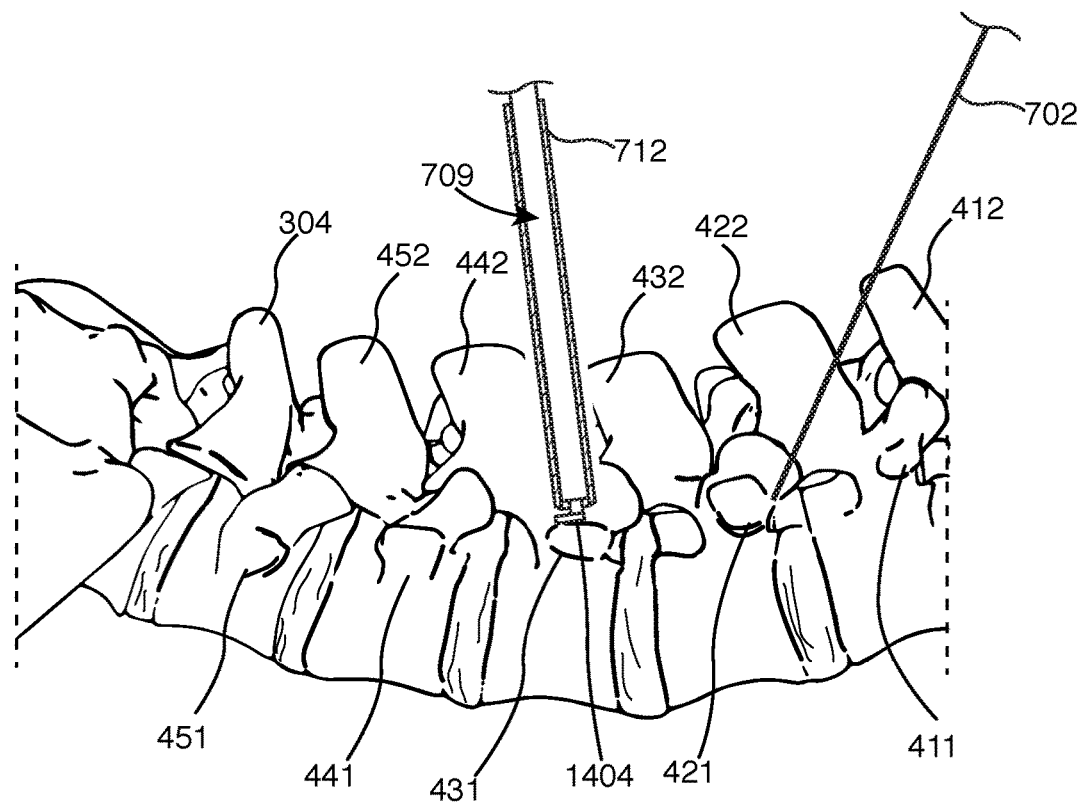
FIG. 21. A lateral view of a spine showing a guide wire placed on a transverse process, and a cannula comprising a cutter placed on an inferior transverse process.
Figure 22:
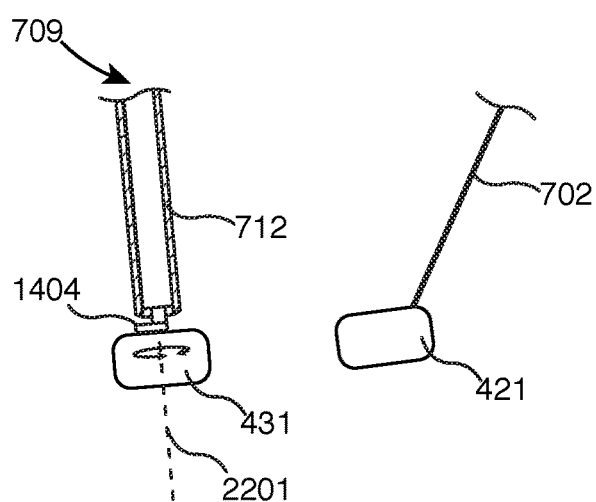
FIG. 22. A side view showing a guide wire placed on a transverse process, and a cannula incorporating a cutter placed on an inferior transverse process.

In certain embodiments, as seen in FIG. 21, the cutter assembly 709 may be passed through a dilator 712. Referring to FIG. 22, surface decortication of the transverse process is achieved by inserting a cutter assembly 709, and by rotating the cutter blade 1404 a longitudinal axis 2201. The angle of decortication suing such a cutter assembly 709 may range from 65° to 90°. While in the examples shown in FIG. 21 and FIG. 22, a cutter assembly 709 decorticates the right transverse process of L3 431, it will be appreciated by those skilled in the art that other transverse processes may be decorticated using a cutter assembly.

Figure 16:
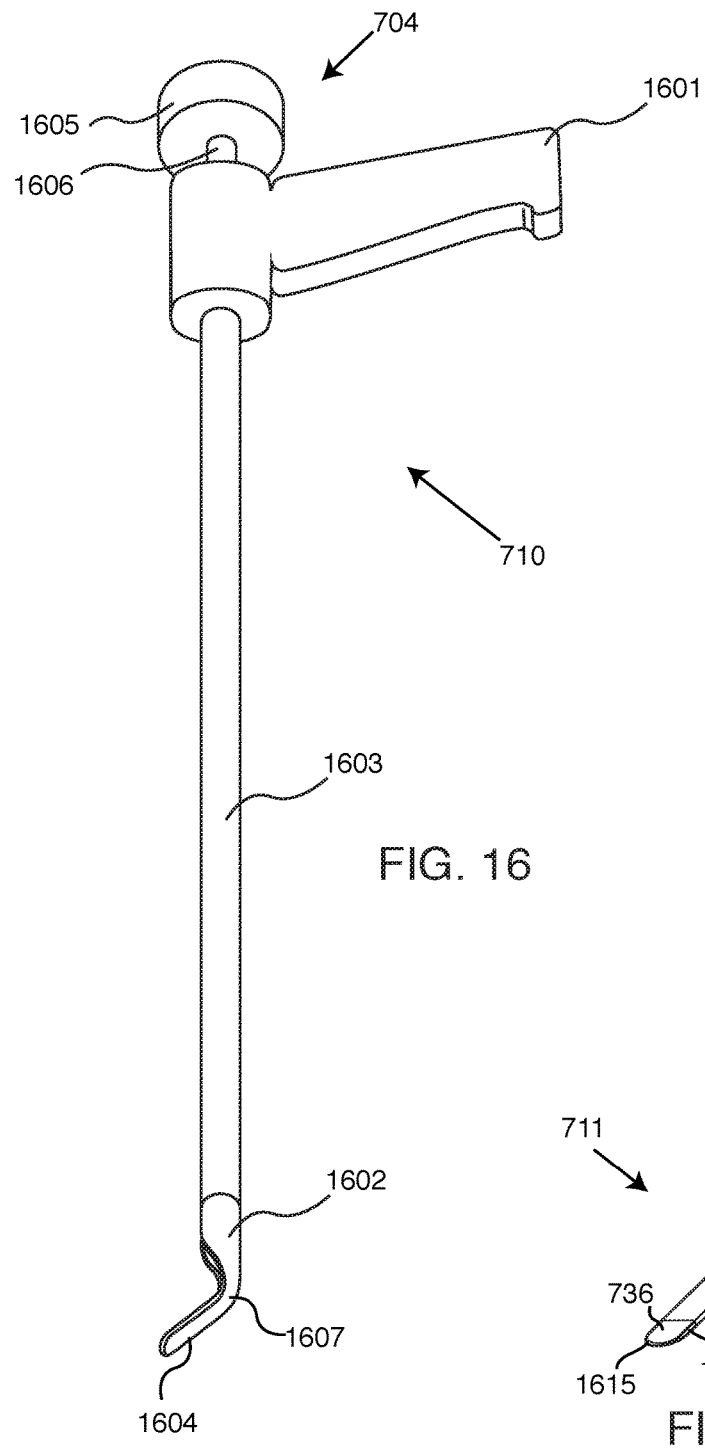
FIG. 16. An angled tool assembly in certain embodiments of the invention.

In certain embodiments, a decortication tool accesses and decorticates a surface of a transverse process at an approach angle other than perpendicular. In certain embodiments, the decortication tool generally includes, for example, a graft delivery tool 730 (e.g. FIG. 34B), or a decorticating rod 903a, 952 of a graft delivery assembly 900, 950 featuring an abrading surface 736. In certain embodiments, an angled tool assembly 710 as shown in FIG. 16 is used to decorticate a transverse process through an approach path that is 90° or less. For example, an angled tool assembly 710 may be used to pass through an approach path 602 as shown in FIG. 7A. In certain embodiments, a decortication tool accesses a surface of a transverse process through a curvature, as shown for example in FIGS. 27-33 and FIGS. 42-53.

Figure 17:
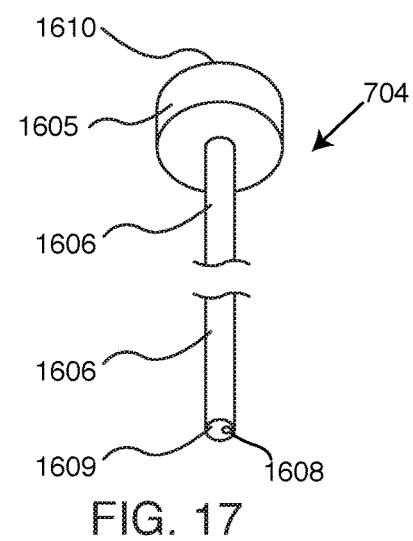
FIG. 17. An inner assembly in certain embodiments of the invention.

In certain embodiments, as shown in FIG. 16, a configuration of an angled tool assembly 710 includes a handle 1601, an outer sheath 1603, a head 1602, and a tongue 1604 disposed at an angle. In certain embodiments, an angled tool assembly further comprises an inner assembly 704, also shown in FIG. 17. Referring to FIG. 17, an inner assembly 704 has a handle 1605, a shaft 1606, and an opening 1608, extending the length from a distal end 1609 to a proximal end 1610. In certain embodiments, an angled tool assembly 710 further includes a cutter tool 711, as further shown for example in FIG. 18.

Figure 18:
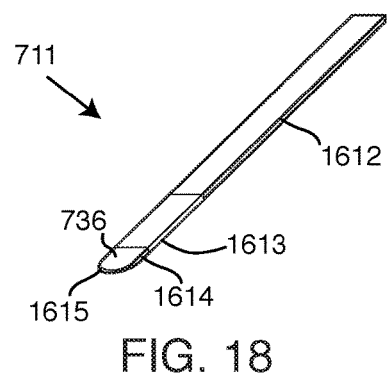
FIG. 18. A cutter tool in certain embodiments of the invention.

In certain embodiments, a cutter tool 711 (as shown in FIG. 18) is inserted through an opening 1608 of an inner assembly 704 (as shown in FIG. 17), where such opening extends the length from a distal end 1609 to a proximal end 1610 of the inner assembly. Referring to FIG. 18, a cutter tool 711 has, in certain embodiments, a shaft 1612, a flexible region 1613, a distal end 1614, an abrading surface 736, and a cutter edge 1615. An abrading surface 1617 (for example, a rasp) has a surface that can decorticate a surface of a bone. A cutter edge 1615 has a sharpened edge that can decorticate a surface of a bone. A cutter tool 711 slides back and forth within an opening 1608 of an inner assembly 704. A cutter edge 1615 can protrude out of a distal end 1609 of an inner assembly 704 as referred to in FIG. 17. Referring to FIG. 18, a cutter tool 1711 further bends at a flexible region 1613. Referring to FIG. 16, FIG. 17, and FIG. 18, a cutter tool 711 is placed through an inner assembly 704, which is then placed through a sheath 1603 of an angled tool assembly 710. A user, for example may slide the cutter tool 711 in a back and forth movement within an inner assembly 704. It will be appreciated that the decortication of a transverse process may include manipulation of the tool in a side-to-side action or twisting action. When a cutter tool is pushed further in, the distal end 1614 of a cutter tool 711 to press against a curved feature 1607 of an angled tool assembly 710 head 1602. The present inventors have recognized that the back and forth movement, the side-to-side action, and twisting actions a user may employ during use of a cutter tool, or a decortication tool functions to accomplish decortication of one or more transverse processes in a minimally invasive manner.

Figure 19:
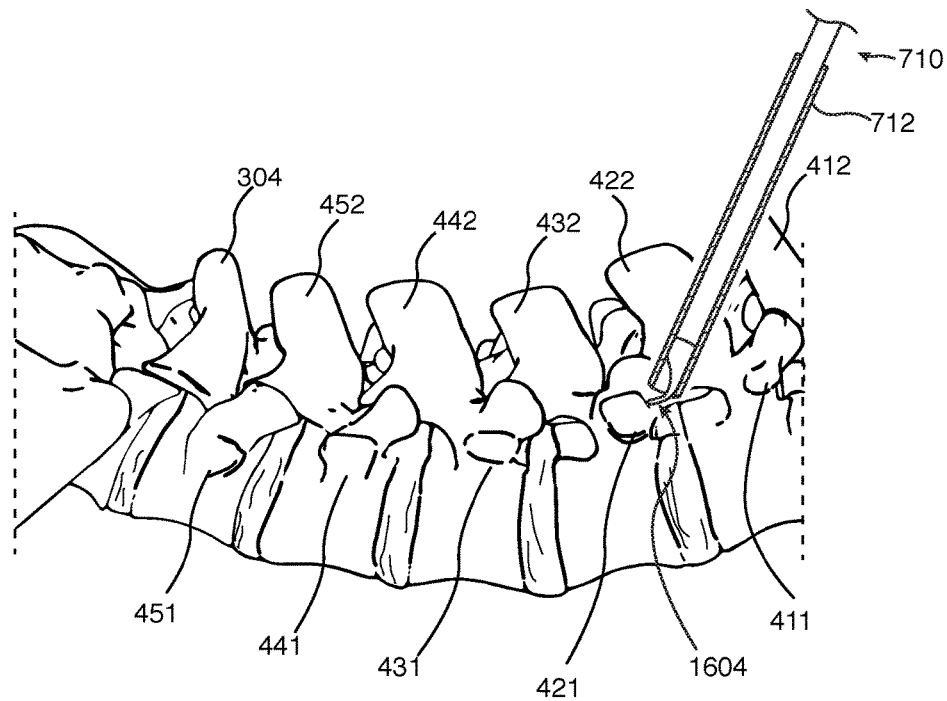
FIG. 19. A side view of a spine showing an embodiment of an angled tool assembly.
Figures 20A, 20B, 20C:
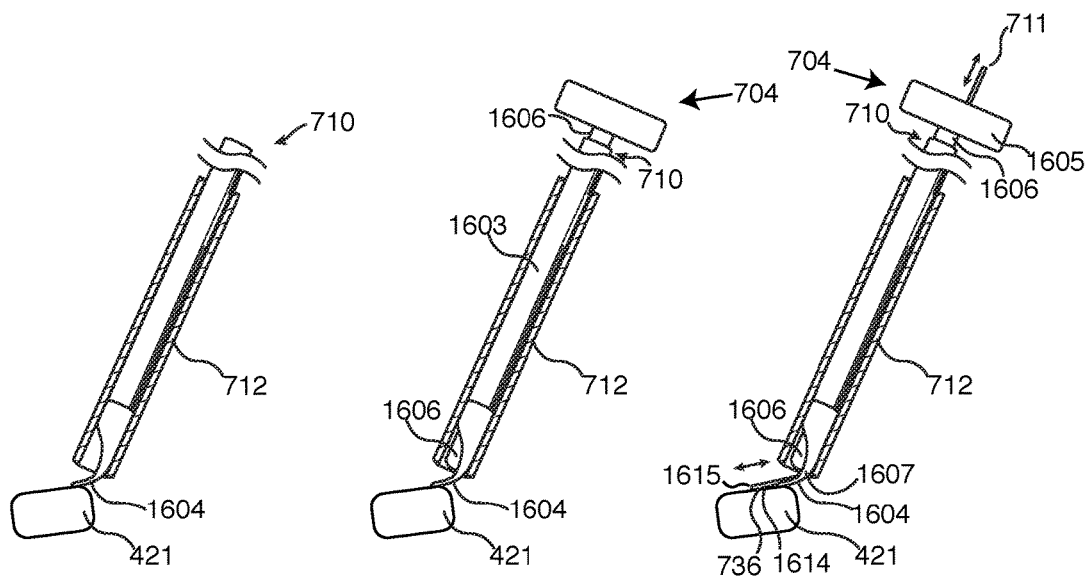
FIG. 20A. A side view of an angled tool assembly in certain embodiments.
FIG. 20B. A side view of an angled tool assembly with an inner assembly in certain embodiments.
FIG. 20C. A side view of an angled tool assembly with an inner assembly and a cutter tool in certain embodiments.

Referring to FIG. 19, and FIG. 20A, as an example, an angled tool assembly 710 is disposed at a right transverse process of L2 421 through a dilator 712. A tongue 1604 is positioned near the right transverse process of L2 421.

Further referring to, FIG. 20B, an inner assembly 704 is placed within an outer sheath 1603 of an angled tool assembly 710. Further referring to FIG. 20C, the cutter tool 711 is placed through the shaft 1606 of an inner assembly 704, where a handle 1605 in certain embodiments has an opening to accommodate such cutter tool 711. The cutter tool 711 having a flexible region 1613 (as shown in FIG. 18) bends and follows the contour of a curved feature 1607 of a tongue 1604. Through a back and forth movement, a cutter tool 711 cutter edge 1615 and/or an abrading surface 736 decorticates a surface of the right transverse process of L2 421.

It will also be appreciated that in certain other embodiments, a cutter tool 711 shaft 1612 is affixed to the inner assembly 704, whereby the flexible region 1613 and the distal end 1614 protrude from a distal end 1609 of the inner assembly 704. In such embodiment, a user may slide the inner assembly 704 and cutter tool 711 simultaneously within an angled tool assembly 710.

It will be appreciated that in alternative embodiments a tongue 1604, as shown in FIG. 16, may be provided with differing lengths, as to more accurately guide an instrument such as a guide wire or a cutter tool. It will further be appreciated that certain forms of an angled tool assembly 710 have a curved feature 1607 having an angle ranging from 0° to 90°.

Figures 23A, 23B:
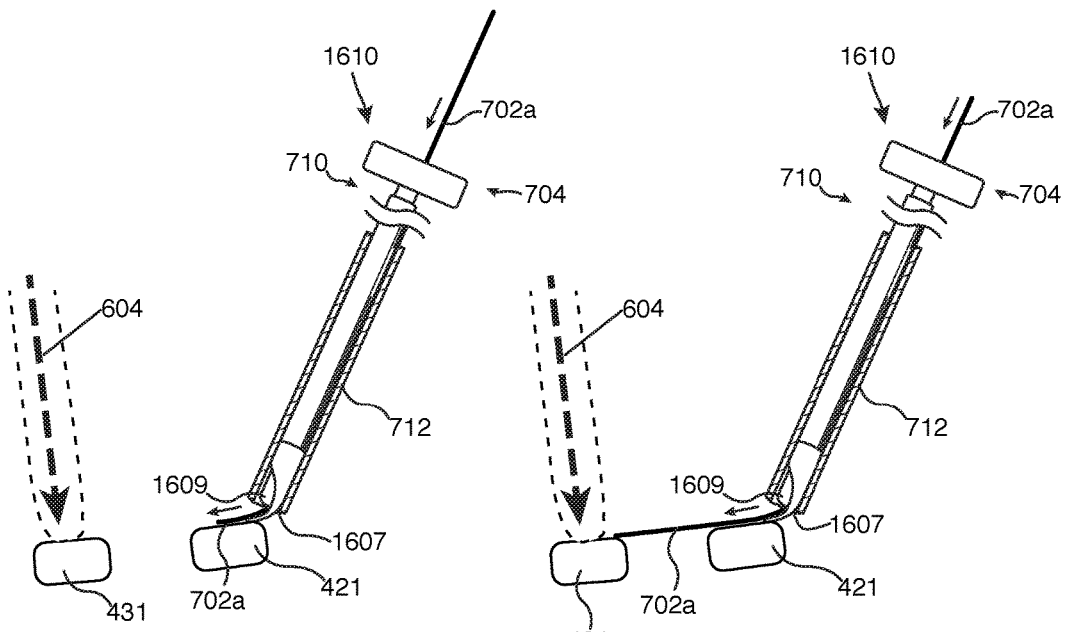
FIG. 23A. A side view showing an approach path on an inferior transverse process, and an angled tool assembly on a superior transverse process.
FIG. 23B. A side view showing an approach path on an inferior transverse process, and an angled tool assembly on a superior transverse process, where a guide wire is advanced.

In certain embodiments, a guide wire may be placed through an angled tool assembly. In such cases, a guide wire may help to establish a path between two transverse processes. Furthermore, a flexible dilator may be inserted in such path to deposit bony material. Referring to FIG. 23A, and FIG. 23B, in certain embodiments, a guide wire 702a is used to create a path from a first transverse process to a second transverse process. A guide wire 702a is placed inside an angled tool assembly 710, and further inserted from a proximal end 1610 to a distal end 1609 of an inner assembly 704. As seen in FIG. 23A and FIG. 23B, the path of a guide wire 702a is initially directed to a first transverse process (for example, the right transverse process of L2) 421, changing its trajectory towards second adjacent transverse (for example, the right transverse process of L3) 431 with the aid of a curved feature 1607.

Figures 23C, 23D:
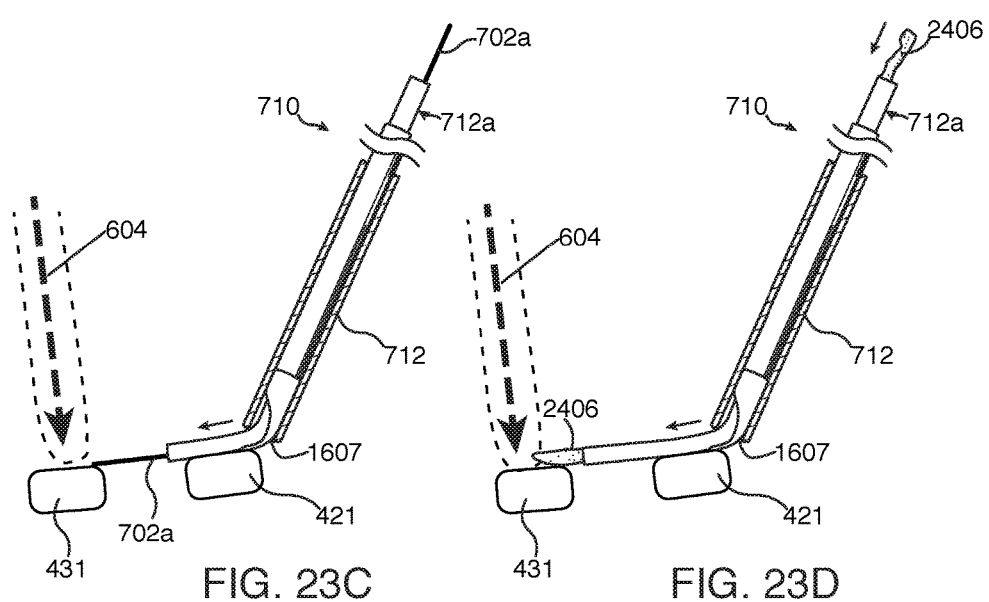
FIG. 23C. A side view showing an approach path on an inferior transverse process, and an angled tool assembly on a superior transverse process, where a flexible dilator is placed over such guide wire.
FIG. 23D. A side view showing an approach path on an inferior transverse process, and an angled tool assembly on a superior transverse process, and bony material is placed in an intertransverse process space through the flexible dilator.

After a guide wire 702a spans from the right transverse process of L2 421 to the right transverse process of L3 431, an inner assembly 704 may be removed. A flexible dilator 712a is inserted through the angled tool assembly 710 by following the guide wire 702a as shown in FIG. 23C. The flexible dilator 712a may further be placed between the transverse processes of L2 421 and L3 431. Once placed, the guide wire 702a is removed.

Referring to the flow diagram in FIG. 2A, the insert bony material into intertransverse process path step 208 includes procedures to place bony material in contact with and substantially between at least two adjacent transverse processes. In one example, as shown in FIG. 23D, bony material 2406 is inserted through the flexible dilator 712a, thereby allowing the bony material 2406 to be placed between the transverse processes of L2 421 and L3 431. In another embodiment, bone graft is placed by positioning the graft delivery assembly or tool (for example, an assembly 900, 950 shown in FIGS. 43A and 51A) over the targeted one or more transverse processes, and retracting a delivery sheath (for example, sheath 902 shown in FIG. 43A and shaft 951 shown in FIG. 51A) over a plunger (for example, plunger 903b, 953 shown in FIGS. 49C and 51A) to force the bony material out of the sheath in proximity to the transverse processes as the sheath is retracted. Once bony material is in position, the associated placement apparatuses, which may include any or the entire graft delivery tool, flexible dilator, and/or guide wire may be removed. Referring to FIG. 1 and FIG. 2A-B, in certain embodiments, these steps are followed with a step involving the closing or suturing of the incision 104, 209, 215.

The present inventors contemplate that in preferred embodiments of the invention that bony material is placed in the intertransverse process space after the surfaces of the one or more transverse processes are decorticated. As shown for example in FIG. 23A, FIG. 23B, FIG. 23C, and FIG. 23D an approach path 604 may serve as the delivery path of the apparatuses to decorticate the transverse process of L3 431.

In certain embodiments, portions of a cutter assembly 709 shown in FIG. 14 or a cutter tool 711 shown in FIG. 18 are made of materials suitable for decortication and bending. One known suitable material that approximates the preferred biomechanical specification for a cutter blade 1404 (seen in FIG. 15), cutter edge 1615 (seen in FIG. 18), curved feature 1607 (seen in FIG. 16), a distal end 1614 (seen in FIG. 18), but not limited to such parts, is an alloy of nickel and titanium (e.g. Ni56-Ti45 and other alloying elements by weight), such as for example, Nitinol strip material #SE508, available from Nitinol Devices and Components Inc. in Fremont, Calif. The material exhibits substantially full shape recovery (i.e. recovered flexion when strained from 6% to 10%, which is a factor often better than the recovered flexion at the strain levels of stainless steel).

Figure 24A:
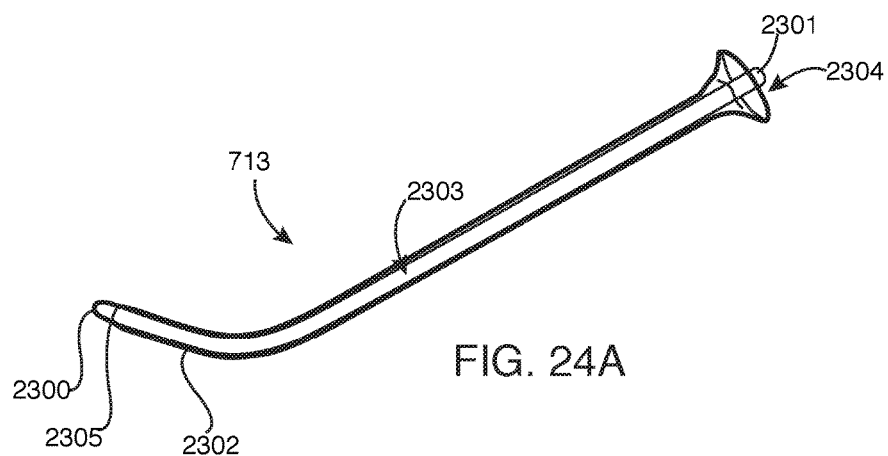
FIG. 24A. A distending device is shown with a sheath closed tightly around the tool.
Figure 24B:
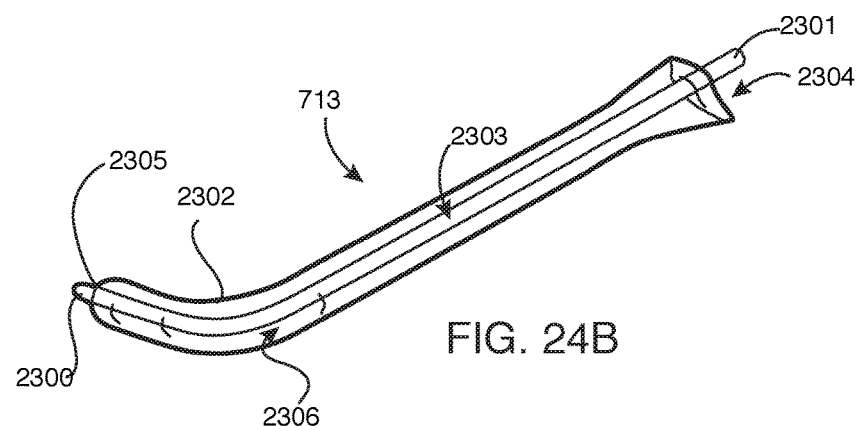
FIG. 24B. A distending device is shown with dilated sheath, allowing the passage of bony material through the sheath.

Referring to FIG. 2A, certain embodiments of the insert bony material into intertransverse process path step 208, includes using a distending device to place bony material in the space between the transverse processes. Referring to FIG. 24A and FIG. 24B, an embodiment of an distending device 713 has a bendable rod 2303, having a sheath 2302, a portion of such sheath 2302 having an attachment point 2305 proximal to a distal end 2300 of a bendable rod 2303. The expansion of the sheath 2302 creates a space 2306 between the sheath 2302 and bendable rod 2303 as shown in FIG. 24B. An opening 2304 of the sheath 2302, located near the proximal end 2301 of the bendable shaft 2303, allows a medical practitioner to place material into the opening 2304 to deliver bony material in the space 2306.

Figure 25:
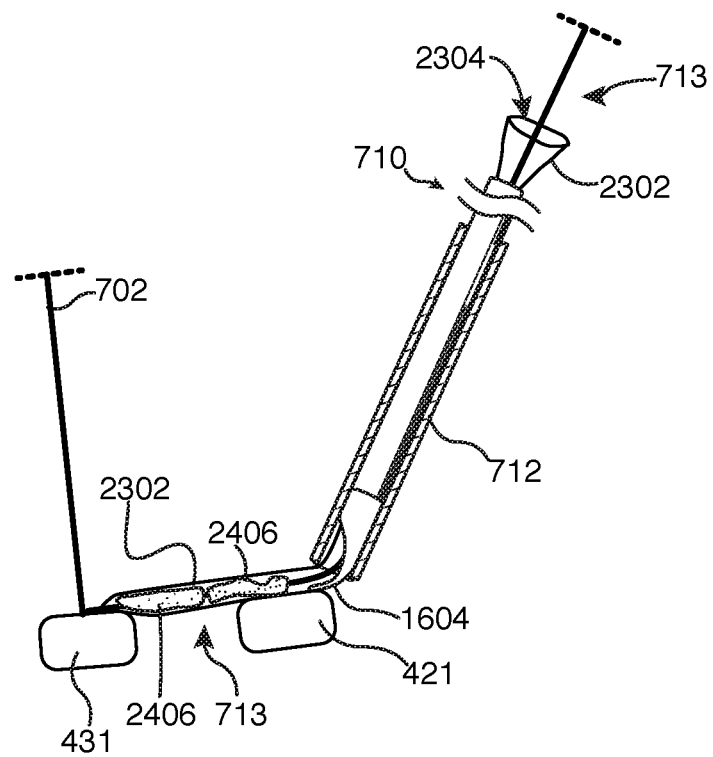
FIG. 25. A distending device is shown in an example position as it may be used during a spinal fusion procedure, acting to facilitate the passage of bony material to the fusion site.

Referring to FIG. 25, in certain embodiments, a distending device 713 is placed between the transverse processes of L2 421 and L3 431. In one example, the distending device 713 is guided using an angled tool assembly 710. Bony material 2406 is inserted through an opening 2304 of a sheath 2302 of a distending device 713. A distal end of a distending device 713 is filled with bony material 2406 in an area between the transverse process of L2 421 and the transverse process of L3 431.

Figure 26:
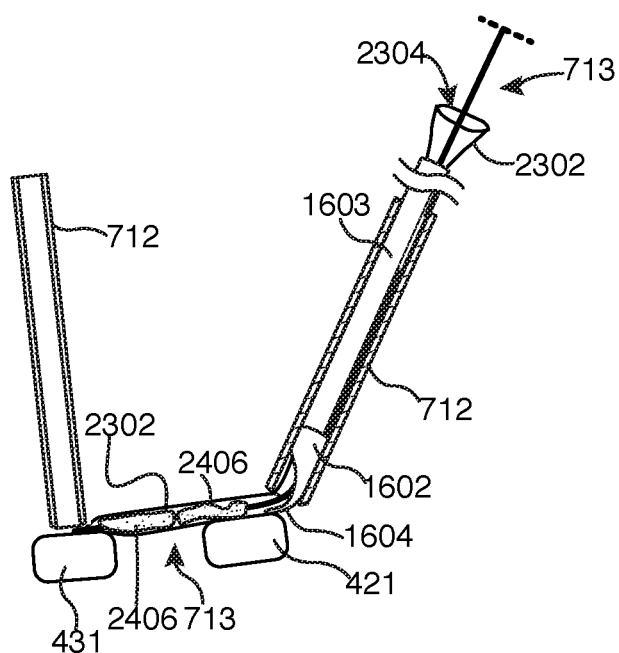
FIG. 26. A distending device is shown in an example position as it may relate to second guide wire 702b.

Referring to FIG. 1, certain embodiments of the insert bony material in intertransverse space step 103, includes steps to open a distal end of a distending device previously filled with bony material, removing the distending device, and leaving a deposit of bony material between a first transverse process and a second transverse process. A dilator 712 or access portal placed in a desired path directed to the transverse process of L3 431 as shown in FIG. 26, allows access with various medical instruments, such as a surgical scissor to cut, open, or otherwise distribute contents of the distending device 713. In one example, a cutting device, such as a surgical scissor, is used to cut a distal portion of the sheath 2302 of the distending device 713. The contents of a distending device 713 (e.g. bony material 2406) are released into the intertransverse process space as the distending device 713 is removed. In certain embodiments, once the bony material is in position, the dilator 712 and guide wire are removed.

In certain embodiments, the surgical procedure to accomplish fusion of adjacent transverse processes is accomplished through a generally curved pathway. Referring to FIG. 1, an embodiment of such a procedure includes the following steps: (1) posterior-lateral access to the spine, step 101; (2) decorticate bone surface, step 102; (3) insert bony material in intertransverse space, step 103; and (4) close incision, step 104 are accomplished through a generally curved pathway. An example of such a curved pathway is established, for example, with assemblies and tools shown in FIGS. 27-33 and 42-53.

Figure 27:
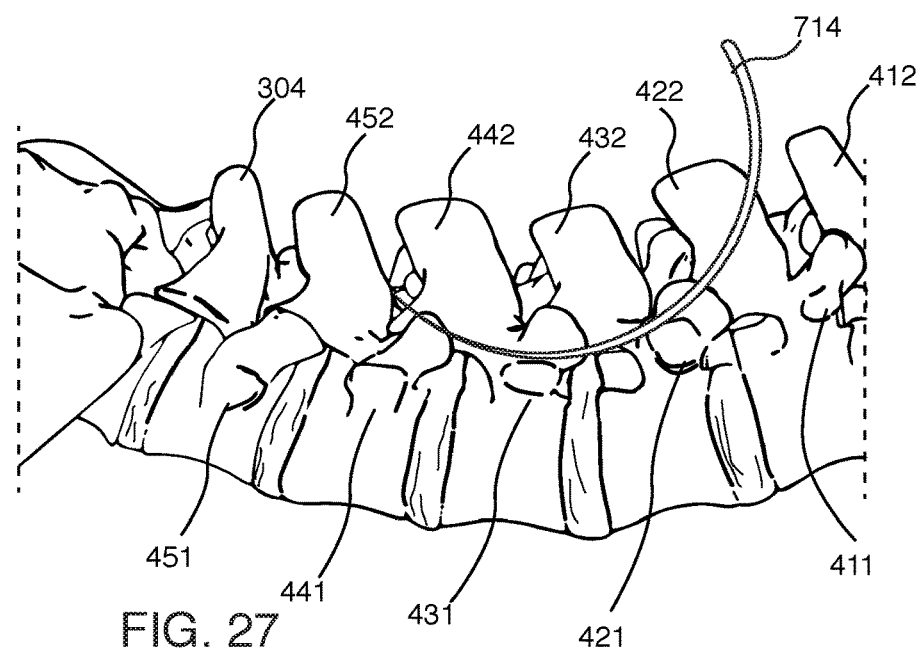
FIG. 27. Embodiments of a curved needle shown in relation to a portion of a spine.
Figure 28A:
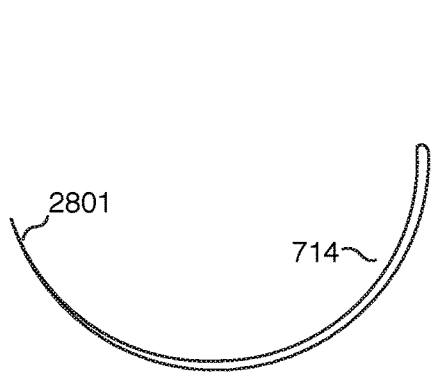
FIG. 28A. A curved needle in certain embodiments.

Referring to FIG. 27, in certain embodiments of an invention for the fusion of adjacent transverse processes, the space between the transverse processes of L2 421 and L3 431 is accessed with a curved needle 714. In certain embodiments, a curved needle 714 is cannulated. As shown, for example, in FIG. 27, a curved needle 714 is inserted through the tissue located posterior to the target transverse processes from a posterior approach. For example, a curved needle is 714 passed through the tissue of a patient from a posterior approach, posterior to a right transverse process 431 of L3, and a right transverse process 421 of L2. Referring to FIG. 28A, a curved needle 714 has a tip 2801. In certain embodiments, the arc of the curved needle 714 has a diameter typically between 75 mm and 200 mm, allowing access to two adjacent transverse processes. It will be appreciated that the arc of a curved needle 714 can vary depending on the level that the transverse process targets.

Figure 28B:
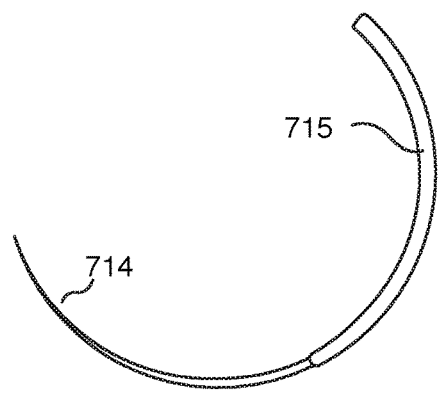
FIG. 28B. A curved needle and a dilator in certain embodiments.
Figure 28C:
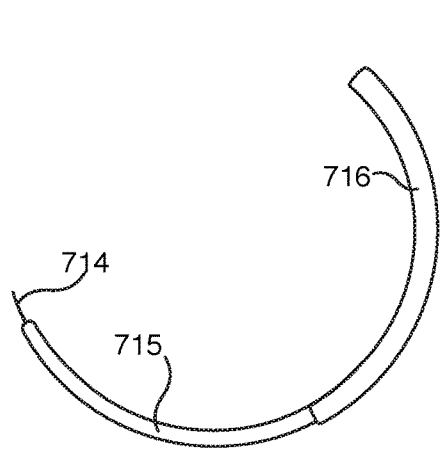
FIG. 28C. A curved needle and dilators in certain embodiments.

Referring to FIG. 28B, in an embodiment, a dilator 715 is cannulated, and is inserted over a curved needle 714. Further referring to FIG. 28C, and FIG. 28D, a series of dilators 716, and 717 are inserted over each successive dilator (e.g. dilator 716 slides over dilator 715) to expand the pathway towards the transverse processes. In certain embodiments, dilators have a curved form generally matching the curvature of the arc of a curved needle. It will also be appreciated that dilators can refer to surgical instruments having a straight form.

Figure 28D:
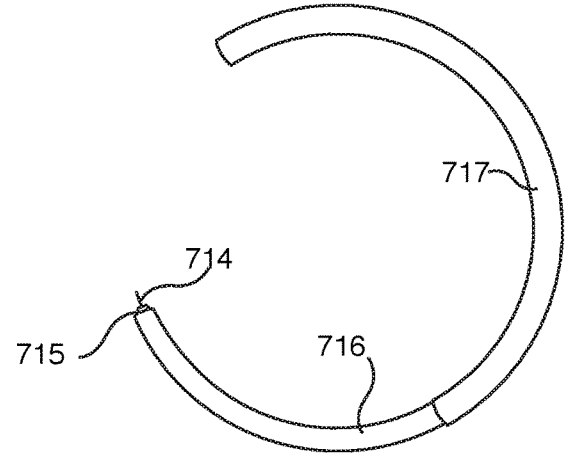
FIG. 28D. A curved needle and dilators in certain embodiments.
Figure 29:
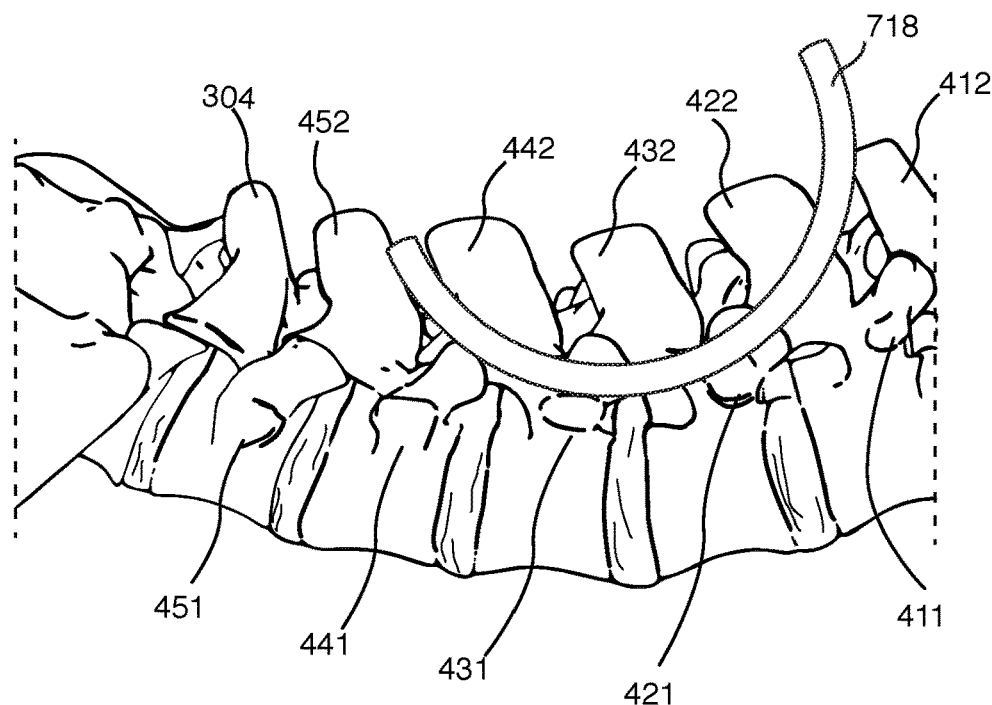
FIG. 29. A dilator in certain embodiments shown in relation to a portion of a spine.
Figure 30A:
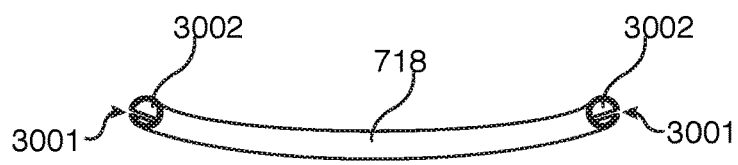
FIG. 30A. Top perspective view of an access portal comprising a small longitudinal opening in certain embodiments.
Figure 30B:
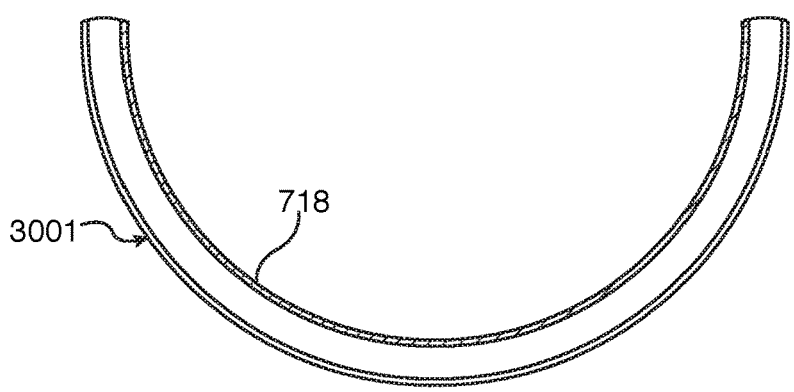
FIG. 30B. Cross-sectional view of an access portal comprising a small longitudinal opening in certain embodiments.

In an embodiment, an access portal 718 as shown in FIG. 29 is further slid over a dilator 715, 716, 717 or a needle 714 as shown in FIG. 28A, FIG. 28B, FIG. 28C, and FIG. 28D. A user may generally insert instruments, devices, tools, bony material, and the like through an access portal or a dilator. Referring to FIG. 30A and FIG. 30B, in certain embodiments of an access portal 718, there is an opening 3002 running longitudinally.

In an embodiment, an access portal 718 may be placed in the vicinity of two transverse processes (L2 transverse process 421, and L3 transverse process 431, for example), as seen in FIG. 29. In certain embodiments, as shown for example in FIG. 31A, a proximal end 3103 is passed through a first incision 3101, and a distal end 3104 is passed through a second incision 3102. It will be appreciated that in varying embodiments, the instruments, including curved needles, dilators, and access portals may not necessarily pass through a second incision 3102. It will also be appreciated that a first incision 3101 may originate either superior or inferior to the surgical site (i.e. the location of the fusion). It will also be appreciated that the pathway to the surgical site may be directed in an inferior to superior direction, or a superior to inferior direction.

Figure 31A:
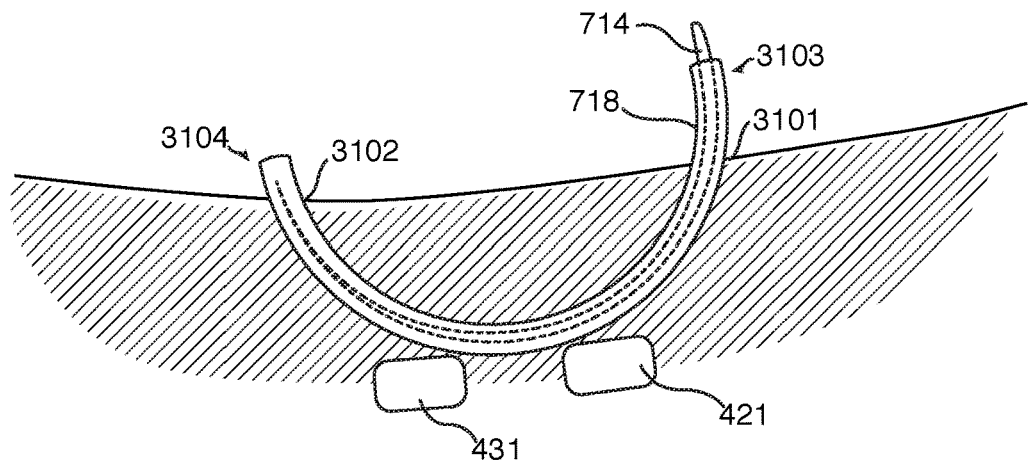
FIG. 31A. Cross-sectional view of a patient's back showing an access portal and a curved needle, in certain embodiments.
Figure 31B:
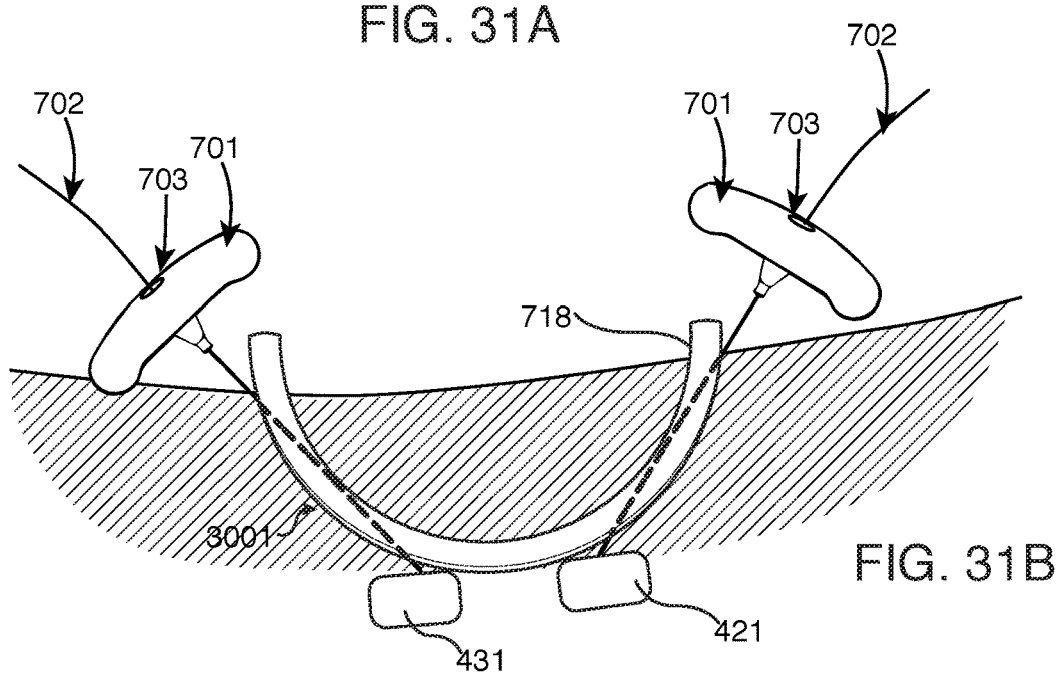
FIG. 31B. Placement of a cannulated needle through an access portal in a cross-sectional view of a patient's back, in certain embodiments.
Figure 31C:
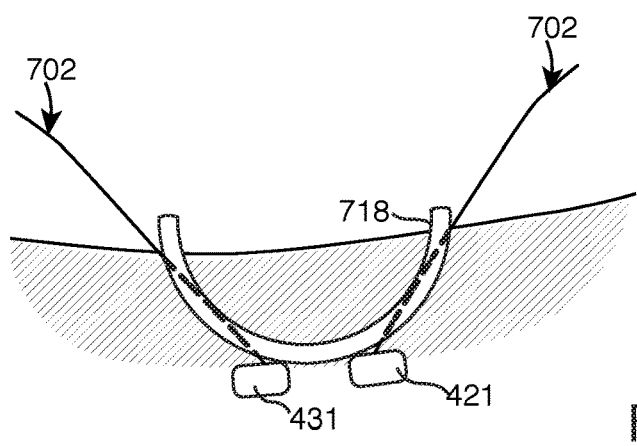
FIG. 31C. Placement of a guide wire through an access portal in a cross-sectional view of a patient's back, in certain embodiments.

Referring to FIG. 30B, certain embodiments of an access portal 718 have a small longitudinal opening 3001 that allows passage of certain instruments. A small longitudinal opening 3001 in those embodiments runs longitudinally along the body of the access portal. In certain embodiments, a small longitudinal opening 3001 is located on the exterior curved surface of an access portal 718. Referring to FIG. 31B, one or more needles 701, such as Jamshidi® needles, are passed through an access portal 718 to transverse processes through a small longitudinal opening 3001. In certain embodiments, as further shown in FIG. 31B, a guide wire 702 is placed through a cannula 703 of the needle 701 and advanced through a shaft 706 of the needle 701 until it reaches the transverse process. Subsequently, the needle 701 is removed, leaving the guide wire 702 in place, as shown for example in FIG. 31C. Once one or more guide wires 702 are in place, a curved needle 714 may take the place of the access portal to preserve the curved path 3201, as shown in the diagram in FIG. 32A.

Figure 32A:
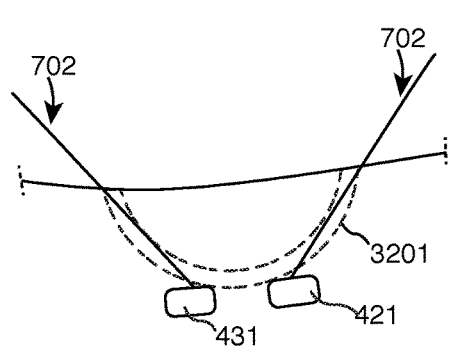
FIG. 32A. Embodiments of a step where a curved needle and guide wires are placed through a curved path, shown in a cross-sectional view of a patient's back.
Figure 32B:
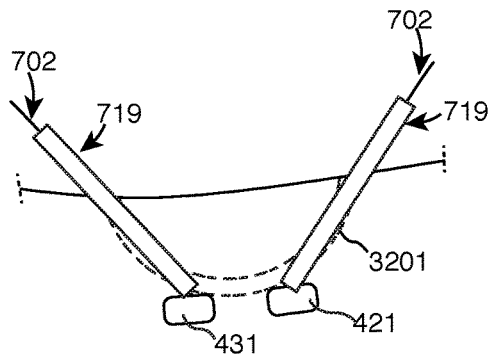
FIG. 32B. Embodiment of a step where dilators are placed through a curved path, shown in a cross-sectional view of a patient's back.

In certain embodiments, using the guide wires 702 as guides, a medical practitioner may insert one or more dilators 719 to the transverse processes 421 and 431, as shown in FIG. 32B. In certain embodiments, a medical practitioner uses decortication tools, including, but not limited to a cutter assembly 709 seen in FIG. 14, rasps, files, and drills to decorticate the surface of the transverse processes through a dilator.

Figure 33A:
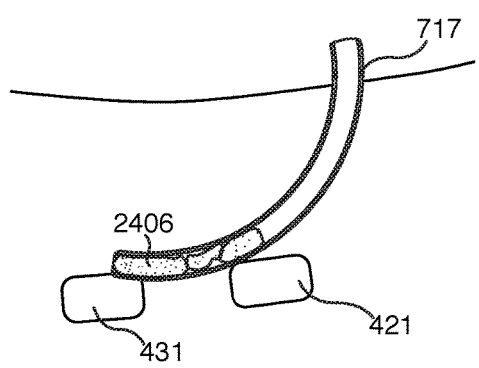
FIG. 33A. Embodiment of a step where a dilator is used to deposit a bony material, shown in a cross-sectional view of a patient's back.
Figure 33B:
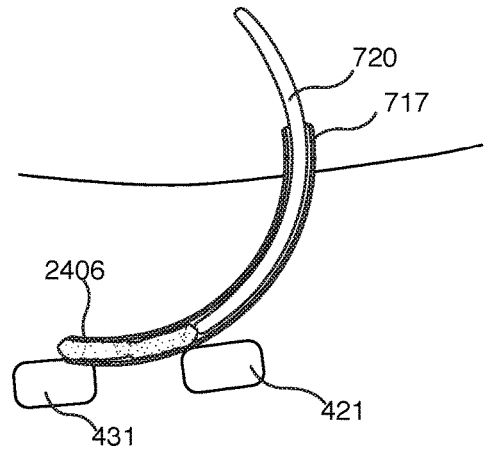
FIG. 33B. Embodiment of a step where a plunger dispenses bony material from a dilator, shown in a cross-sectional view of a patient's back.
Figure 33C:
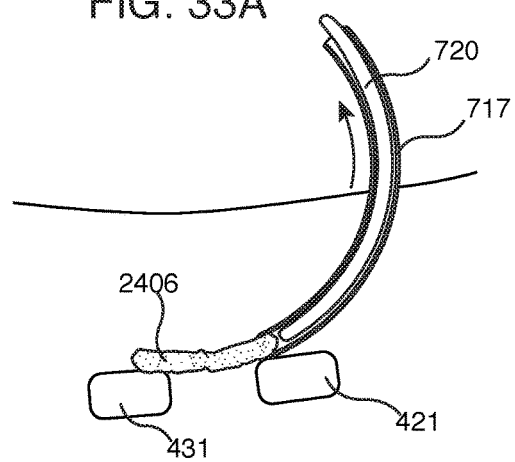
FIG. 33C. Embodiment of a step showing bony material being deposited in an intervertebral space, shown in a cross-sectional view of a patient's back.
Figure 33D:
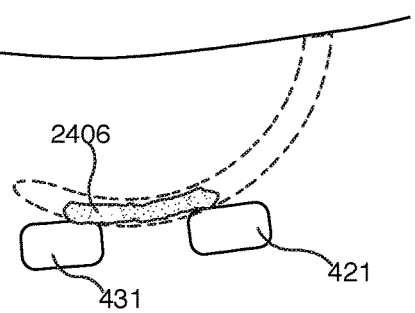
FIG. 33D. Embodiment of a step showing bony material deposited in an intervertebral space, shown in a cross-sectional view of a patient's back.

Referring to FIG. 33A, in certain embodiments, bony material 2406 is inserted into an end of a dilator 717. A plunger 720 is further inserted to deposit bony material 2406, as shown in FIG. 33B. Referring to FIG. 33C, a plunger is used to push bony material 2406 into the intertransverse space while a dilator 717 is pulled out, which leaves the bony material 2406 in place as further shown in FIG. 33D.

In certain embodiments, bony material is delivered to an intertransverse space using a graft delivery tool. In certain embodiments, a graft delivery tool is used to open a path to the transverse process after an initial incision is made on the skin of a patient. In certain embodiments, a graft delivery tool is used to deliver bony material on at least one transverse process surface. In certain embodiments, a graft delivery tool incorporates features to decorticate the bone surface of one or more transverse processes. In certain embodiments, the graft delivery tool may operate independently from any guide wires or dilators, and act to define the path through the soft tissue itself with the aid of a beveled end.

A graft delivery tool 730, as shown in embodiment in FIG. 34A, FIG. 34B, and FIG. 34C, includes a handle 731, a first segment 732, and a second segment 733. In certain embodiments, a first segment 732 and a second segment 733 are connected with a segment with a bend 737. A distal end of a second segment 733 has a distal end 735. Referring to FIG. 34C, certain embodiments of a graft delivery tool 730 comprises a first segment 732 has a curvature. In certain embodiments, a graft delivery tool comprises a plurality of individual interconnected segments further comprising a first segment 732 and a second segment 733 and a segment comprising a bend 737. In alternate embodiments a graft delivery tool 730 comprises a single piece further comprising a bend 737, a first segment 732, and a second segment 733. In certain embodiments as shown in FIG. 35, a first segment 732, a bend 737, and a second segment 733 each having a hollow profile creating a duct 741, allowing the depositing of bony material or other materials. In certain embodiments, a first segment 732, a bend 737, and a second segment 733 each having a solid profile. As shown in FIG. 34D, it will be appreciated that a graft delivery tool 730, of solid profile or hollow profile, may be used to establish a pathway 3402, for the subsequent delivery of bony material between adjacent transverse processes.

In certain embodiments, a graft delivery tool 730 having a solid profile may be used by a practitioner to create a pathway 3402 from the exterior of the body to the transverse processes through an incision 3404 of the skin 3403, for example, as shown in FIG. 34D. In certain use cases, graft delivery tool 730 having a solid profile may be inserted to create a pathway to the intertransverse space after performing a pedicle screw/rod fixation procedure. In an embodiment, using an incision created while performing a pedicle screw/rod surgery, the graft delivery tool 730 having a solid profile may be inserted through an incision to create a pathway 3402 in proximity or direct contact with adjacent transverse processes and spanning therebetween, as shown in FIG. 34D.

In an embodiment, referring to FIG. 34A, variations in the length 3401 of a second segment 733 allow a practitioner to span across two or more transverse processes. For example, in an embodiment, a second segment 733a having a length of approximately 45 mm to 55 mm is appropriate for delivering bony material between two adjacent transverse processes of the lumbar spine, as seen in FIG. 34E. In certain embodiments, a second segment 733b having a length of approximately 75 mm to 85 mm is appropriate for delivering bony material between three adjacent transverse processes of the lumbar spine, as seen in FIG. 34F. In other areas of the spine, for instance thoracic spine and the cervical spine, the lengths of the first and second segments in certain embodiments may vary in relation to the distance between the adjacent transverse processes. Therefore, a user may choose a graft delivery tool 730 having a second segment 733 of appropriate length 3401 spans between the transverse processes intended to be fused.

Referring to FIG. 34B, certain embodiments of a graft delivery tool 730 incorporate an abrading surface 736 that features texturing allowing for decortication of a bone surface. In varying embodiments of the invention, the terms "abrading surface" and "decorticating surface" may be used interchangeably. In certain embodiments of the invention, the abrading surface 736 is on a graft delivery assembly as depicted in FIG. 43B. The abrading surface 736 may have features or patterns on the graft delivery tool including, but not limited to single cut, double cut, curved tooth, rasps, rifflers, and knurling. In certain embodiments, an abrading surface 736 includes one or more surface modifications that facilitate decortication of bone. In such embodiments, once a graft delivery tool or assembly is inserted into the patient to the desired area proximal or in contact with at least one transverse process, the user may apply force to the graft delivery tool or assembly (for example, a graft delivery tool 730), applying pressure on one of the desired transverse processes and manipulate the graft delivery tool or assembly to abrade the posterior surface of the targeted transverse processes. In one example, the graft delivery tool 730 may be manipulated in a variety of manners including back and forth in a lateral direction, back and forth in a superior to inferior direction, rotatively around an axis of the second segment 733 or a combination thereof. Such manipulations may take place percutaneously and without making further incisions in the preferred embodiment of the invention. In certain embodiments, a graft delivery tool 730 further comprising an abrading surface 736, as exemplified in FIG. 34B, may be inserted into a pathway 3402 (shown in FIG. 34D) to decorticate the surfaces of the right L3 transverse process 431 and the L4 transverse process 441. In certain embodiments, an abrading surface 736 is found on an outer surface of a tool or element, including but not limited to a decorticating rod 903a (FIG. 49A), 952 (FIG. 51B), and a delivery shaft 951 (FIG. 53A).

In certain embodiments, as shown in FIG. 35, a graft delivery tool 730 with hollow profile comprises a plunger head 740 located inside a second segment 733. The plunger head 740 is interconnected with a plunger 738 that is located at a proximal end of a first segment 732. The plunger head 740 and plunger 738 are interconnected by a connector 739, where the connector 739 traverses through the hollow profile of the first segment 732, a bend 737 and at least a portion of the second segment 733. Depressing the plunger 738 advances the plunger head 740, allowing a user to control the dispensation of loaded bony material delivered through a duct 741. In certain embodiments, a connector 739 comprises a flexible material. A connector 739 may comprise a material make-up including, but not limited to nickel-titanium alloys such as Nitinol, stainless steel and titanium. In alternate embodiments, a connector may comprise a plastic or polymeric material.

In certain embodiments a graft delivery tool 730 may house bony material 2406 loaded in the duct 741 of the second segment 733 on the distal side of the plunger head 740. It will be appreciated that as the bony material is loaded in the duct 741 of the second segment 733, the bony material pushes the plunger head 740, away from the distal end of the second segment. The graft delivery tool 730, with loaded bony material 2406 may be inserted through an pathway 3402, placing the second segment 733 in proximity or in contact with two or more adjacent transverses processes. A practitioner may then retract the graft delivery tool 730 back through the pathway 3402 while depressing the plunger 738 to deposit the bony material spanning between the transverse processes.

Referring to FIG. 36A, a cross-section A-A of the second segment 733 of a graft delivery tool 730 is designed with a number of profiles in certain embodiments. As shown in FIG. 36B, in certain embodiments, a cross-section 733a is substantially circular. Referring to FIG. 36C, in certain embodiments, a second segment 733 has a cross-section 733b with a rounded form 733d inter-spaced with a straight form 733c. Referring to FIG. 36D, in certain embodiments, a second segment 733 has a cross-section 733e comprising a rounded form 733f with a first radius and a second rounded form 733g with second radius. Referring to FIG. 36E, in certain embodiments, a second segment 733 has a triangular cross-section 733h with legs of straight or curved form. Referring to FIG. 36F, certain embodiments have a second segment 733 with a generally rectangular cross-section 733i. It will be appreciated that the cross-section of a second segment 733, a bend 737, and/or a first segment 732 may comprise any shape, including, but not limited to polygons, ovals, rhomboids, and fabiforms. It will be appreciated that the cross-section of a graft delivery tool 730 may be a solid body, or have a hollow profile creating a duct to hold bony material. It will also be appreciated that in certain embodiments, the cross sections 733a-733i and other cross sections may be applied to other instrumentation disclosed herein (for example, a delivery shaft 901, 951, a graft delivery sheath 902, a curved rod 903, a decorticating rod 903a, 952, a plunging rod 903b, 953 and other instruments, tools, and assemblies disclosed herein).

Referring to FIG. 37A, FIG. 37B, and FIG. 37C, showing a top view of a second segment 733, certain embodiments may include a distal end 735 of shapes including, but not limited to, a pointed tip 735a, a rounded tip 735b, a blunt tip 735c, and a hemispherical tip. It will be appreciated that in certain embodiments, a distal end 735 may have a beveled end to allow separating tissue.

Referring to FIG. 38A showing a bottom view of a second segment, an abrading surface having knurling 736a allows decortication of bone. Certain embodiments include spacers 736b between surfaces 736a, as shown in FIG. 38B. Certain embodiments have an abrading surface comprising splines 736c, as shown in FIG. 38C. Further referring to FIG. 38D, certain embodiments comprise a splined surface 736c located between a knurling surface 736a.

Referring to FIG. 39, in certain embodiments, a second segment 733 comprises gradations that can be viewed under radiography, such as notches 742. In certain embodiments notches 742 allow a user to observe the location and placement of a graft delivery tool 730 when viewed under a radiograph. It will be appreciated that notches 742 may be found on other tools disclosed herein, including, but not limited to, for example a curved needle 714, dilators 715, 716, 717, and an access portal 718, as shown in FIG. 28D.

In certain embodiments, a graft delivery tool 730 with a hollow profile has a ratcheting device 757 as shown in FIG. 40. The ratcheting device 757 further comprises a plunger 738, an inner shaft 743, and a pawl 744. A spring 747 displaced over the inner shaft 743 interfaces with a medial step feature 748 of the inner shaft. When placed within a handle 731, the spring interfaces between a stop 749 and the medial step feature 748 maintaining a sprung offset between the medial step feature 748 and the stop 749. The pawl 744 interfaces with teeth 745 located on the proximal end of a connector 739. The teeth 745 only allow the movement of the connector 739 through the interface with the pawl 744 in a distal direction, extending the connector and a connected plunger head 740 toward the distal end of the graft delivery device 730. When the plunger 738 is depressed, the pawl 744, engaged with the teeth 745, advances the connector 739 distally. Upon release of the plunger 738, the spring 747 retracts the inner shaft 743 and the pawl 744, disengaged from the teeth 745 leaves the connector 739 and plunger head 740 in place. A user may successively advance the plunger head 740 and any loaded bony material 2406 through repeated depression of the plunger head 738.

In certain embodiments, a graft delivery tool 730 with hollow profile comprises a thumb-wheel device 758 further comprising a thumb-wheel 750 as shown in FIG. 41A. A thumb-wheel 750 is attached to a tab 756 extending from a handle 731. A pin 754 secures the thumb-wheel 750 to tab 756.

In certain embodiments, referring to FIG. 41B, a graft delivery tool 730 comprising a thumb-wheel device 758 further comprises a thumb-wheel 750 secured to a handle 731 with a pin 754 further comprises a pinion 753 that engages with a rack 751 comprising teeth 745, disposed within the handle 731. The proximal end of the rack 751 is attached to a plunger 738 and the distal end of the rack is connected to the distal end of a connector 739. The distal end of the connector 739 is further attached to a plunger head 740. A user may rotate the thumb-wheel 750 in a first direction to extend the plunger head 740 in a distal direction to dispense loaded bony material in a second direction to retract the plunger head 740 in a proximal direction. The retraction of the plunger head 740 may be desired to allow a practitioner to load bony material into the graft delivery tool 730 for successive bony material depositions.

It will be appreciated that in certain embodiments, a graft delivery tool with a hollow profile uses a curved first segment with the various embodiments of the handles disclosed. Referring to FIG. 42, for example, a graft delivery tool 730 comprises a first segment 732 and second segment 733 having a continuous curved profile attached to a handle 731 and further comprising a thumb-wheel device 758. It will be appreciated that the length and arc radius of a first segment 732 may be modified to accommodate the spanning the intertransverse space between two or more transverse processes.

Figure 43A:
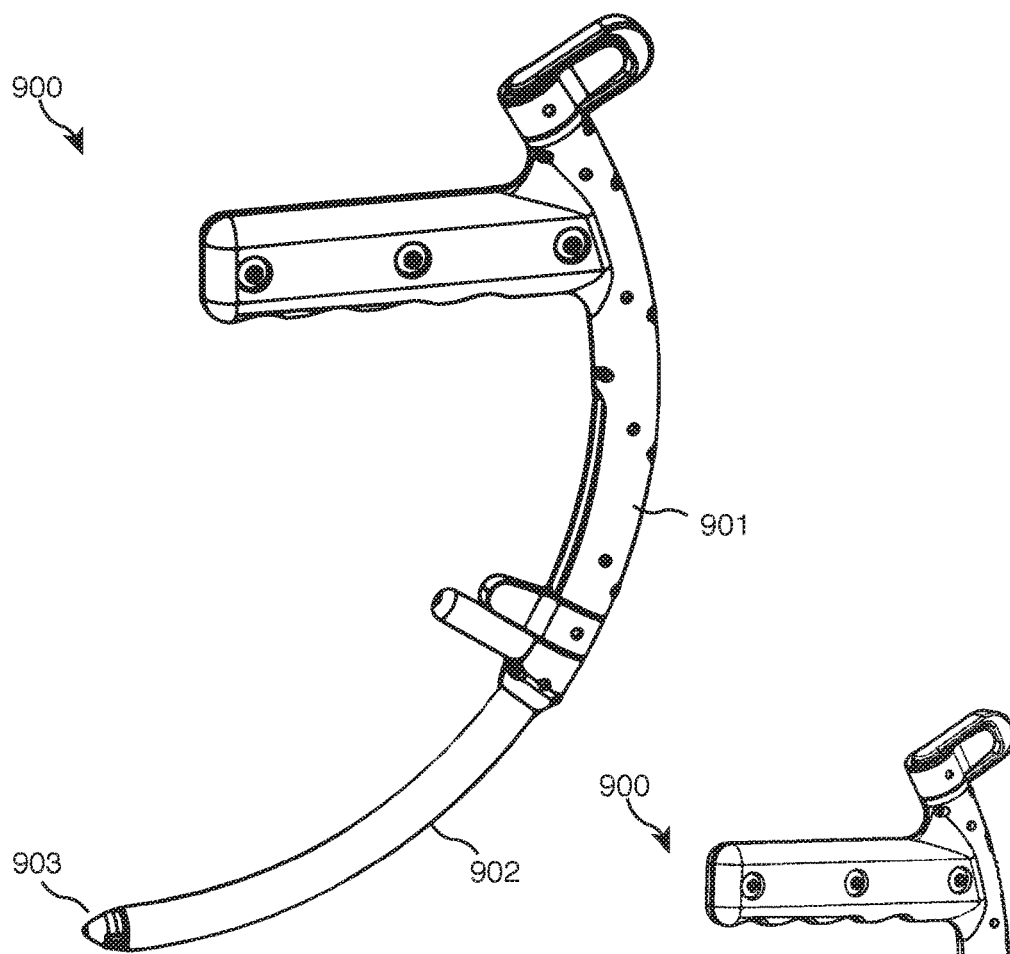
FIG. 43A. A graft delivery assembly in certain embodiments.
Figure 43B:
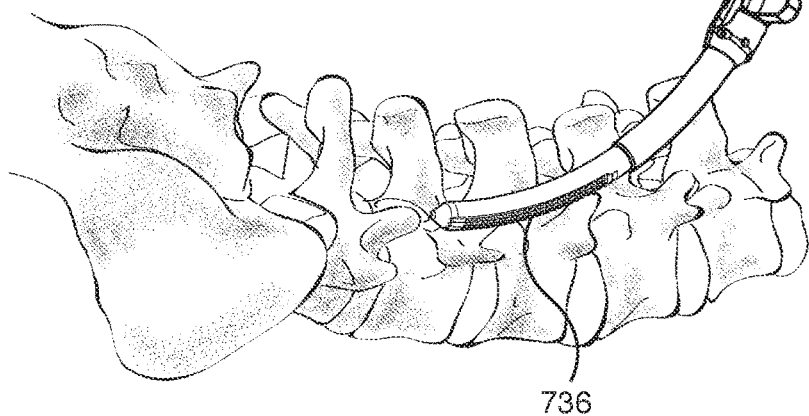
FIG. 43B. A graft delivery assembly in certain embodiments.

Referring to, for example, FIG. 43A-B, certain embodiments of the invention include a graft delivery assembly 900, further including a delivery shaft 901, delivery sheath 902, and at least one curved rod 903. As shown in FIG. 44A-D, certain embodiments of a delivery shaft 901 have a tool insertion end 904 and a graft delivery end 905. Referring to FIG. 44D, a delivery shaft 901 follows a central axis 911, whereby a shaft pathway 907 is a pathway following a central axis 911 and allows communication between the tool insertion end 904 and a graft delivery end 905. In certain embodiments, a central axis 911, 960, or a portion thereof may generally follow a curved line. For example, as shown in FIG. 44D, a central axis may be defined by an arc having a radius 912.

In certain embodiments, a central axis curvature has a radius of between 10.14 cm (4 inches) and 20.32 cm (8 inches), preferably with a radius of 15 cm (6 inches). However, other radii may be used in certain embodiments. Generally, a central axis closely aligns with the lordotic curvature of certain regions of the spine. It can be appreciated that a central axis may also follow an arc with a logarithmic spiral, an arc comprising more than one radius, or other path having a portion or all of such path having a curvature. The shaft pathway is a pathway generally allows passage of other instruments, including a delivery sheath 902, a curved rod 903, bony material, and other objects described herein and elsewhere relevant to surgical procedures. It will be appreciated that a delivery sheath 902 and a curved rod 903 may also be referred to as a curved element.

Figure 44A:
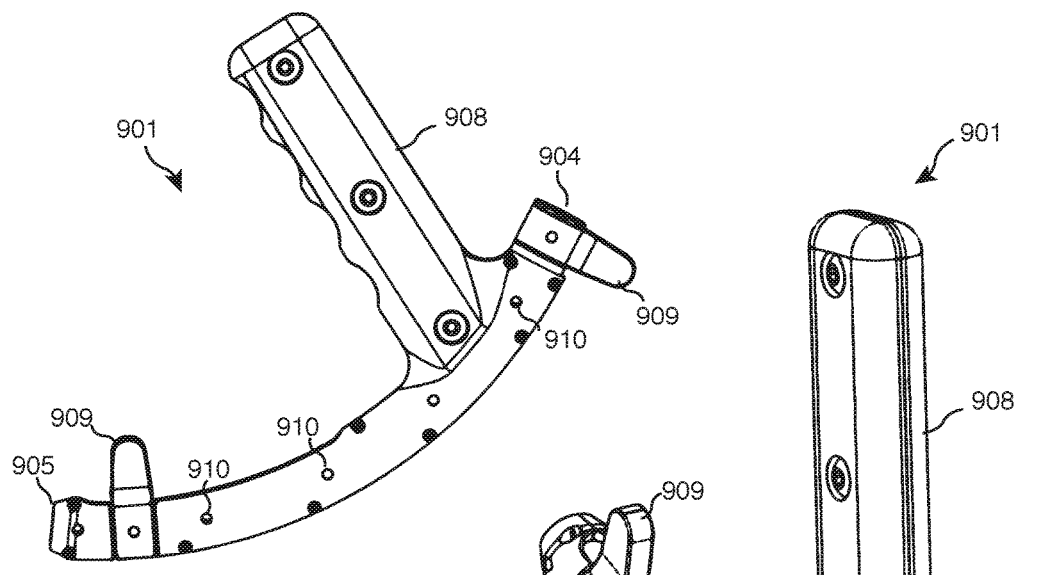
FIG. 44A. Side view of a delivery shaft in certain embodiments.
Figure 44B:
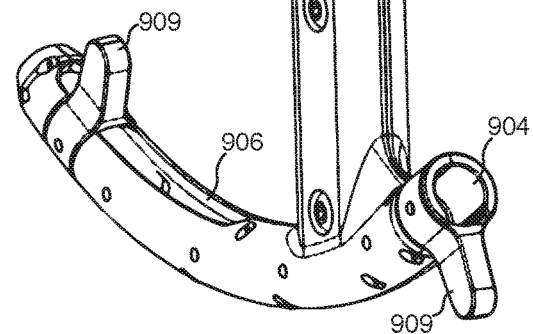
FIG. 44B. Perspective view of a delivery shaft in certain embodiments.
Figure 44C:
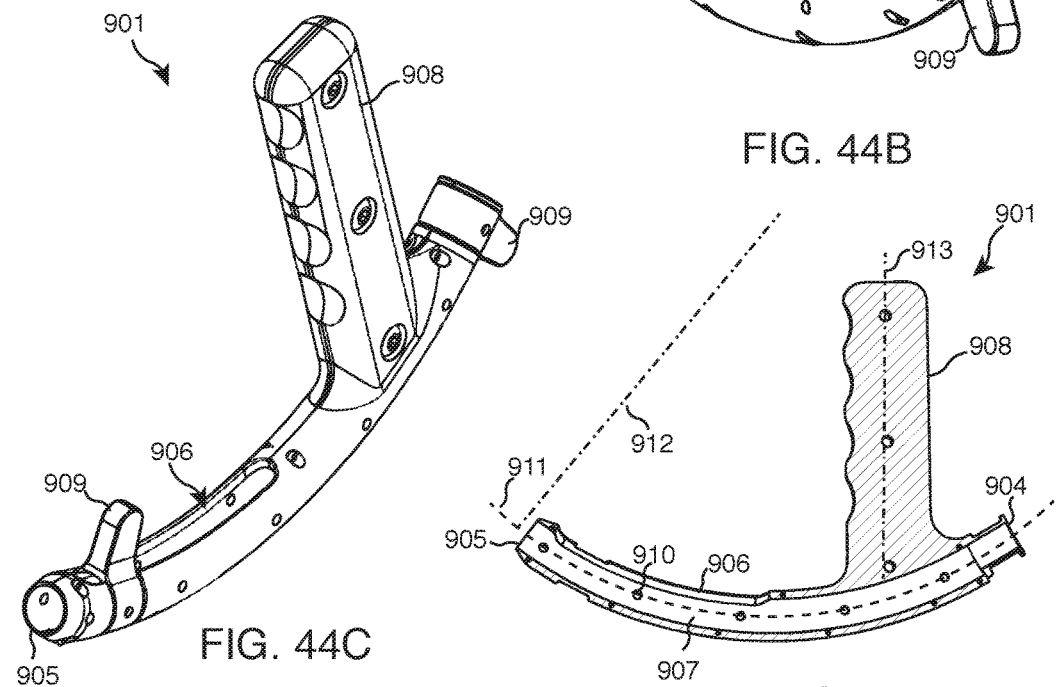
FIG. 44C. Perspective view of a delivery shaft in certain embodiments.
Figure 44D:
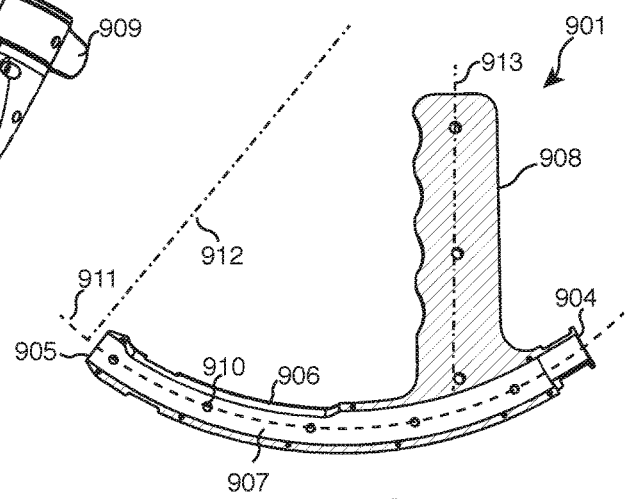
FIG. 44D. Sectional view of a delivery shaft in certain embodiments.

Referring to FIG. 44B-D, a delivery shaft 901 includes a slit or a slot 906 that communicates with the shaft pathway 907. A slot 906 typically runs along the length of a delivery shaft. In certain embodiments, more than one slot 906 may be found on a delivery shaft 901. Such slot 906 guides a protrusion or a jut of a delivery sheath 902 or a curved rod 903, shown for example in FIGS. 50B, 50D, and 50F.

Certain embodiments of a delivery shaft 901 also include a handle 908. It will be appreciated that a handle may be found in any number of sizes or shapes that allow gripping or handling of the delivery shaft. In one example, as shown in FIGS. 44A-D, a handle is located proximal to the tool insertion end 904, although a handle may be found closer to the graft delivery end 905 and/or between the tool insertion end 904 and the graft delivery end 905. In certain examples, a handle may be defined by having a handle axis 913, as shown in FIG. 44D. In certain embodiments, a handle axis may include a curvature aligned with the central axis 911. In yet another embodiment, a handle axis may be generally 90° to the central axis 911, in yet other embodiments as shown in FIG. 44D a handle axis may be oblique to the central axis 911, and in yet other embodiments, a handle axis is generally in a direction that is radial from the central axis 911. In certain embodiments, a handle axis is perpendicular to a tangent of the central axis.

Certain embodiments of a delivery shaft 901 also include ventilation holes 910 allowing sterilization of the assembly. It will be appreciated that ventilation holes 910 may be found in other instruments, assemblies, and components as described herein. In certain embodiments, a delivery shaft 901 is a unibody assembly, and in other embodiments a delivery shaft 901 includes at least two pieces.

In certain embodiments, a delivery shaft includes a retention lock that restricts movement of a curved element relative to the delivery shaft. Certain embodiments of a retention lock 909 are shown in FIGS. 44A-44D and FIG. 45A-B. Embodiments of a retention lock 909 have a collar portion 914 and a tab portion 915. A collar portion 914 wraps around a delivery shaft 901. In certain embodiments, a collar portion 914 has a cutout 916 that permits sliding of a delivery sheath or a curved rod through the cutout 916 when the retention lock embodiment is in an unlocked position, and the retention lock embodiment restricts sliding when in a locked position. In certain embodiments, a delivery shaft 901 includes a radial surface feature 917 allowing a retention lock 909 to be rotatably restricted. A radial surface feature 917 may include, for example, a radial groove (shown in FIG. 46), radial tongue, radial protrusion, and other such features that correspondingly mates with a retention lock 909 embodiment or other retention lock embodiments, as to restricts certain movements about the delivery shaft 901. In certain embodiments, a retention lock 909 is rotatably restricted to a certain angle, for example, restricted to a 90° rotation.

It will be appreciated that a retention lock includes any number of mechanisms to restrict movement of an instrument (including delivery sheath, curved rod, or other instruments) from sliding through a shaft pathway. For example, a retention lock includes, but is not limited to, a form having a collar and tab, a compression latch, clamp, tube clamp, pin, threaded members threading orthogonally to a central axis (e.g. a wing-nut), a spring-loaded ball detent, and fastener, and any other mechanical fastening structure appreciated by those skilled in the art to temporarily restricts movement of such instrument.

As seen in FIG. 47A and FIG. 47B, a delivery sheath 902 includes a first end 918 and second end 919, where a sheath pathway 920 is a pathway generally following the central axis 911 and communicating the first end 918 and second end 919. The sheath pathway is a pathway generally allows passage of other instruments, such as curved element, a curved rod 903, bony material, and other objects described herein or elsewhere relevant to surgical procedures.

Still referring to FIG. 47A and FIG. 47B the sheath pathway 920 further defines an exterior surface 922 and an interior surface 923. The delivery sheath exterior surface 922 has a protrusion or jut 921, which can act as a handle. When installed in a delivery shaft 901, the delivery sheath 902 slides through the shaft pathway 907, and the jut 921 slides or passes through the slot 906, as shown in FIG. 48. Still referring to FIG. 48, it can be seen that a jut 921 can extend beyond the exterior surface 932 of the delivery shaft 901. As seen, for example, in FIG. 47B, a jut in certain embodiments generally follows an axis 934. The jut may be an additional handle, having a length to accommodate one to two fingers, and other examples, the jut may extend further to accommodate gripping with more than one finger. A user can, for example, hold the assembly 900 by the handle 908 and pull in (or push apart) on a jut 921 (being an additional handle in this example) using a finger or multiple fingers, a thumb, or a second hand relative to a handle 908. In certain embodiments, a jut axis 934 and handle axis 913 are coplanar with said central axis 911, resembling a trigger. In certain embodiments, a handle axis and jut axis are coplanar to each other.

Referring to FIG. 48, embodiments of a delivery shaft 901 optionally has a slot end 906a, 906b that further restricts sliding or passing movement of the delivery sheath 902 past a certain point. A slot end 906a, 906b, for example, defines the slot being located within the body of delivery shaft 901, although it would be appreciated that in other embodiments, a slot communicates with a shaft end. Referring to FIG. 47A, a delivery sheath 902 optionally includes an o-ring 930 to create frictional resistance between a delivery sheath and delivery shaft interior surface 933 (FIG. 46). Also shown in FIG. 48, a retention lock 909 is in an open position as to allow slidable movement of the delivery sheath 902.

In certain embodiments, a delivery sheath outer diameter is between 10 mm and 20 mm, with preferred embodiments having a 12 mm to 13 mm outer diameter. A delivery sheath inner diameter is between 5 mm and 19 mm, with preferred embodiments further having an 11 mm inner diameter, although some embodiments may have inner and outer diameters outside of these ranges.

Figures 49A, 49B, 49C:
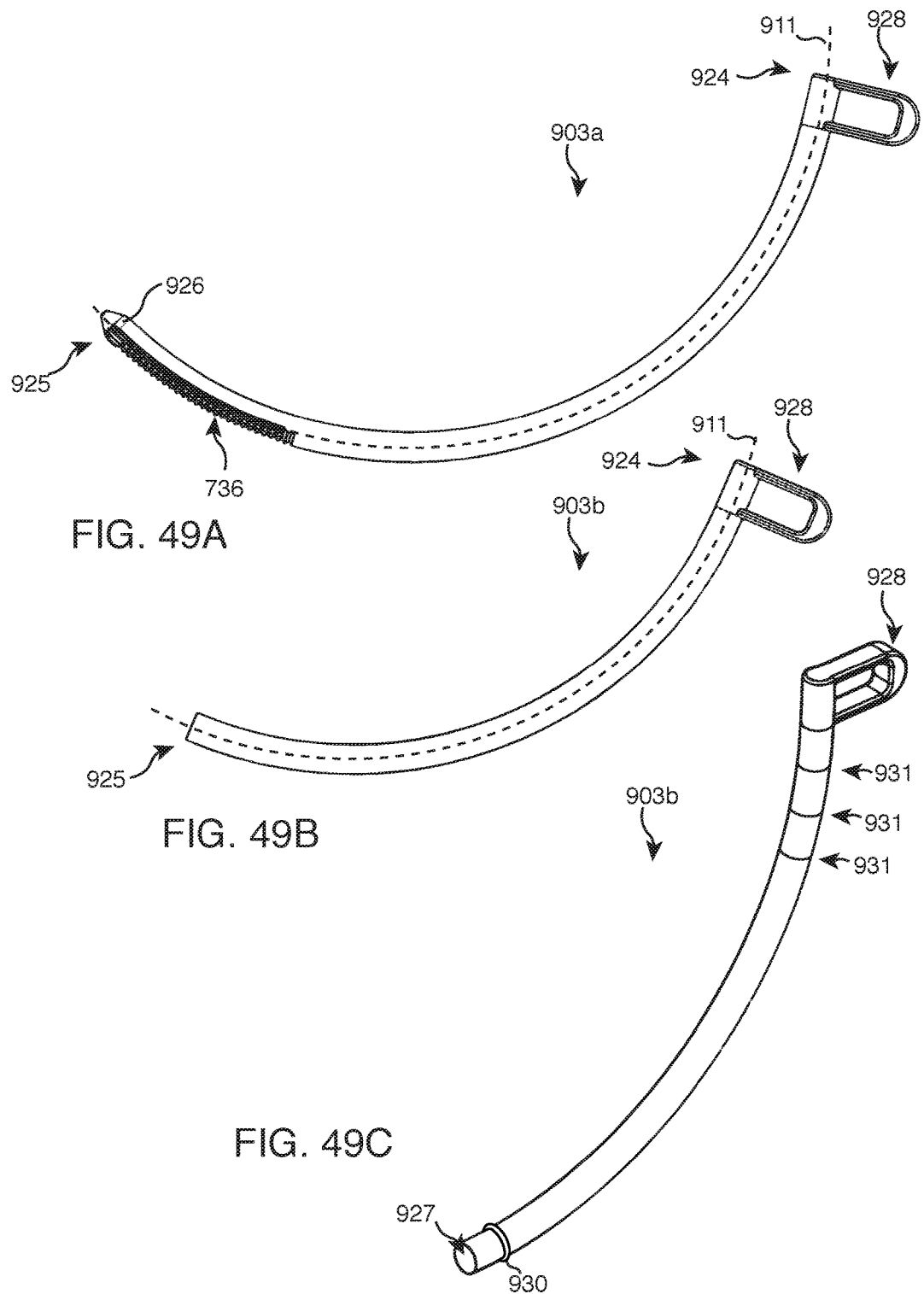
FIG. 49A. Side view of a decorticating rod in certain embodiments.
FIG. 49B. Side view of a plunging rod in certain embodiments.
FIG. 49C. Perspective view of a plunging rod in certain embodiments.

Referring to FIGS. 49A-C, embodiments of a curved rod are shown. In certain embodiments, a curved rod is further defined as a decorticating rod 903a as shown in FIG. 49A, and as a plunging rod 903b as shown in FIG. 49B-C. Referring to FIG. 49A-B, a curved rod is generally aligned with a central axis 911, and is further defined by a first end 924 and a second end 925. Certain embodiments of a decorticating rod 903a have an abrading surface 736 allowing decortication of bone surfaces.

Certain embodiments of a curved rod have a beveled end 926 as shown in FIG. 49A, allowing separation of tissue as the assembly is inserted into the body. It will be appreciated that a second end of a curved rod may have a frustoconical, conical, hemispherical, ellipsoidal, torispherical, or other type of beveled end allowing separation or cutting of tissue. In certain embodiments, a graft delivery end 905 of a curved shaft 901 has a beveled edge to match the second end of a curved rod. In certain embodiments, a plunging rod 903b has a second end 925 with a surface that allows pushing bone graft to the surgical site. In one example, a curved rod has a blunt end 927, as shown in FIG. 49B-C, although other types of ends may be used. In certain embodiments, a plunging rod 903b has a second end 925 terminating within a sheath pathway, leaving a space between a plunging rod second end 925 and a delivery sheath second end 919, where such space can be filled with bony material. It will also be appreciated that in certain embodiments, a plunging rod 903b has an abrading surface. In yet other embodiments, a curved rod has a inner pathway aligning with the central axis and communicating with a first end and a second end. In such embodiment, instruments, implants, or bony material may be inserted through such pathway.

It will be appreciated that in certain embodiments, the arc length of an assembly's elements may vary. In certain embodiments, a plunging rod 903b, has an arc length shorter than a delivery sheath's 902 arc length. This difference allows bony material to be temporarily stored in a delivery sheath pathway 920, between a delivery sheath second end 919 and a plunging rod second end 925. It can be appreciated that in certain embodiments, a first curved element may have a different arc length than a second curved element, allowing temporary storage of bony material.

Referring to FIG. 49C, certain embodiments of a curved rod have volume markers 931. When inserting a curved rod (e.g. plunging rod) through the assembly 900, the volume markers 931 allow one to determine the volume of bony material being inserted. It will be appreciated that volume markers may be placed on other components described herein, including, but not limited to the delivery sheath. Still referring to FIG. 49C, a curved rod (e.g. plunging rod)

optionally has an o-ring 930 to create frictional resistance between a delivery sheath and curved rod.

In certain embodiments, a curved rod includes a protrusion or a jut from an external surface of such curved rod. In certain embodiments, a mating feature is understood to be a type of jut. In certain embodiments, a mating feature mates with a retention lock. Referring to FIGS. 49A-C, an embodiment of a mating feature 928, can mate with a retention lock 909 to restrict movement of a curved rod relative to the delivery shaft. It will be appreciated that in other embodiments, a retention lock interacting with a mating features includes, but is not limited to, a retention latch, compression latch, clamp, tube clamp, pin, threaded members threading orthogonally to a central axis (e.g. a wing-nut), a spring-loaded ball detent, and fastener, and any other mechanical fastening structure appreciated by those skilled in the art to temporarily restricts movement of a curved rod.

Figure 51A:
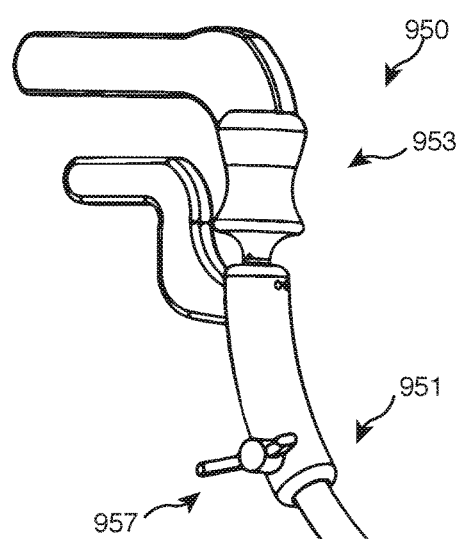
FIG. 51A. A graft delivery assembly in certain embodiments.
Figure 51B:
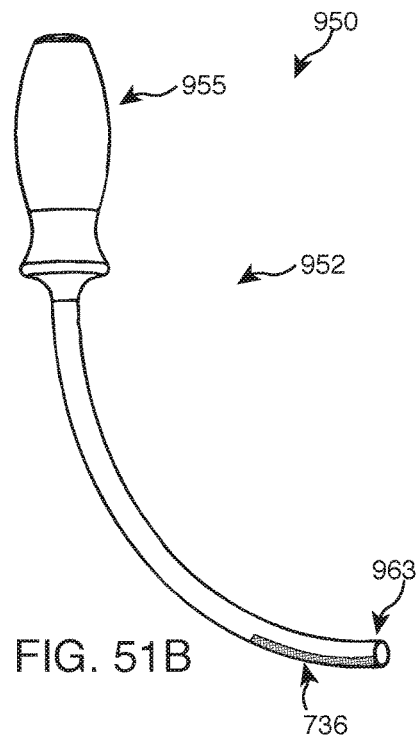
FIG. 51B. A graft delivery assembly, decorticating rod in certain embodiments.

Referring now to FIG. 51A-B, other embodiments of the invention include a graft delivery assembly 950 that includes a graft delivery shaft 951, and a curved element. In FIG. 51A-B, a curved element, such as a decorticating rod 952, and a plunging rod 953 are shown.

Certain embodiments of a delivery shaft 951, shown for example in FIG. 51A and FIGS. 53A-D, have a tool insertion end 958 and a graft delivery end 959. Referring to FIG. 53A, a delivery shaft 951 follows a central axis 960, whereby a shaft pathway 961 follows the central axis 960 and communicates the tool insertion end 958 and the graft delivery end 959. In certain embodiments, a graft delivery end 959 has a beveled end to separate tissue while advancing such instrument. It can be appreciated that certain embodiments of a graft delivery end includes a tip that allows cutting through tissue. As seen in FIG. 53A, certain embodiments of a delivery shaft include an abrading surface 736. Still referring to FIG. 53A, delivery shaft 951 has a handle 954 and a shaft segment 962.

In certain embodiments, handles having certain configurations are used. Generally, some of these handle configurations allow for simultaneous gripping of a graft delivery shaft 951, and decorticating rod 952 or plunging rod 953. In one example, a handle 954b (referring to FIG. 53B) is generally oriented along the central axis 960. In another example, a handle 954, 954a (referring to FIG. 53A) includes a grip 964a following a handle axis 965a, where a handle axis 965a is perpendicular to a tangent of the central axis 960. It will be appreciated that a handle axis 965a, 965b is not limited to such orientation, and may be located generally oblique to a central axis 960. In yet other embodiments, a handle 954, 955, 956 (seen in FIGS. 51B, 52A, 53A-D) further includes a syringe handle 954b (referring to FIG. 53C). In yet another example, a handle 954, 955, 956 includes a thumb tab 954c (referring to FIG. 53D). It will also be appreciated that other handles disclosed herein have these handle variations in certain embodiments.

Furthermore, still referring to FIG. 51A and FIGS. 53A-D, a delivery shaft 951, includes a retention lock 957, having a threaded end, where the threaded end engages with a threaded opening (not shown) in communication with the sheath pathway. Tightening or loosening of the retention lock 957 therefore regulates the passage of the decorticating rod 952, and the plunging rod 953.

Referring to FIGS. 51A-B and 53A, a decorticating rod 952 and plunging rod 953 is aligned with a central axis 960, being able to pass through the shaft pathway 961 of the graft delivery shaft 951. Embodiments of a decorticating rod 952 have an abrading surface 736. In certain embodiments, an end 963 of a decorticating rod 952 has a beveled end to separate tissue. In certain embodiments, an end 963 of a decorticating rod 952 has a blunt end. Certain embodiments of a decorticating rod 952 and plunging rod 953 include a handle 955, 956.

Figure 52A:
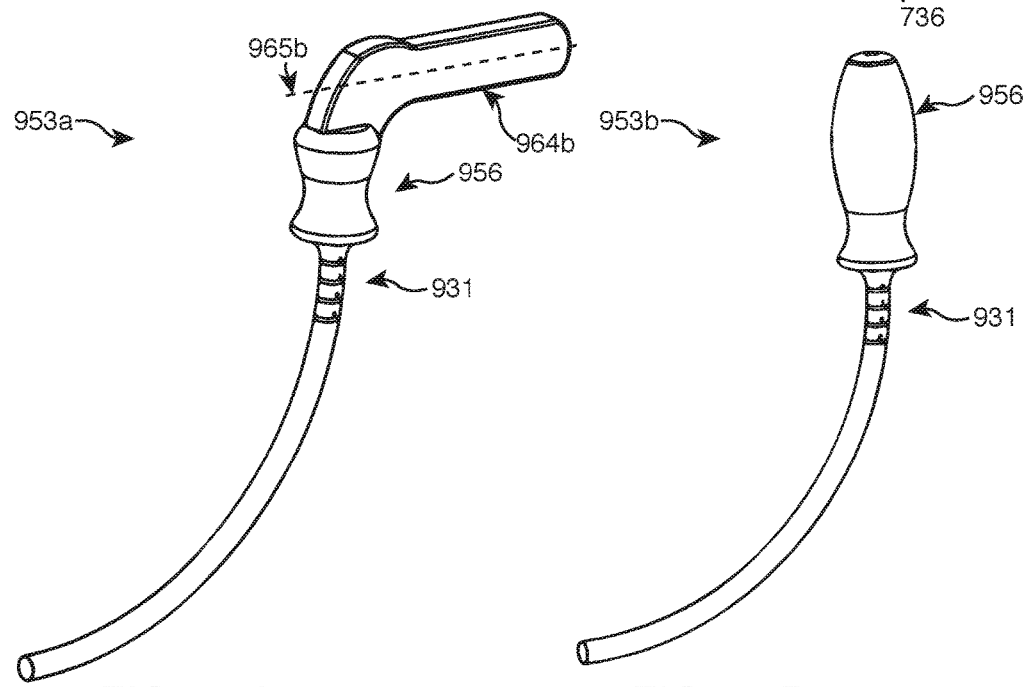
FIG. 52A. A plunging rod in certain embodiments.
Figure 52B:
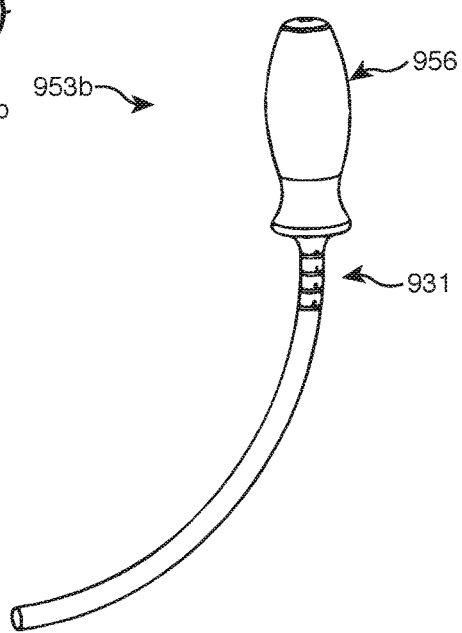
FIG. 52B. A plunging rod in certain embodiments.

Referring to FIG. 52A-B, in certain embodiments, a handle of a plunging rod 953a, 953b (or a decorticating rod in some embodiments) has a grip 964b aligned with a handle axis 965b, where a handle axis 965b is perpendicular to a tangent of the central axis 960. A plunging rod 953 has volume markers 931 to indicate the volume of bony graft dispensed from the assembly tip.

Example 1

In certain embodiments, the following exemplary steps are employed to access the intertransverse process area for decortication of the transverse processes and delivery of bony material. In preferred embodiments, the following steps are performed following surgical procedures involving placement of percutaneous pedicle screws, although in other embodiments, these steps may be performed prior to or during such procedure.

1. Assemble instruments by placing the delivery sheath 902 through the delivery shaft 901.

2. Lock the delivery sheath 902 in place by rotating the lower retention lock 909 embodiment to a lock position.

3. Lock the decorticating rod 903a within the delivery shaft 901 by rotating the upper retention lock 909 embodiment to engage with the decorticating rod mating feature 928.

4. If an adequate incision has not already been created, create a 1-2 cm incision 929 approximately two to three levels cephalad or caudal from the vertebral level requiring graft delivery (in some cases, approximately 5 cm laterally from the spinous process) (see, for example, FIG. 50A). In certain embodiments, medical practitioners may use a variety of instruments (such as Jamshidi® needles, probes) to target the intended levels.

5. Insert an embodiment of the assembly 900 (also described in Example 1, steps 1-3) through the skin incision, maneuvering the instruments to create a pathway to the surgical site. In certain embodiments, the assembly 900 has a beveled end 926 separating tissue to create a pathway to a first transverse process, and subsequently to a second transverse process (or more). If percutaneous pedicle screws have already been placed, position the end to roughly align with the most inferior/superior pedicle screw, lateral to the pedicle screw or pedicle screw tower. The concavity of the instruments should be directed out of the patient's skin (see, for example, FIG. 50A).

6. Observe fluoroscope from a lateral view to confirm trajectory and placement of the instruments to the desired vertebral level of interest. The delivery sheath should be located directly between the two transverse processes at the level of interest.

7. Rotate the delivery sheath lower retention lock 909a embodiment to the unlocked position, and pull back the delivery sheath 902 by handling the delivery sheath jut 921 to reveal the decorticating rod 903a (see, for example, FIG. 50B). In certain embodiments, a user may grasp the handle 908, and the jut 921 with a finger (e.g. index, fifth digit, thumb) or multiple fingers.

8. While holding the handle 908 on the delivery shaft, maneuver the assembly along the bony region of interest using an axially rotating motion, as well as a push-pull motion along the axis of the spine such that the abrading surface 736 decorticates the transverse processes (see, for example, FIG. 50C).

9. Once decorticated, re-deploy the delivery sheath 902, and rotate the retention lock 909 embodiment to lock the delivery sheath. Check fluoroscopy for location of the instruments and possible movement (see, for example, FIG. 50D).

10. Disengage the retention lock 909b embodiment from the decorticating rod mating feature 928, and remove the decorticating rod 903a from the assembly (see, for example, FIG. 50D).

11. Insert desired biologic and/or bony material 2406 into the delivery shaft tool insertion end 904 (see, for example, FIG. 50E).

12. Insert the plunging rod 903b through the delivery shaft 901, plunging the biologic towards the second end of the delivery shaft 902 (see, for example, FIG. 50E).

13. Once the plunging rod 903b is fully inserted, rotate the upper retention lock 909b embodiment to engage it with the plunging rod mating feature 928 (see, for example, FIG. 50F).

14. Rotate the lower retention lock embodiment to unlock the delivery sheath. Check fluoroscopy for delivery sheath position.

15. Wrapping one's hand around the handle 908, and grasping or handling the jut 921 on the delivery sheath. Pull and retract the delivery sheath, leaving the biologic 2406 behind (see, for example, FIG. 50F). Ensure the delivery shaft remains fixed in space by pulling the jut 921/delivery sheath 902 relative to the delivery shaft 901. The goal of this step is to ensure the delivery shaft and biologic remain in the desired location as confirmed by fluoroscopy, while the delivery sheath is moved out of the way. This step differs from a method of using an instrument to "push" the biologic out of the delivery sheath, and into an unwanted location.

16. Fluoroscopy confirmation step, ensure that the end of the delivery sheath has moved from the most inferior/superior pedicle screw to the most superior, or vice versa if access made from the caudal approach. The delivery sheath should not be seen in the same position as when the instrument was inserted.

17. Remove assembly, and suture incision, if appropriate.

Example 2

In certain examples, the following exemplary steps are used to access the intertransverse process area. In preferred embodiments, the following steps are performed following surgical procedures involving placement of percutaneous pedicle screws, although in other embodiments, these steps may be performed prior to or during such procedure. These steps are performed with certain embodiments of a graft delivery assembly (e.g. FIGS. 51-53)

1. Assemble instruments by placing a decorticating rod 952 through a graft delivery shaft 951, leaving space for preferred biologic at the graft delivery end 959 of the graft delivery shaft, choosing the desired volume using the volume markers 931.

2. Place the retention lock or retention lock 957 in a locking position on the graft delivery shaft 951, to prevent accidental expulsion of biologic 3. Pack the graft delivery end 959 of graft delivery shaft 951 with preferred biologic, creating a tightly packed space.

4. If an adequate incision has not already been created, create a 1-2 cm incision approximately two to three levels cephalad or caudal from the vertebral level requiring graft delivery (in some cases, approximately 5 cm laterally from the spinous process). In certain embodiments, medical practitioners may use a variety of instruments (such as Jamshidi® needles, probes) to target the intended levels.

5. Insert an embodiment of the assembly 950 through the skin incision, maneuvering the instruments so that the beveled end is roughly aligned with the most inferior/superior pedicle screw, lateral to pedicle screw or tower. The concavity of the instruments should be directed out of the patient's skin.

6. Observe fluoroscope from a lateral view to confirm trajectory and placement of the instruments to the desired vertebral level of interest.

7. While handling the graft delivery shaft handle 954 and/or grip 964a, and a decorticating rod handle 955 or plunging rod handle 956, maneuver the instrument along the bony region of interest in a rocking motion and a push-pull motion along the axis of the spine to decorticate the bone. Once satisfied, unlock or loosen the retention lock 957.

8. While holding a handle 955, 956 and/or grip 964b in a fixed position in space, grasp the shaft handle 954 and/or grip 964a and firmly pull the graft delivery shaft 951 upwards toward. Ensure the decorticating rod or plunging rod handle remains fixed in space by pulling the graft delivery shaft relative to the rod. The goal of this step is to ensure the biologic remain in the desired location as confirmed by fluoroscopy, while the delivery shaft is moved out of the way.

9. Fluoroscopy confirmation step, ensure that the end of the delivery shaft has moved from the most inferior/superior pedicle screw to the most superior, or vice versa if access made from the caudal approach. The delivery shaft should not be seen in the same position as when the instrument was inserted.

Remove assembly, and suture incision, if appropriate.

In certain embodiments, instruments, assemblies, parts, portions, fasteners, and other features described herein may me made of materials metallic, including, but not limited to, biocompatible metals and alloys, such as titanium, tantalum, stainless steels, gold, silver, cobalt, chromium, platinum, ruthenium, rhodium, rhenium, and other alloys thereof, combinations thereof, or other equivalent material intended to bridge one or more transverse processes through utilization of the method steps and apparatuses disclosed herein. Instruments, assemblies, parts, portions, fasteners, and other features described herein may describe polymers, including, but not limited to polymethyl methacrylate (PMMA), polyetheretherketone (PEEK), polymethymethacrylate (PMMA), polyglycolic acid and/or polylactic acid compounds, polystyrene (PS), polyesters (PET, polycaprolacton, polyglycolied, poylactide, poly-p-dixanone, poly-hydroxybutylate), polyvinylchloride (PVC), polyethylene (PE, HDPE, UHMWPE, etc.), polyamides (Nylons, aromatic polyamides), polypropylene (PP), fluorocarbon polymers (PTFE, PTFCE, PVF, FEP), polyphenylsulfones (PPSU, e.g. Radel®), acetal copolymers, and other biocompatible materials.

Certain embodiments of the invention are designed for use with other spinal surgery procedures. It is appreciated that embodiments of the inventions mentioned herein can be used before or after other orthopedic procedures. For example, these orthopedic procedures may include, but are not limited to: pedicle screw placement, minimally invasive pedicle screw placement, minimally invasive screw/rod systems, multi-level screw/rod systems, scoliosis correction, posterior lumbar interbody fusion, anterior lumbar interbody fusion, posterior lumbar interbdoy fusion, transforaminal lumbar interbody fusion, oblique lumbar interbody fusion, eXtreme Lateral Interbody Fusion®, axial lumbar interbody fusion, anterior cervical discectomy and fusion, kyphoplasty, laminoplasty, laminotomy, sacroiliac fusion, and others.

Due to the minimally invasive nature of the system and instruments described, the procedures can be performed through the same or similar openings used for other minimally invasive procedures. In one use case, certain embodiments described herein are used in conjunction with a minimally invasive pedicle screw/rod system. A minimally invasive pedicle screw/rod system, as it is commonly known, includes creating at least one incision to access the pedicles of two or more adjacent vertebrae. It will be appreciated that in certain embodiments, the instrumentation described herein allows for depositing bony material through the same incision as that of a minimally invasive pedicel screw/rod system. In general, the present inventors have contemplated that by minimizing the size of the required incisions for posterolateral spinal fusion through use of the apparatuses and methods disclosed herein, less trauma is introduced to the tissue, leading to, for example, faster recovery and less complications.

The illustrations of arrangements described herein are intended to provide a general understanding of the structure of various embodiments, and they are not intended to serve as a complete description of all the elements and features of apparatus and systems that might make use of the structures described herein. Many other arrangements will be apparent to those of skill in the art upon reviewing the above description. Other arrangements may be utilized and derived therefrom, such that structural and logical substitutions and changes may be made without departing from the scope of this disclosure. Figures are also merely representational and may not be drawn to scale. Certain proportions thereof may be exaggerated, while others may be minimized. Accordingly, the specification and drawings are to be regarded in an illustrative rather than a restrictive sense.

The preceding description has been presented with reference to various embodiments. Persons skilled in the art and technology to which this application pertains will appreciate that alterations and changes in the described structures and methods of operation can be practiced without meaningfully departing from the principle, spirit and scope.

The present systems, methods, means, and enablement are not limited to the particular systems and methodologies described, as there can be multiple possible embodiments, which are not expressly illustrated in the present disclosures. It is also to be understood that the terminology used in the description is for the purpose of describing the particular versions or embodiments only, and is not intended to limit the scope of the present application.

Some embodiments, illustrating its features, will now be discussed in detail. The words "comprising," "having," "containing," and "including," and other forms thereof, are intended to be equivalent in meaning and be open ended in that an item or items following any one of these words is not meant to be an exhaustive listing of such item or items, or meant to be limited to only the listed item or items. It must also be noted that as used herein and in the appended claims, the singular forms "a," "an," and "the" include plural references unless the context clearly dictates otherwise. The disclosed embodiments are merely exemplary.

The claimed invention is:

1. A medical device assembly for delivering bone graft, comprising:

a delivery shaft, said delivery shaft having a tool insertion end and a graft delivery end, said delivery shaft aligned with a central axis further comprising a curvature, said central axis defining a shaft pathway extending between said tool insertion end and said graft delivery end, said delivery shaft further comprising a handle, said delivery shaft further comprising a retention lock; and a first curved element having a first end, a second end, and an exterior surface, said first curved element having a curvature aligned with said curved central axis, said first curved element being axially slidable through said shaft pathway, said first curved element further comprising a handle, wherein said delivery shaft retention lock is adapted to retain said first curved element from sliding.

2. The assembly of claim 1, said delivery shaft further comprising a slot, said slot in communication with said delivery shaft pathway, and wherein said first curved element handle is a jut protruding from said first curved element exterior surface, said jut correspondingly passing through said slot and extending past the delivery shaft exterior surface.

3. The assembly of claim 2, wherein said slot further comprises a slot end.

4. The assembly of claim 1 further comprising a second curved element;

said first curved element further comprising a pathway extending between said first end and said second end, and defining a hollow form with an interior surface;

said second curved element having a first end, a second end, and an exterior surface, said second curved element being axially slidable through said first curved element pathway; and said delivery shaft further comprising a second retention lock adapted to retain said second curved element from sliding.

5. The assembly of claim 4, said second curved element comprising a mating feature, said mating feature engageable with said second retention lock.

6. The assembly of claim 4, said second curved element further comprising an abrading surface.

7. The assembly of claim 4, said second curved element second end further comprising a beveled end configured to create a pathway through tissue.

8. The assembly in claim 1, said retention lock further comprising a collar portion rotatable about said curved shaft central axis, and being able to restrict the slideable movement of said first curved element.

9. The assembly in claim 1, wherein said central axis curvature comprises an arc having a radius adapted to follow a lordotic curvature of the spine.

10. The assembly of claim 1, said first curved element further comprising an abrading surface.

11. The assembly of claim 1, said first curved element second end further comprising a beveled end configured to create a pathway through tissue.

12. A medical device assembly for delivering bone graft, comprising:

a delivery shaft, said delivery shaft having a tool insertion end and a graft delivery end, said delivery shaft aligned with a central axis further comprising a curvature, said central axis defining a shaft pathway extending between said tool insertion end and said graft delivery end, said delivery shaft further comprising a handle;

a first curved element having a first end, a second end, and an exterior surface, said first curved element having a curvature aligned with said curved central axis, said first curved element being axially slidable through said shaft pathway, said first curved element further comprising a pathway extending between said first end and said second end, and defining a hollow form with an interior surface; said first curved element further comprising a handle; and a second curved element having a first end, a second end, and an exterior surface, said second curved element being axially slidable through said first curved element pathway.

13. The assembly of claim 12, wherein said delivery shaft further comprises a retention lock, wherein said delivery shaft retention lock prevents said first curved element from sliding.

14. The assembly in claim 13, wherein said retention lock comprises a collar portion rotatable about said delivery shaft central axis, and restricting slideable movement of said first curved element when said retention lock is positioned in a locking position.

15. The assembly in claim 13, wherein said delivery shaft further comprises a second retention lock wherein said delivery shaft second retention lock prevents said second curved element from sliding.

16. The assembly of claim 12, said delivery shaft further comprising a slot, said slot in communication with said delivery shaft pathway, and wherein said first curved element handle is a jut protruding from said first curved element exterior surface, said jut correspondingly passing through said slot and extending past the delivery shaft exterior surface.

17. The assembly in claim 12, wherein said second curved element further comprises a beveled second end and an abrading surface.

18. A method of placing bony material between adjacent transverse processes, comprising:
    making an incision in the skin on the posterior side of a patient offset from the medial plane and in proximity to a transverse process;
    creating a pathway to a first transverse process through said incision with an assembly;
    extending said pathway to at least a second transverse process adjacent to said first transverse process with said assembly; and
    dispensing bony material through said pathway depositing bony material between said first transverse process and said second transverse process.

19. The method in claim 18, further comprising:
    decorticating the posterior surface of said first transverse process and said at least second transverse process through said pathway, wherein said assembly further comprises an ablating surface configured for decorticating said transverse processes.

20. The method in claim 18, further comprising:
    pre-loading said assembly with bony material and dispensing said bony material between said first transverse process and said at least second transverse process.

* * * * *